US006608203B2

(12) United States Patent  
Cameron et al.

(10) Patent No.: US 6,608,203 B2  
(45) Date of Patent: Aug. 19, 2003

(54) TETRAHYDROISOQUINOLINE COMPOUNDS AS ESTROGEN AGONISTS/ANTAGONISTS

(75) Inventors: Kimberly O. Cameron, East Lyme, CT (US); Richard Chesworth, Mystic, CT (US); Paul A. DaSilva-Jardine, Providence, RI (US); Robert F. Day, Groton, CT (US); Bruce A. Lefker, Gales Ferry, CT (US); Michael P. Zawistoski, West Warwick, RI (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/745,396

(22) Filed: Dec. 21, 2000

(65) Prior Publication Data

US 2001/0039285 A1 Nov. 8, 2001

Related U.S. Application Data

(60) Provisional application No. 60/173,063, filed on Dec. 24, 1999.

(51) Int. Cl.[7] .................. C07D 217/06; A61K 31/47
(52) U.S. Cl. ........................... 546/147; 514/311
(58) Field of Search ...................... 546/147; 514/311

(56) References Cited

U.S. PATENT DOCUMENTS

| | | | |
|---|---|---|---|
| 3,234,090 A | 2/1966 | Huebner et al. ............. 167/58 |
| 3,274,213 A | 9/1966 | Lednicer ................. 260/326.5 |
| 3,277,106 A | 10/1966 | Bencze et al. ............. 260/295 |
| 3,666,763 A | 5/1972 | Grether et al. ............. 260/289 |
| 4,113,869 A | 9/1978 | Gardner .................... 424/258 |
| 4,133,814 A | 1/1979 | Jones et al. ............. 260/326.55 |
| 4,340,601 A | 7/1982 | Brenner .................... 424/258 |
| 4,418,068 A | 11/1983 | Jones ....................... 424/267 |
| 5,462,950 A | 10/1995 | Fontana ..................... 514/324 |
| 5,496,828 A | 3/1996 | Cullinan .................... 514/324 |
| 5,521,214 A | 5/1996 | Bryant et al. .............. 514/443 |
| 5,552,412 A | 9/1996 | Cameron et al. ............ 514/317 |
| 5,554,628 A | 9/1996 | Bryant et al. .............. 514/319 |
| 5,599,822 A | 2/1997 | Cullinan et al. ............ 514/324 |
| 5,670,523 A | 9/1997 | Brandi et al. .............. 514/324 |

FOREIGN PATENT DOCUMENTS

| | | | |
|---|---|---|---|
| CH | 538477 | 6/1973 | |
| EP | 0286293 | 3/1988 | |
| EP | 0514851 | 5/1992 | |
| EP | 0659424 | 6/1995 | ......... A61K/31/445 |
| EP | 0702962 | 3/1996 | .......... A61K/45/06 |
| EP | 0729754 | 9/1996 | .......... A61K/31/40 |
| EP | 792641 | * 9/1997 | |
| EP | 792642 | * 9/1997 | |
| EP | 792645 | * 9/1997 | |
| EP | 0826670 | 3/1998 | ......... C07D/211/14 |
| EP | 0826679 | 3/1998 | ......... C07D/295/08 |
| EP | 842661 | * 5/1998 | |
| EP | 0911321 | 10/1998 | |
| JP | 3294268 | 12/1991 | |
| WO | WO9609040 | 3/1996 | .......... A61K/31/34 |
| WO | 9621656 | * 7/1996 | |
| WO | WO9640134 | 12/1996 | ......... A61K/31/445 |
| WO | WO9713511 | 4/1997 | .......... A61K/31/40 |
| WO | WO9713764 | 4/1997 | ......... C07D/333/64 |
| WO | 9724369 | * 7/1997 | |
| WO | WO9726876 | 7/1997 | .......... A61K/31/44 |
| WO | 9731640 | * 9/1997 | |
| WO | WO0055137 | 9/2000 | |

OTHER PUBLICATIONS

Osteoporosis Conf. Scrip No. 1812/13, p. 29 (Apr. 16–20, 1993).
Jordan et al., *Breast Cancer Res. Treat.*, 10(1):31–36 (1987).
Jones et al., *Med. Chem.*, 27:1057–66 (1984).
Lednicer et al., *J. Med. Chem.*, 12:881 (1969).
Bencze et al., *J. Med. Chem.*, 10:138 (1967).
Lednicer et al., *J. Med. Chem.*, 10:78 (1967).
Nagarajan et al, *Ind. J. Chem.*, 24B:83–97 (1985).
Hibert et al., *J. Med. Chem.*, 33:1594 (1990).

* cited by examiner

*Primary Examiner*—D. Margaret Seaman
(74) *Attorney, Agent, or Firm*—Peter C. Richardson; Gregg C. Benson; John A. Wichtowski

(57) ABSTRACT

This invention relates to compounds useful for treating or preventing obesity, breast cancer, osteoporosis, endometriosis, cardiovascular disease, prostatic disease, and the like, and to pharmaceutical composition, methods, and kits comprising such compounds.

57 Claims, No Drawings

TETRAHYDROISOQUINOLINE COMPOUNDS AS ESTROGEN AGONISTS/ANTAGONISTS

CROSS REFERENCE TO RELATED APPLICATION

This application claims priority of U.S. provisional application No. 60/173,063, filed Dec. 24, 1999.

This invention relates to novel tetrahydroisoquinoline compounds that are useful as estrogen agonists and antagonists, and the pharmaceutical uses thereof.

BACKGROUND OF THE INVENTION

The value of naturally occurring estrogens and synthetic compositions demonstrating "estrogenic" activity has typically been in their medical and therapeutic uses. A traditional listing of the therapeutic applications for estrogens alone or in combination with other active agents includes, but is not limited to, oral contraception, relief for the symptoms of menopause, prevention of threatened or habitual abortion, relief of dysmenorrhea, relief of dysfunctional uterine bleeding, an aid in ovarian development, treatment of acne, diminution of excessive growth of body hair in women (hirsutism), the prevention of cardiovascular disease, treatment of osteoporosis, treatment of prostatic carcinoma, and suppression of postpartum lactation (Goodman and Gilman, The Pharmacological Basis Of Therapeutics (7th Ed.), Macmillan Publishing Company, 1985, pages 1421–1423). Accordingly, there has been increasing interest in finding newly synthesized compounds and new uses for previously known compounds that are demonstrably estrogenic, that is, able to mimic the action of estrogen in estrogen responsive tissue.

From the viewpoint of pharmacologists interested in developing new drugs useful for the treatment of human diseases and specific pathological conditions, it is desirable to procure compounds having demonstrable estrogen-like function, but which are devoid of unwanted side-effects. Exemplifying this latter view, osteoporosis, a disease in which bone becomes increasingly more fragile, is greatly ameliorated by the use of fully active estrogens. However, due to the recognized increased risk of uterine cancer in patients treated chronically with active estrogens, it is not clinically advisable to treat osteoporosis in intact women with fully active estrogens for prolonged periods.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip, and 240,000 wrist fractures annually. These injuries cost the nation over $10 billion per year. Hip fractures are the most serious, with 5–20% of patients dying within one year, and over 50% of the survivors being incapacitated.

The elderly are at greatest risk of osteoporosis, and the problem is therefore predicted to increase significantly with the aging of the population. Worldwide fracture incidence is forecast to increase 3-fold over the next 60 years, and one study estimates there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle, and low calcium intake.

Estrogen is the agent of choice in preventing osteoporosis or post menopausal bone loss in women; it is the only treatment that unequivocally reduces fractures. However, estrogen stimulates the uterus and is associated with an increased risk of endometrial cancer. Although the risk of endometrial cancer is thought to be reduced by a concurrent use of a progestogen, there remains concern about possible increased risk of breast cancer with the use of estrogen.

Black et al., in EP 0605193A1, report that estrogen, particularly when taken orally, lowers plasma levels of LDL and raises plasma levels of the beneficial high density lipoproteins (HDLs). Thus, estrogen can be an effective therapy for hypercholesterolemia. However, as discussed supra, long-term estrogen therapy has been implicated in a variety of disorders, including an increase in the risk of uterine and breast cancer, causing many women to avoid this treatment. Recently suggested therapeutic regimens, that seek to lessen the cancer risk, such as administering combinations of progestogen and estrogen, cause the patient to experience unacceptable bleeding. Furthermore, combining progestogen with estrogen seems to blunt the desired serum cholesterol effects of estrogen. The significant undesirable effects associated with estrogen therapy support the need to develop alternative therapies for hypercholesterolemia that have the desirable effect on serum LDL but do not cause undesirable effects.

There is a need for improved estrogen agonists that exert selective effects on different tissues in the body. Tamoxifen, or 1-(4-β-dimethylaminoethoxyphenyl)-1,2-diphenyl-but-1-ene, is an antiestrogen that has a palliative effect on breast cancer, but is reported to have estrogenic activity in the uterus. Gill-Sharma et al., *J. Repr. Fert.*, 99:395 (1993), discloses that tamoxifen at 200 and 400 mg/kg/day reduces the weights of the testes and secondary sex organs in male rats.

Recently it has been reported (Osteoporosis Conf. Scrip No. 1812/13, p. 29 (Apr. 16–20, 1993)) that raloxifene, or 6-hydroxy-2-(4-hydroxyphenyl)-3-[4-(2-piperidinoethoxy) benzoyl] benzo[b] thiophene, mimics the favorable action of estrogen on bone and lipids but, unlike estrogen, has minimal uterine stimulatory effect. (Jordan et al., *Breast Cancer Res. Treat.*, 10(1):31–36 (1987)).

Neubauer et al., *The Prostate*, 23:245 (1993), teaches that raloxifene treatment of male rats produced regression of the ventral prostate.

Raloxifene and related compounds are described as antiestrogenic and antiandrogenic materials that are effective in the treatment of certain mammary and prostate cancers. See U.S. Pat. No. 4,418,068 and Jones et al., *J. Med. Chem.*, 27:1057–66 (1984).

Jones et al. in U.S. Pat. No. 4,133,814 describe derivatives of 2-phenyl-3-aroylbenzothiophene and 2-phenyl-3-aroylbenzothiophene-1-oxides that are useful as antifertility agents, and also suppress the growth of mammary tumors.

Lednicer et al., *J. Med. Chem.*, 12:881 (1969), describes estrogen antagonists of the structure

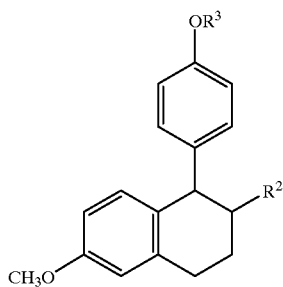

wherein $R^2$ is phenyl or cyclopentyl and $R^3$ is H, —CH$_2$CHOHCH$_2$OH, or

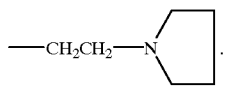

Bencze et al., *J. Med. Chem.*, 10:138 (1967), prepared a series of tetrahydronaphthalenes intended to achieve separation of estrogenic, antifertility, and hypocholesterolemic activities, although they were only partially successful in doing so. These structures have the general formula:

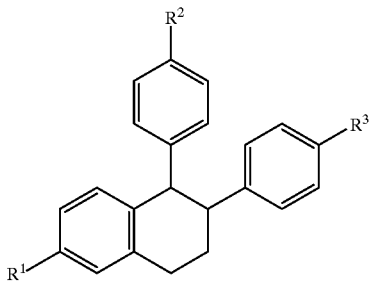

wherein $R^1$ is H or OCH$_3$, $R^2$ is H, OH, OCH$_3$, OPO(OC$_2$H$_5$)$_2$, OCH$_2$CH$_2$N(C$_2$H$_5$)$_2$, OCH$_2$COOH, or OCH(CH$_3$)COOH, and $R^3$ is H or Cl.

U.S. Pat. No. 3,234,090 discloses compounds having estrogenic and antifungal properties, as well as procedures for the preparation of these compounds. The described compounds have the formula:

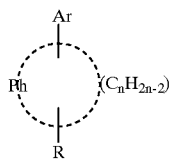

in which Ph is a 1,2-phenylene radical, Ar is a monocyclic carbocyclic aryl group substituted by tertiary amino-lower alkyl-oxy, in which the tertiary amino is separated from the oxy by at least two carbon atoms, R is hydrogen, an aliphatic radical, a carbocyclic aryl radical, a carbocyclic aryl-aliphatic radical, a heterocyclic aryl radical, or a heterocyclic aryl aliphatic radical, the group of the formula —(C$_n$H$_{2n-2}$)— stands for an unbranched alkylene radical having from three to five carbon atoms and carrying the groups Ar and R, salts, N-oxides, salts of N-oxides, or quaternary ammonium compounds thereof.

U.S. Pat. No. 3,277,106 refers to basic ethers with estrogenic, hypocholesterolemic, and antifertility effects, those ethers having the formula:

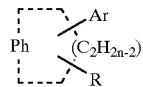

in which Ph is a 1,2-phenylene radical, Ar is a monocyclic aryl radical substituted by at least one amino-lower alkyloxy group in which the nitrogen atom is separated from the oxygen atom by at least two carbon atoms, R is an aryl radical, and the portion —(C$_n$H$_{2n-2}$)— stands for lower alkylene forming with Ph a six- or seven-membered ring, two of the ring carbon atoms thereof carry the groups Ar and R, salts, N-oxides, salts of N-oxides, and quaternary ammonium compounds thereof.

Lednicer et al., in *J. Med. Chem.*, 10:78 (1967), and in U.S. Pat. No. 3,274,213, refer to compounds of the formula

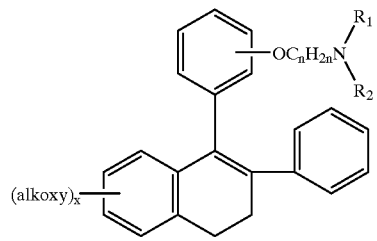

wherein $R_1$ and $R_2$ are selected from the class consisting of lower alkyl and lower alkyl linked together to form a 5 to 7 ring member saturated heterocyclic radical.

PCT publication No. WO 96/09040 A1 discloses a benzofuran compound useful for treatment of medical indications associated with post-menopausal syndrome, e.g., uterine fibroid disease, endometriosis, and aortal smooth muscle cell proliferation.

European Patent Application EP 0,826,670 A1 discloses naphthalene compounds and methods for inhibiting estrogen deficient pathologies such as lack of birth control, post-menopausal syndrome including osteoporosis, cardiovascular disease, restenosis and hyperlipidemia, prostate cancer, acne, hirsutism, dysfunctional uterine bleeding, dysmenorrhea, and atrophic vaginitis.

European Patent Application EP 0,659,424 A1 discloses benzothiophene compounds useful for treating male infertility.

U.S. Pat. No. 5,462,950 discloses the use of benzothiophene compounds for treating physical menstrual symptoms.

PCT Publication WO 96/40134 discloses methods of antagonizing or blocking calcium channels in vascular tissue comprising administering a benzothiophene compound.

U.S. Pat. No. 5,521,214 discloses methods of inhibiting environmental estrogens comprising administering a benzothiophene compound.

U.S. Pat. No. 5,554,628 discloses methods for minimizing the uterotrophic effect of tamoxifen and its analogs by administering a naphthalene compound.

PCT Publication WO 97/13764 discloses benzothiophene compounds useful for inhibiting cardiovascular disease including restenosis and atherosclerosis.

PCT Publication WO 97/13511 discloses benzothiophene compounds useful for inhibiting plasminogen activator inhibitor 1 related conditions such as major tissue damage and trauma, or multiple organ dysfunction syndrome.

European Patent Application 0,729,754 A2 discloses benzothiophene compounds useful for inhibiting estrogen positive tumors of the brain or CNS.

U.S. Pat. No. 5,670,523 discloses benzothiophene compounds useful for inhibiting musculoaponeurotic fibromatoses previously classified as desmoid tumors.

U.S. Pat. No. 5,496,828 discloses methods for inhibiting ulcerative mucositis by administering a benzothiophene compound.

PCT Publication WO 97/26876 discloses methods for increasing sphincter competence by administering a benzothiophene compound.

European Patent Application 0,826,679 A2 discloses a pharmaceutical composition useful for alleviating symptoms of postmenopausal syndromes, the composition comprising a naphthalene compound and an additional therapeutic agent such as estrogen or progestin, a benzothiophene compound such as raloxifene, a naphthyl compound having antiestrogen activity, a bisphosphonate compound such as alendronate or tiludronate, parathyroid hormone (PTH), including truncated and/or recombinant forms of PTH such as PTH (1-34), calcitonin, bone morphogenic proteins (BMPs), or combination thereof.

European Patent Application 0,702,962 A2 discloses a pharmaceutical agent for treating breast cancer, the agent comprising tamoxifen and a naphthyl compound useful for inhibiting hormone-dependent breast cancer.

U.S. Pat. No. 5,599,822 discloses a pharmaceutical composition for minimizing the bone loss effect of danazol, the composition comprising danazol and a benzothiophene compound having antiestrogen activity.

SUMMARY OF THE INVENTION

This invention relates to novel tetrahydroisoquinoline compounds that are useful as estrogen agonists and antagonists, and the pharmaceutical uses thereof.

In a first aspect, this invention provides compounds of the formula:

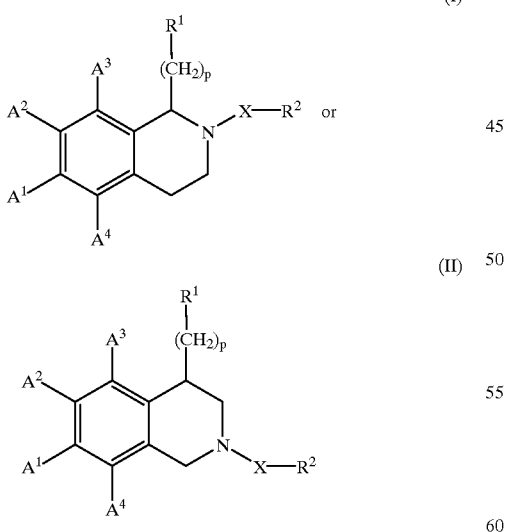

wherein:

$A^1$ is hydrogen, hydroxy, $(C_1-C_4)$alkoxy, or $(C_1-C_4)$alkanoyloxy, said $(C_1-C_4)$alkoxy or said $(C_1-C_4)$alkanoyloxy being optionally substituted by hydroxy, halo, or a partially saturated, fully saturated, or fully unsaturated five to twelve membered ring optionally having up to four heteroatoms independently selected from oxygen, sulfur, and nitrogen, or $A^1$ is $R^3$—$(C_{1-C4})$alkoxy wherein $R^3$ is pyrrolidino, piperidino, morpholino, or dimethylamino;

$A^2$, $A^3$, and $A^4$ are independently selected from hydrogen, hydroxy, $(C_1-C_4)$alkoxy, and halo;

$R^1$ is phenyl; pyridyl; piperidinyl; $(C_1-C_7)$alkyl; adamantyl; a partially saturated, fully saturated, or fully unsaturated three to twelve membered ring optionally having up to four heteroatoms selected independently from oxygen, sulfur, and nitrogen; a bicyclic ring consisting of two fused independently partially saturated, fully saturated, or fully unsaturated five to six membered rings, wherein said bicyclic ring includes up to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, wherein said bicyclic ring system includes up to four heteroatoms independently selected from oxygen, sulfur, and nitrogen; wherein each of the above $R^1$ groups is optionally substituted with up to seven fluoro atoms, or with up to three substituents independently selected from Group A, wherein Group A consists of hydroxy, halo, $(C_1-C_4)$alkyl, $(C_1-C_4)$alkoxy, $(C_3-C_8)$cycloalkyl, $R^3$—$(C_1-C_4)$alkoxy, $(C_2-C_4)$alkenyl-COOR$^7$ wherein $R^7$ is hydrogen or $(C_1-C_4)$alkyl, $(C_0-C_4)$alkyl-COOR$^7$, $(C_1-C_4)$alkanoyloxy-$(C_2-C_4)$alkenyl, $(C_2-C_4)$alkenyl-CONR$^4$R$^5$ wherein $R^4$ and $R^5$ are independently hydrogen, $(C_1-C_4)$alkyl, hydroxy $(C_1-C_4)$alkyl, $(C_1-C_4)$alkoxy-$(C_1-C_4)$alkylene, or $(C_3-C_8)$cycloalkyl, or $R^4$ and $R^5$ taken together with the nitrogen atom to which they are attached form pyrrolidino, piperidino, morpholino, or hexamethyleneimino, $(C_0-C_4)$alkyl-CONR$^4$R$^5$, $(C_0-C_4)$alkyl-NR$^4$R$^5$, OCH$_2$CH$_2$NR$^8$R$^9$ wherein $R^8$ and $R^9$ are independently methyl or ethyl, or $R^8$ and $R^9$ taken together with the nitrogen atom to which they are attached form pyrrolidino, piperidino, morpholino, or hexamethyleneimino, propyl-R$^8$R$^9$, and SO$_2$—R$^6$ wherein $R^6$ is imidazolyl, thienyl, benzathienyl, or isoxazyl, optionally substituted with up to three substituents independently selected from $(C_1-C_4)$alkyl;

X is a covalent bond, $(CH_2)_n$ where n is 1, 2, or 3, $(C_0-C_1)$alkylene-phenylene-$(C_0-C_1)$alkylene, CO$_2$, $(C_0-C_3)$alkylene-CO—$(C_0-C_3)$alkylene, or $(C_0-C_4)$alkylene-SO$_2$—$(C_0-C_4)$alkylene;

$R^2$ is $(C_1-C_9)$alkyl; $(C_2-C_4)$alkenyl; benzhydryl; a partially saturated, fully saturated, or fully unsaturated three to eight membered ring optionally having up to four heteroatoms selected independently from oxygen, sulfur, and nitrogen; a bicyclic ring consisting of two fused independently partially saturated, fully saturated, or fully unsaturated five to six membered rings, wherein said bicyclic ring includes up to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, wherein said bicyclic ring system includes up to four heteroatoms independently selected from oxygen, sulfur, and nitrogen; wherein said $(C_1-C_9)$alkyl is optionally substituted with one to seven fluoro substituents, or up to three substituents independently selected from Group B, wherein Group B consists of chloro, $(C_1-C_4)$alkoxy, amino, and $(C_1-C_4)$ alkylcarbonyl; wherein said $(C_2-C_4)$alkenyl is optionally substituted with up to three substituents independently selected from Group C, wherein Group C consists of halo, $(C_1-C_4)$alkoxy, amino, and $(C_1-C_4)$ alkylcarbonyl; and wherein said benzhydryl, said 5 to 8 membered ring, said bicyclic ring, and said bicyclic ring system is optionally substituted with up to three substituents independently selected from Group D, wherein Group D consists of halo, hydroxy, $(C_1-C_4)$ alkyl, $(C_1-C_4)$alkoxy, imidazolyl, amino, $(C_1-C_4)$ alkylcarbonylamino, and $(C_1-C_4)$alkylcarbonyl; and p is 0, 1, or 2;

with the proviso that when X is $(CH_2)_2$ or $(CH_2)_3$, p is 0, and $R^1$ is phenyl or phenyl substituted with a single chloro, fluoro, bromo, hydroxy, methoxy, pyrrolidinoethoxy, piperidinoethoxy, or morpholinoethoxy substituent, then $R^2$ is not phenyl, methoxyphenyl, tert-butyl, or cyclopentyl;

when X is $CH_2$, $(CH_2)_2$, $COCH_2$, or $CH_2CO$, $A^1$ is hydrogen, and $R^1$ is phenyl, then $R^2$ is not phenyl; and when X is a covalent bond, p is 0, $A^1$ is hydrogen or methoxy, and $R^1$ is phenyl or phenyl substituted with a single chloro, fluoro, bromo, methoxy, pyrrolidinoethoxy, or piperidinoethoxy substituent, then $R^2$ is not phenyl or m-fluorophenyl.

In a preferred embodiment of the first aspect, $A^1$ is hydroxy; $A^2$, $A^3$, and $A^4$ are hydrogen; and p is 0.

In another preferred embodiment of the first aspect, $R^1$ is phenyl, pyridyl, $(C_1-C_4)$alkyl, adamantyl, naphthyl, or a partially saturated, fully saturated, or fully unsaturated five to six membered ring optionally having up to two heteroatoms selected independently from oxygen, sulfur, and nitrogen; wherein each of said $R^1$ groups is optionally substituted with up to seven fluoro atoms, or with up to three substituents independently selected from Group A.

In another preferred embodiment of the first aspect, $R^1$ is phenyl, cyclohexyl, pyridyl, thienyl, isopropyl, or adamantyl; wherein each of said $R^1$ groups is optionally substituted with up to seven fluoro atoms, or with up to three substituents independently selected from Group A.

In another preferred embodiment of the first aspect, $R^1$ is phenyl or cyclohexyl; wherein each of said $R^1$ groups is optionally substituted with up to seven fluoro atoms, or with up to three substituents independently selected from Group A.

In another preferred embodiment of the first aspect, each of said $R^1$ groups is substituted with up to three halo atoms, or with one substituent selected from hydroxy, $(C_1-C_2)$ alkoxy, pyrrolidino-$(C_1-C_4)$alkoxy, dimethylamino, $(C_2-C_4)$alkenyl-$COOR^7$, $COOR^7$, $(C_2-C_4)$alkenyl-$CONR^4R^5$ wherein $R^4$ and $R^5$ are independently hydrogen, $(C_1-C_4)$alkyl, hydroxy$(C_1-C_4)$alkyl, —$(CH_2CH_2-O-CH_3)$, or $(C_5-C_6)$cycloalkyl, or $R^4$ and $R^5$ taken together with the nitrogen atom to which they are attached form piperidino or morpholino, or $SO_2-R^6$ wherein $R^6$ is imidazolyl optionally substituted with up to three substituents independently selected from $(C_1-C_4)$alkyl.

In another preferred embodiment of the first aspect, each of said $R^1$ groups is substituted with up to three fluoro atoms, or with one substituent selected from iodo, chloro, bromo, hydroxy, methoxy, pyrrolidino-ethoxy, dimethylamino, $COOR^7$ wherein $R^7$ is hydrogen or methyl, or ethenyl-$CONR^4R^5$ wherein $R^4$ and $R^5$ are both methyl, or $R^4$ and $R^5$ taken together with the nitrogen atom to which they are attached form piperidino or morpholino.

In another preferred embodiment of the first aspect, each of said $R^1$ groups is substituted with one hydroxy or pyrrolidino-ethoxy.

In another preferred embodiment of the first aspect, X is a covalent bond, $CH_2$, $CH_2$-phenylene, $CO_2$, $CO-(C_0-C_2)$alkylene, or $SO_2-(C_0-C_2)$alkylene.

In another preferred embodiment of the first aspect, X is a covalent bond, $CO$, or $SO_2$.

In another preferred embodiment of the first aspect, $R^2$ is $(C_1-C_7)$alkyl; propenyl; a partially saturated, fully saturated, or fully unsaturated five to seven membered ring optionally having up to two heteroatoms selected independently from oxygen, sulfur, and nitrogen; a bicyclic ring consisting of two fused independently partially saturated, fully saturated, or fully unsaturated five to six membered rings, wherein said bicyclic ring includes up to two oxygen atoms; or biphenyl; wherein said $(C_1-C_7)$alkyl is optionally substituted with one to seven fluoro substituents, or up to three substituents independently selected from Group B; wherein said propenyl is optionally substituted with up to three substituents independently selected from Group C; and wherein each of said 5–7 membered ring, said bicyclic ring, and said biphenyl is optionally substituted with up to three substituents independently selected from Group D. In an even more preferred embodiment, each of said $(C_1-C_7)$alkyl and said propenyl is substituted with one to three fluoro substituents, or up to two substituents independently selected from amino and methylcarbonyl; and wherein each of said 5–7 membered ring, said bicyclic ring, and said biphenyl is substituted with up to three fluoro substituents, or up to two substituents independently selected from hydroxy, $(C_1-C_3)$ alkyl, amino, and methylcarbonyl.

In another preferred embodiment of the first aspect, $R^2$ is methyl, t-butyl, phenyl, cyclohexyl, isoxazolyl, tetrahydropyranyl, naphthyl, or benzodioxolyl; wherein each of said methyl or t-butyl is optionally substituted with one to seven fluoro substituents, or up to three substituents independently selected from Group B; and wherein each of said phenyl, cyclohexyl, isoxazolyl, tetrahydropyranyl, naphthyl, or benzodioxolyl is optionally substituted with up to three substituents independently selected from Group D.

In another preferred embodiment of the first aspect, $R^2$ is trifluoromethyl or phenyl; wherein said phenyl is optionally substituted with up to three substituents independently selected from Group D.

In another preferred embodiment of the first aspect, $A^1$ is hydroxy;

$A^2$, $A^3$, and $A^4$ are hydrogen;

p is 0;

$R^1$ is phenyl, cyclohexyl, pyridyl, thienyl, isopropyl, or adamantyl; wherein each of said $R^1$ groups is optionally substituted with up to three fluoro atoms, or with one substituent selected from iodo, chloro, bromo, hydroxy, methoxy, pyrrolidino-ethoxy, dimethylamino, $COOR^7$ wherein $R^7$ is hydrogen or methyl, or ethenyl-$CONR^4R^5$ wherein $R^4$ and $R^5$ are both methyl, or $R^4$ and $R^5$ taken together with the nitrogen atom to which they are attached form piperidino or morpholino;

X is a covalent bond, $CH_2$, $CH_2$-phenylene, $CO_2$, $CO-(C_0-C_2)$alkylene, or $SO_2-(C_0-C_2)$alkylene; and $R^2$ is methyl, t-butyl, phenyl, cyclohexyl, isoxazolyl, tetrahydropyranyl, naphthyl, or benzodioxolyl; wherein each of said methyl or t-butyl is optionally substituted with one to three fluoro substituents, or up to two substituents independently selected from amino and methylcarbonyl; and wherein each of said phenyl, cyclohexyl, isoxazolyl, tetrahydropyranyl, naphthyl, or benzodioxolyl is optionally substituted with up to three fluoro substituents, or up to two substituents independently selected from hydroxy, $(C_1-C_3)$alkyl, amino, and methylcarbonyl.

Some of the more preferred compounds of the first aspect of the present invention include 1-(4-hydroxy-phenyl)-2-phenyl-1,2,3,4-tetrahydroisoquinolin-6-ol; 3-[4-(6-hydroxy-2-phenyl-1,2,3,4-tetrahydroisoquinolin-1-yl)-phenyl]-1-piperidin-1-yl-propenone; 3-[4-(6-hydroxy-2-phenyl-1,2,3,4-tetrahydroisoquinolin-1-yl)-phenyl]-1-morpholin-4-yl-propenone; 3-[4-(6-hydroxy-2-phenyl-1,2,3,4-tetrahydroisoquinolin-1-yl)-phenyl]-N,N-dimethyl-acrylamide; 2-benzyl-1-[4-(2-pyrrolidin-1-yl-ethoxy)phenyl]-1,2,3,4-tetrahydroisoquinolin-6-ol; 2,2,2-trifluoro-1-[6-hydroxy-1-(4-hydroxyphenyl)-3,4-dihydro-1H-isoquinolin-2-yl]-ethanone; 2-benzenesulfonyl-1-[4-(2-pyrrolidin-1-yl-ethoxy)phenyl]-1,2,3,4-tetrahydroisoquinolin-6-ol; and 2-(4-isopropylbenzenesulfonyl)-1-[4-(2-pyrrolidin-1-yl-ethoxy)phenyl]-1,2,3,4-tetrahydroisoquinolin-6-ol.

In another preferred embodiment of the first aspect, said compound is of formula (I);

$A^1$ is hydroxy, $(C_1-C_4)$alkoxy, $(C_1-C_4)$alkanoyloxy, or pyrrolidino-ethoxy;

$A^2$, $A^3$, and $A^4$ are hydrogen;

p is 0 or 1;

$R^1$ is $(C_1-C_4)$alkyl, $(C_4-C_7)$cycloalkyl, adamantyl, phenyl, pyridyl, or thienyl, wherein each of said phenyl, pyridyl, or thienyl groups is optionally substituted with up to three fluoro atoms, or with one substituent selected from iodo, chloro, bromo, hydroxy, methoxy, dimethylamino, $OCH_2CH_2NR^8R^9$, $COOR^7$, ethenyl-$COOR^7$, or ethenyl-$CONR^4R^5$ wherein $R^4$ and $R^5$ are both methyl, or $R^4$ and $R^5$ taken together with the nitrogen atom to which they are attached form pyrrolidino, piperidino, hexamethyleneimino, or morpholino;

X is a covalent bond, $CH_2$, $CH_2$-phenylene, $CO_2$, CO—$(C_0-C_2)$alkylene, or $SO_2$—$(C_0-C_2)$alkylene; and $R^2$ is $(C_1-C_7)$alkyl, phenyl, benzyl, thienyl, $(C_5-C_7)$cycloalkyl, isoxazolyl, imidazolyl, tetrahydropyranyl, naphthyl, or benzodioxolyl, wherein said $(C_1-C_7)$alkyl is optionally substituted with one to three fluoro substituents, or up to two substituents independently selected from amino and methylcarbonyl, and wherein each of said phenyl, thienyl, $(C_5-C_7)$cycloalkyl, isoxazolyl, tetrahydropyranyl, naphthyl, and benzodioxolyl is optionally substituted with up to three fluoro substituents, or up to two substituents independently selected from hydroxy, methoxy, $(C_1-C_3)$alkyl, amino, and methylcarbonyl.

In another preferred embodiment of the first aspect, said compound is of formula (II).

In another preferred embodiment of the first aspect, said compound is of formula (II);

$A^1$ is hydroxy, $(C_1-C_4)$alkoxy, or $(C_1-C_4)$alkanoyloxy;

$A^2$, $A^3$, and $A^4$ are hydrogen;

p is 0 or 1;

$R^1$ is $(C_1-C_4)$alkyl, $(C_4-C_7)$cycloalkyl, adamantyl, phenyl, pyridyl, or thienyl, wherein each of said phenyl, pyridyl, thienyl, or $(C_5-C_7)$cycloalkyl groups is optionally substituted with up to three fluoro atoms, or with one substituent selected from iodo, chloro, bromo, hydroxy, methoxy, dimethylamino, $OCH_2CH_2NR^8R^9$, $COOR^7$, or ethenyl-$CONR^4R^5$ wherein $R^4$ and $R^5$ are both methyl, or $R^4$ and $R^5$ taken together with the nitrogen atom to which they are attached form pyrrolidino, piperidino, hexamethyleneimino, or morpholino;

X is a covalent bond, $CH_2$, $CH_2$-phenylene, $CO_2$, CO—$(C_0-C_2)$alkylene, or $SO_2$—$(C_0-C_2)$alkylene; and $R^2$ is $(C_1-C_7)$alkyl, phenyl, benzyl, thienyl, $(C_5-C_7)$cycloalkyl, isoxazolyl, tetrahydropyranyl, naphthyl, or benzodioxolyl, wherein said $(C_1-C_7)$alkyl is optionally substituted with one to three fluoro atoms, or up to two substituents independently selected from amino and methylcarbonyl, and wherein each of said phenyl, thienyl, cyclohexyl, isoxazolyl, tetrahydropyranyl, naphthyl, and benzodioxolyl is optionally substituted with up to three fluoro atoms, or up to two substituents independently selected from hydroxy, methoxy, and $(C_1-C_3)$alkyl.

One of the more preferred compounds of the first aspect of the present invention, wherein the compound is of formula (II) is 2,2,2-trifluoro-1-[7-hydroxy-4-(4-hydroxy-phenyl)-3,4-dihydro-1H-isoquinolin-2-yl]-ethanone.

In a second aspect, this invention provides compounds of the formula:

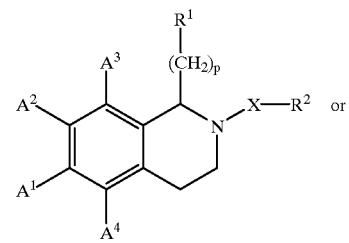

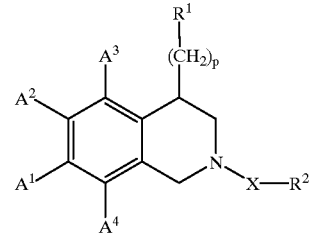

wherein:

$A^1$ is hydrogen, hydroxy, $(C_1-C_4)$alkoxy, or $(C_1-C_4)$alkanoyloxy, said $(C_1-C_4)$alkoxy or said $(C_1-C_4)$alkanoyloxy being optionally substituted by hydroxy, halo, or a partially saturated, fully saturated, or fully unsaturated five to twelve membered ring optionally having up to four heteroatoms independently selected from oxygen, sulfur, and nitrogen, or $A^1$ is $R^3$—$(C_1-C_4)$alkoxy wherein $R^3$ is pyrrolidino, piperidino, morpholino, or dimethylamino;

$A^2$, $A^3$, and $A^4$ are independently selected from hydrogen, hydroxy, $(C_1-C_4)$alkoxy, and halo;

$R^1$ is phenyl; pyridyl; piperidinyl; $(C_1-C_7)$alkyl; adamantyl; a partially saturated, fully saturated, or fully unsaturated three to twelve membered ring optionally having up to four heteroatoms selected independently from oxygen, sulfur, and nitrogen; a bicyclic ring consisting of two fused independently partially saturated, fully saturated, or fully unsaturated five to six membered rings, wherein said bicyclic ring includes up to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, wherein said bicyclic ring system includes up to four heteroatoms independently selected from oxygen, sulfur, and nitrogen; wherein each of the above $R^1$ groups is optionally substituted with up to seven fluoro atoms, or with up to three substituents independently selected from Group A, wherein Group A consists of hydroxy, halo, $(C_1-C_4)$alkyl, $(C_1-C_4)$alkoxy, $(C_3-C_8)$cycloalkyl, $R^3$—$(C_1-C_4)$alkoxy, $(C_2-C_4)$alkenyl-COOR$^7$ wherein $R^7$ is hydrogen or $(C_1-C_4)$alkyl, $(C_0-C_4)$alkyl-COOR$^7$, $(C_1-C_4)$alkanoyloxy-$(C_2-C_4)$alkenyl, $(C_2-C_4)$alkenyl-CONR$^4$R$^5$ wherein $R^4$ and $R^5$ are independently hydrogen, $(C_1-C_4)$alkyl, hydroxy $(C_1-C_4)$alkyl, $(C_1-C_4)$alkoxy-$(C_1-C_4)$alkylene, or $(C_3-C_8)$cycloalkyl, or $R^4$ and $R^5$ taken together with the nitrogen atom to which they are attached form pyrrolidino, piperidino, morpholino, or hexamethyleneimino, $(C_0-C_4)$alkyl-CONR$^4$R$^5$, $(C_0-C_4)$alkyl-NR$^4$R$^5$, OCH$_2$CH$_2$NR$^8$R$^9$ wherein $R^8$ and $R^9$ are independently methyl or ethyl, or $R^8$ and $R^9$ taken together with the nitrogen atom to which they are attached form pyrrolidino, piperidino, morpholino, or hexamethyleneimino, propyl-R$^8$R$^9$, and SO$_2$—R$^6$ wherein $R^6$ is imidazolyl, thienyl, benzathienyl, or isoxazyl, optionally substituted with up to three substituents independently selected from $(C_1-C_4)$alkyl;

X is $(C_0-C_1)$alkylene-phenylene-$(C_0-C_1)$alkylene, $CO_2$, CO, $(C_1-C_3)$alkylene-CO—$(C_1-C_3)$alkylene, $(C_0-C_3)$alkylene-CO—$(C_2-C_3)$ alkylene, $(C_2-C_3)$alkylene-CO—$(C_0-C_3)$alkylene, or $(C_0-C_4)$alkylene-SO$_2$—$(C_0-C_4)$alkylene;

$R^2$ is $(C_1-C_9)$alkyl; $(C_2-C_4)$alkenyl; benzhydryl; a partially saturated, fully saturated, or fully unsaturated three to eight membered ring optionally having up to four heteroatoms selected independently from oxygen, sulfur, and nitrogen; a bicyclic ring consisting of two fused independently partially saturated, fully saturated, or fully unsaturated five to six membered rings, wherein said bicyclic ring includes up to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, wherein said bicyclic ring system includes up to four heteroatoms independently selected from oxygen, sulfur, and nitrogen; wherein said $(C_1-C_9)$alkyl is optionally substituted with one to seven fluoro substituents, or up to three substituents independently selected from Group B, wherein Group B consists of chloro, $(C_1-C_4)$alkoxy, amino, and $(C_1-C_4)$alkylcarbonyl; wherein said $(C_2-C_4)$alkenyl is optionally substituted with up to three substituents independently selected from Group C, wherein Group C consists of halo, $(C_1-C_4)$alkoxy, amino, and $(C_1-C_4)$alkylcarbonyl; and wherein said benzhydryl, said 5 to 8 membered ring, said bicyclic ring, and said bicyclic ring system is optionally substituted with up to three substituents independently selected from Group D, wherein Group D consists of halo, hydroxy, $(C_1-C_4)$alkyl, $(C_1-C_4)$alkoxy, imidazolyl, amino, $(C_1-C_4)$alkylcarbonylamino, and $(C_1-C_4)$alkylcarbonyl; and p is 0, 1, or 2.

In a third aspect, this invention provides methods for treating or preventing a disease, disorder, condition, or symptom mediated by an estrogen receptor and/or caused by lowered estrogen level in a mammal, said method comprising administering to said mammal a therapeutically effective amount of a compound of the present invention.

In preferred embodiments of the third aspect, a therapeutically effective amount of a compound of the present invention is combined with a therapeutically effective amount of an anabolic agent, a prodrug thereof, or a pharmaceutically acceptable salt of said anabolic agent or said prodrug; a growth hormone or a growth hormone secretagogue, a prodrug thereof, or a pharmaceutically acceptable salt of said growth hormone secretagogue or said prodrug; a prostaglandin agonist/antagonist, a prodrug thereof, or a pharmaceutically acceptable salt of said prostaglandin agonist/antagonist or said prodrug; or a parathyroid hormone or sodium fluoride.

In another preferred embodiment of the third aspect, said disease, disorder, condition, or symptom is perimenopausal or postmenopausal syndrome, osteoporosis, atrophy of skin or vagina, elevated serum cholesterol levels, cardiovascular disease, Alzheimer's disease, a reduction or prevention of reduction in cognitive function, an estrogen dependent cancer, breast or uterus cancer, a prostatic disease, benign prostatic hyperplasia, or prostate cancer.

In another preferred embodiment of the third aspect, said disease, disorder, condition, or symptom is obesity, endometriosis, bone loss, uterine fibrosis, aortal smooth muscle cell proliferation, lack of birth control, acne, hirsutism, dysfunctional uterine bleeding, dysmenorrehea, male infertility, impotence, psychological and behavioral symptoms during menstruation, ulcerative mucositis, uterine fibroid disease, restenosis, atherosclerosis, musculoaponeurotic fibromatosis, alopecia, wound-healing, scarring, auto immune disease, cartilage degeneration, delayed puberty, demyelinating disease, dysmyelinating disease, hypoglycemia, lupus erythematosus, myocardial infarction, ischemia, thromboembolic disorder, obessive compulsive disorder, ovarian dysgenesis, post menopausal CNS disorder, pulmonary hypertension, reperfusion damage, resistant neoplasm, rheumatoid arthritis, seborrhea, sexual precocity, thyroiditis, Turner's syndrome, or hyperlipidemia.

In another preferred embodiment of the third aspect, said method is useful for blocking a calcium channel, inhibiting an environmental estrogen, minimizing the uterotropic effect of tamoxifen or an analog thereof, removing fibrin by inhibiting plasminogen activators, inhibiting estrogen positive primary tumors of the brain and CNS, increasing sphincter competence, increasing libido, inhibiting fertility, oxidizing low density lipoprotein, increasing macrophage function, expressing thrombomodulin, or increasing levels of endogenous growth hormone.

In a fourth aspect, this invention provides pharmaceutical compositions comprising a compound of the present invention and a pharmaceutically acceptable vehicle, carrier, or diluent.

In a fifth aspect, this invention provides kits useful for treating or preventing a disease, disorder, condition, or symptom mediated by an estrogen receptor and/or caused by lowered estrogen levels, said kit comprising a compound of the present invention and a pharmaceutically acceptable vehicle, carrier, or diluent in a dosage form, and a container for containing said dosage form.

In a preferred embodiment of the fifth aspect, said kit also comprises an anabolic agent, a prodrug thereof, or a pharmaceutically acceptable salt of said anabolic agent or said prodrug; a growth hormone or a growth hormone secretagogue, a prodrug thereof, or a pharmaceutically acceptable salt of said growth hormone secretagogue or said prodrug; a prostaglandin agonist/antagonist, a prodrug thereof, or a pharmaceutically acceptable salt of said prostaglandin agonist/antagonist or said prodrug; or a parathyroid hormone or sodium fluoride.

DETAILED DESCRIPTION OF THE INVENTION

Halo or halogen refers to chloro, bromo, iodo and fluoro.

Estrogen agonists are herein defined as chemical compounds capable of binding to estrogen receptor sites in mammalian tissue and mimicking the action(s) of estrogen in one or more tissues.

Estrogen antagonists are herein defined as chemical compounds capable of binding to estrogen receptor sites in mammalian tissue and blocking the action(s) of estrogen or estrogen agonists in one or more tissues.

As used in this application, prostatic disease means benign prostatic hyperplasia or prostatic carcinoma.

A "compound", when used to refer to compounds of the present invention, includes within its scope not just the specific compound(s) listed or described, but also alternative forms of the compound, such as prodrugs, pharmaceutically acceptable salts, pharmaceutically acceptable salts of the prodrug, solvates, hydrates, and the like.

A prodrug is a chemical compound that, in its present form, has little or reduced pharmaceutical activity, but which, upon introduction into its biological environment, is readily converted into an active drug form. An exemplary prodrug is an ester of a drug, where upon introduction into a patient, the ester is cleaved to produce the active drug.

A "therapeutically effective amount" of a compound is an amount that is sufficient to cure, prevent, or alleviate a disease, disorder, condition, or symptom.

An "anabolic agent" is any compound that is capable of promoting synthetic metabolic reactions in a patient. In a preferred embodiment, anabolic agents are useful in promoting wound healing.

A "growth hormone or growth hormone secretagogue" is a naturally occurring growth hormone as understood by those skilled in the art, a compound that mimics one or more actions of a naturally occurring growth hormone, or a compound that stimulates the release of naturally occurring growth hormone in a patient.

A "prostaglandin agonist or antagonist" is any compound that is capable of agonizing or antagonizing the activity of a prostaglandin in a patient.

Those of skill in the art will recognize that certain substituents listed in this invention will be chemically incompatible with one another or with the heteroatoms in the compounds, and will avoid these incompatibilities in selecting compounds of this invention. Likewise, certain functional groups may require protecting groups during synthetic procedures as will be recognized by those of skill in the art.

Those of skill in the art will also recognize that certain compounds of this invention will consist of multiple possible geometric configurations, or isomers. All such isomers are included in this invention.

The pharmaceutical compositions and methods of this invention comprise, as an active ingredient, a compound of formula I or II. The pharmaceutically acceptable salts of the compounds of formula I and II are salts of non-toxic type commonly used, such as salts with organic acids (e.g., formic, acetic, trifluoroacetic, citric, maleic, tartaric, methanesulfonic, benzenesulfonic, toluenesulfonic acids, and the like), inorganic acids (e.g. hydrochloric, hydrobromic, sulfuric, phosphoric acids, and the like), amino acids (e.g., aspartic acid, glutamic acid, and the like), alkali metals (e.g., sodium, potassium, and the like), and alkaline earth metals (e.g., calcium, magnesium, and the like). These salts may be prepared by methods known to those of skill in the art.

The compounds of this invention may be administered to animals (including humans) orally, parenterally, topically, or otherwise, in any conventional form of preparation, such as capsules, microcapsules, tablets, granules, powder, troches, pills, suppositories, injections, suspensions, syrups, and the like.

The pharmaceutical compositions of this invention can be prepared by methods commonly employed using conventional additives, such as excipients (e.g., sucrose, starch, mannitol, sorbitol, lactose, glucose, cellulose, talc, calcium phosphate, calcium carbonate, and the like), binders (e.g., cellulose, methylcellulose, hydroxymethylcellulose, polypropylpyrrolidone, polyvinylprrolidone, gelatin, gum arabic, polyethyleneglycol, sucrose, starch, and the like), disintegrators (e.g., starch, carboxymethylcellulose, hydroxypropylstarch, low substituted hydroxypropylcellulose, sodium bicarbonate, calcium phosphate, calcium citrate, and the like), lubricants (e.g., magnesium stearate, light anhydrous silicic acid, talc, sodium lauryl sulfate, and the like), flavoring agents (e.g., citric acid, menthol, glycine, orange powder, and the like), preservatives (e.g., sodium benzoate, sodium bisulfite, methylparaben, propylparaben, and the like), stabilizers (e.g., citric acid, sodium citrate, acetic acid, and the like), suspending agents (e.g., methylcellulose, polyvinylpyrrolidone, aluminum stearate, and the like), dispersing agents (e.g., hydroxypropylmethylcellulose and the like), diluents (e.g., water, alcohol, glycerin, and the like), and base waxes (e.g., cocoa butter, white petrolatum, polyethylene glycol, and the like).

The compounds of this invention may be administered once a day or in multiple daily doses, with a preferred daily dosage of about 0.001 to about 100 mg in adult human patients. This dosage may be properly varied depending on the age, body weight, and medical condition of the patient, as well as the mode of administration. A more preferred daily dose is about 1.0 to about 10 mg in human patients. One dose per day is preferred. Controlled release, sustained release, and/or delayed release oral or parenteral compositions may be used.

General Reaction Schemes

Compounds of this invention are readily prepared by the reactions illustrated in the schemes below.

If required in the following processes, active groups may be protected with a suitable protecting group such as benzyl, p-toluenesulfonyl, methyl, p-methoxybenzyl, and the like, and the protecting group may subsequently be removed at a later stage in the synthesis. The protection and removal of the protecting groups may be carried out according to procedures known to those skilled in the art (e.g., procedures disclosed in *Protective Groups in Organic Synthesis* by T. W. Greene, published by John Wiley & Sons (1991)).

General Reaction Scheme A

A compound of formula (Ia) (i.e., a compound of formula (I) wherein X is CO—(CH$_2$)$_y$, and y is 0–3) may be prepared according to the procedures illustrated in Scheme A.

The reduction of compound (VI) to compound (VII) is typically carried out in the presence of sodium borohydride in a reaction inert solvent such as methanol or tetrahydrofuran, at from about 0° C. to about room Scheme A

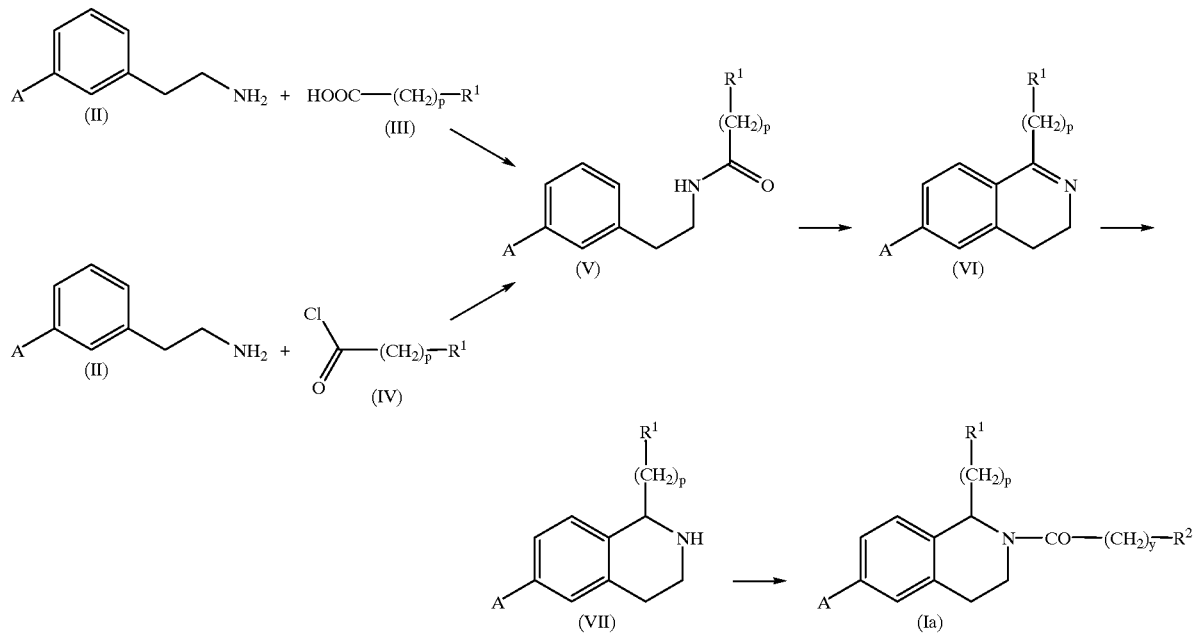

As illustrated in Scheme A, a phenethyl amine of formula (II) is coupled with a carboxylic acid of formula (III) to give the benzamide of formula (V). Compound (V) is subjected to cyclodehydration to give the dihydroisoquinoline of formula (VI). Dihydroisoquinoline (VI) is reduced to the tetrahydroisoquinoline of formula (VII). Then, compound (VII) may be reacted with a desired acid anhydride, acid chloride, or other coupling agent to give compound (Ia). Alternatively, compound (VII) may be reacted with a desired acid in the presence of 1-propanephosphonic acid cyclic anhydride, Et$_3$N, and DMAP in dichloromethane (CH$_2$Cl$_2$) to yield compound (Ia).

The coupling of compounds (II) and (III) is carried out in the presence of a coupling agent for peptide synthesis, preferably with an additive. Suitable coupling agents include water-soluble diimides such as N-cyclohexyl-N'-(4-diethylaminocyclohexyl)-carbodiimide and 1-(3-dimethylaminopropyl)-3-ethylcarbodiimide (EDC), and suitable additives include 1-hydroxybenzotriazole (HOBt) and 3-hydroxy-4-oxo-3,4-dihydro-1,2,3-benzotriazine. This reaction mixture is preferably stirred at a temperature between about 0° C. to room temperature (i.e., about 25° C.), for about 12 to 60 hours in a reaction inert solvent such as CH$_2$Cl$_2$, preferably under nitrogen.

Cyclodehydration of the intermediate compound (V) is carried out in a reaction inert solvent such as 1,2-dichloroethane in the presence of phosphorus pentachloride under nitrogen, or neat using phosphorus oxychloride under nitrogen. Phosphorus pentachloride is added to the solution of compound (V) at about 0° C., then the reaction mixture is refluxed for about 1 to 24 hours. The reaction of compound (V) and phosphorus oxychloride is carried out at about the reflux temperature of the reaction mixture for about 1 to 48 hours.

temperature, for about 1 to 12 hours, preferably under nitrogen. The reaction is quenched with water.

The intermediate compound (VII) thus obtained is reacted with a desired acid anhydride or acid chloride to yield compound (Ia) according to amide formation procedures known to those skilled in the art. This reaction is performed in the presence of a base such as triethylamine (Et$_3$N), in a reaction inert solvent such as CH$_2$Cl$_2$, for about 1 to 72 hours, at about 0° C. to about room temperature. This reaction is preferably performed under nitrogen.

Alternatively, compound (V) may be prepared by reacting compound (II) with an acyl chloride of formula (IV) in the presence of a base such as triethylamine in a reaction inert solvent. Suitable solvents include dichloromethane, tetrahydrofuran (THF), CHCl$_3$, 1,2-dichloroethane, dioxane, toluene, benzene, and the like, with THF being the most preferred. This reaction is preferably carried out at a temperature of about 0° C. to 30° C., most preferably about 25° C., under nitrogen, for about 1 to 24 hours, preferably about 12 hours. If required, a catalyst such as 4-(dimethylamino) pyridine, scandium triflate, tributyl phosphine, or the like may be added to the reaction mixture.

Intermediate compound (VI) may be substituted with a desired substituent on R$^1$ and subsequently subjected to the remaining processes illustrated in Scheme A. This substitution reaction is performed according to procedures known to those skilled in the art. For example, compound (VI) wherein R$^1$ is piperidin-4-yl may be reacted with a heteroaryl sulfonyl chloride in the presence of a base such as triethylamine in a reaction inert solvent such as dichloroethane to yield a sulfonamide. This reaction is preferably carried out at about room temperature, under nitrogen, for about 1 to 24 hours, preferably about 2 to 20 hours.

A compound of formula (I) of this invention wherein X is —(CH$_2$)$_z$—SO$_2$— may be prepared by reacting compound (VII) with a sulfonyl chloride of formula $R^2$—$(CH_2)_z$—$SO_2$—Cl according to known procedures. For example, this reaction may be carried out in the presence of triethylamine in a reaction inert solvent such as tetrahydrofuran (THF) at about room temperature for about 1 to 24 hours under nitrogen.

A compound of formula (I) of this invention wherein X is a covalent bond, $(CH_2)_n$, or $(CH_2)_x$-phenyl (wherein x is 0 or 1), may also be prepared by reacting compound (VII) with an aldehyde of formula $R^2$—X—CHO according to known procedures. This reaction is typically performed in the presence of a reducing agent such as sodium cyanoborohydride in a suitable solvent such as methanol.

A compound of formula (I) of this invention wherein X is $CO_2$ may be prepared by reacting compound (VII) with either a dicarbonate of formula $(R^2OCO)_2O$ or a chloroformate of formula $R^2OCOCl$ in the presence of a base such as triethylamine in a suitable solvent such as THF at about room temperature for about 1 to 24 hours, preferably under nitrogen.

General Reaction Scheme B

A compound of formula (Ib) (i.e., a compound of formula (I) wherein X is a covalent bond and $R^2$ is an optionally substituted ring moiety) may be prepared according to the procedures illustrated in Scheme B.

Scheme B

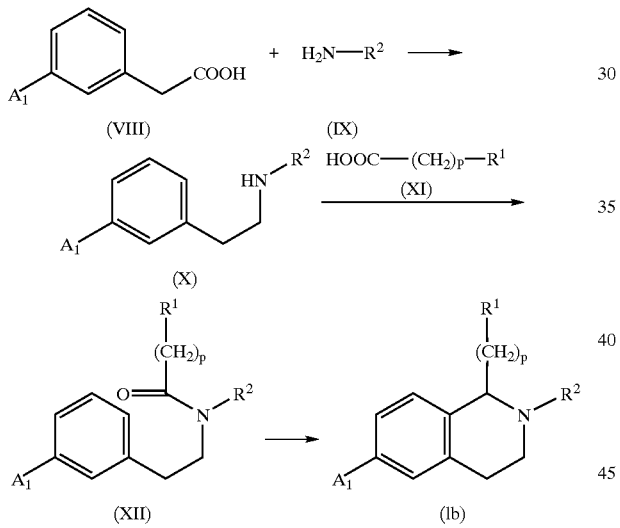

A benzyl acid of formula (VIII) is reacted with an amine of formula (IX) to give an amide, which is then reduced (this step not shown) to give the phenethyl amine of formula (X) according to known procedures (see, for example, Nagarajan et al., *Ind. J. Chem.*, 24B:83–97 (1985)). Compound (X) thus obtained is reacted with a carboxylic acid of formula (XI) to give the benzamide of formula (XII). The compound of formula (XII) is subjected to cyclodehydration followed by reduction, preferably with $NaBH_4$ in methanol, to give the tetrahydroisoquinoline (Ib).

The reaction of compound (X) with compound (XI) is carried out in the presence a base such as triethylamine, in a reaction inert solvent such as dichloromethane, THF, $CHCl_3$, or dioxane, preferably in the presence of a coupling agent such as 1-propanephosphonic acid cyclic anhydride (PPAA), EDC, or a mixture thereof, and a catalytic amount of an additive such as HOBt or 4-dimethylaminopyridine (DMAP), at about 0° C. to room temperature for about 1 to 36 hours.

The cyclodehydration of compound (XII) may be carried out according to procedures analogous to those described for in Scheme A.

Alternatively, compound (X) may be reacted with an acyl chloride of formula (IV) to give an amide (XII). This reaction may be performed according to procedures analogous to those described in Scheme A.

Compound (XI) may be substituted at its $R^1$ moiety with a desired substituent. For example, when $R^1$ is aryl aldehyde, compound (XI) is coupled with a carboalkoxytriphenylphosphorane in the presence of a base such as sodium hydroxide in a reaction inert solvent such as tetrahydrofuran (THF). This reaction is performed at about room temperature for about 1 to 12 hours.

General Reaction Scheme C

Scheme C illustrates methods to produce a compound of formula (Ic), namely a compound of formula (I) wherein $A_1$ is hydroxy and X is a covalent bond, $(CH_2)_n$, or $(CH_2)_x$-phenyl (wherein x is 0 or 1), starting from a compound of formula (Ia). In this scheme, "Pro" is a hydroxy protecting group.

Scheme C

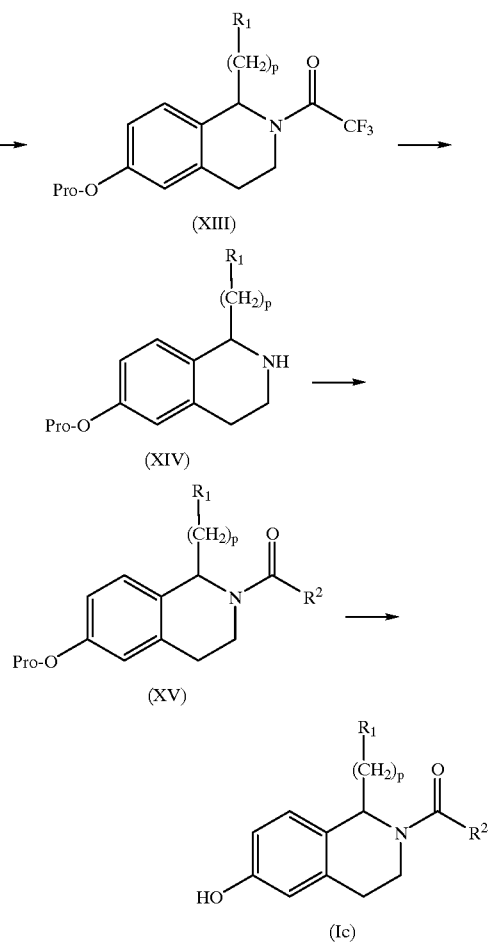

For example, compound (Ia) wherein $A_1$ is hydroxy, X is CO, and $R^2$ is $CF_3$ is first protected with a suitable hydroxy protecting group to obtain the compound of formula (XIII), which is converted to the compound of formula (XIV), which is coupled with a suitable acyl chloride of formula $R^2COCl$ to obtain the compound of formula (XV), which is finally deprotected to yield the desired compound (Ic).

While any hydroxy protecting groups known to those skilled in the art may be used to protect compound (Ia), a benzyl or methyl group is preferably used. The protection is typically carried out by reacting compound (Ia) wherein $A^1$ is hydroxy with benzyl bromide in the presence of sodium hydride in a reaction inert solvent such as DMF at about 0° C. to 100° C. under nitrogen for about 1 to 12 hours, preferably about 4 hours.

Conversion of compound (XIII) is performed according to known procedures. This conversion is conveniently carried out in the presence of an inorganic base such as $K_2CO_3$, in a reaction inert solvent such as methanol or ethanol under $N_2$ for about 1 to 24 hours, preferably about 12 to 24 hours.

The coupling reaction of compound (XIV) with a desired acyl chloride of formula $R^2COCl$ is preferably performed in the presence of triethylamine in THF at about room temperature under nitrogen for about 1 to 24 hours.

The hydroxy protecting group of compound (XV) may be removed by known procedures. For example, this reaction may be performed in the presence of a source of $H_2$ and a catalyst such as 20% $Pd(OH)_2/C$, in a reaction inert solvent such as methanol, under nitrogen, at about the reflux temperature of the reaction mixture for about 1 to 4 hours.

Compound (I) wherein $R^1$ is aryl substituted by an alkenylamide group may be obtained by reacting compound (I) wherein $R^1$ is iodophenyl with a suitable alkenylamide. This reaction may be performed in the presence of a catalyst such as $Pd(PPh_3)_4$ and a base such as triethylamine in a reaction inert solvent such as N,N-dimethylformamide (DMF) at about 60° C. to 100° C. for about 1 to 12 hours. The alkenylamide may be prepared by known methods, for example, by reacting a secondary amine with an acyl halide such as acryloyl chloride. This reaction is performed in the presence of a base such as triethylamine in a reaction inert solvent such as dichloroethane at about room temperature for about 1 to 12 hours.

Compound (I) wherein $A_1$ is hydroxy may be obtained by converting compound (Ia) wherein $A_1$ is methoxy. This conversion is performed in the presence of boron tribromide in a suitable solvent such as dichloromethane at about −78° C. to room temperature under nitrogen for about 1 to 12 hours. If required, this conversion may be quenched by adding a suitable solvent such as methanol.

The hydroxy group at the 6-position of the tetrahydroisoquinoline ring of compound (I) may be converted into an optionally substituted ($C_1$–$C_4$ alkyl)—CO. For example, the hydroxy may be coupled with 1-(2-chloroethyl)pyrrolidine hydrochloride in the presence of a condensing agent such as sodium hydride in a reaction inert solvent such as DMF. This reaction is preferably performed at about room temperature to the reflux temperature of the reaction mixture, more preferably at about 100° C., under nitrogen, for about 1 to 8 hours, preferably about 4 to 5 hours.

A substituent attached to a ring moiety of $R^1$ of compound (I) may be converted to another substituent. For example, the hydroxy substituent on the $R^1$ ring moiety may be converted to 2-pyrrolidin-1-yl-ethoxy according to procedures analogous to those for the coupling reaction of hydroxy at the 6-position of the tetrahydroisoquinoline ring of compound (I) with 1-(2-chloroethyl)pyrrolidine hydrochloride.

Compounds (II), (III), (IV), (VIII), (IX) and (XI) are known compounds and are readily prepared according to procedures well known to those skilled in the art.

General Reaction Scheme D

A compound of formula (XXI) (i.e., a compound of formula (II) lacking the $R^2$ group) may be prepared according to the procedures illustrated in Scheme D.

Scheme D

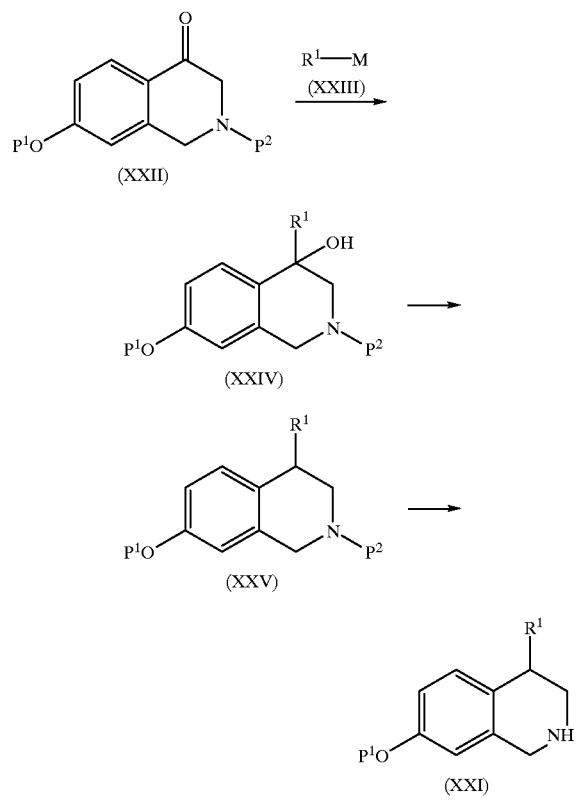

Compounds of formula (XXI) can be prepared under standard reaction conditions analogous to those well known in the art (e.g., Grethe et al., *J. Org. Chem.*, 33(2):491 (1968)). For example a suitably protected dihydro-1H-isoquinolin-4-one of formula (XXII) can be treated with a nucleophile of formula (XXIII) such as substituted phenyl lithium to give the alcohol of formula (XXIV). The reaction is typically run in an inert solvent such as THF, 1,2 dimethoxyethane, or diethyl ether, and a temperature range of −78° C. to room temperature is preferred.

The alcohol (XXIV) can be reduced to the tetrahydroisoquinoline of formula (XXV) under suitable conditions (e.g., hydrogenation over a metal catalyst such as palladium). Another option for the reaction is to perform the reduction with a trialkylsilane in the presence of a strong acid such as trifluoroacetic acid. The reaction is typically run in an inert solvent at a temperature range of 0° C. to 60° C.

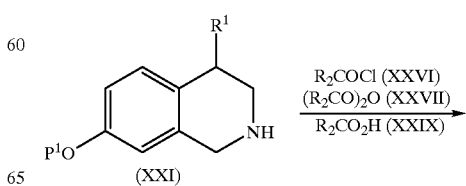

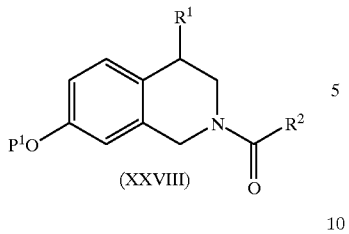

(XXVIII)

The compounds of formula (XXI) can be treated with an acid chloride of formula (XXVI) or an acid anhydride of formula (XXVII) in the presence a tertiary amine base such as triethylamine or DMAP to give an amide of formula (XXVIII). The acid chlorides of formula (XXVI) and acid anhydride of formula (XXVII) are commercially available or can be prepared from carboxylic acids by procedures known to those skilled in the art.

Another synthetic route for preparing the compounds of formula (XXVIII) involves treating a compound of formula (XXI), preferably at room temperature, with a carboxylic acid of formula (XXIX) in the presence of a coupling agent (e.g., dicyclohexylcarbodiimide (DCC), 1-(3'-dimethylaminopropyl)-3-ethylcarbodiimide (EDC), or 1-propanephosphonic acid cyclic anhydride (PPAA)) and a suitable base (e.g., triethylamine, DMAP, or N-methylmorpholine (NMO)) in a solvent such as dichloromethane, chloroform, or dimethylformamide. Optionally, agents such as HOBt maybe added to the reaction.

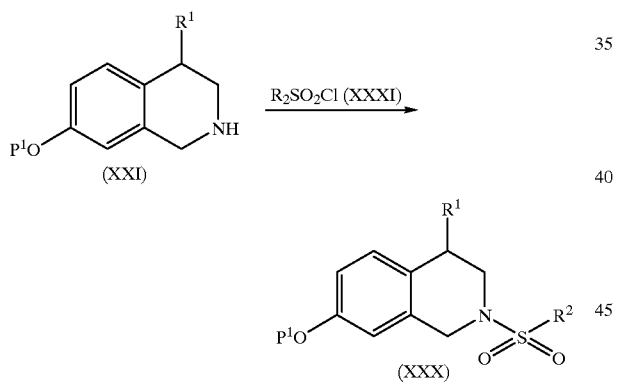

Compounds of formula (XXX) can be prepared by reacting the amines of formula (XXI) with a sulfonyl chloride of formula (XXXI) in the presence of a base such as triethylamine, DMAP, or NMO in a suitable solvent such as dichloromethane, chloroform, or dimethylformamide. The reactions can be run in temperature range of −20° C. to 60° C., though room temperature is preferred.

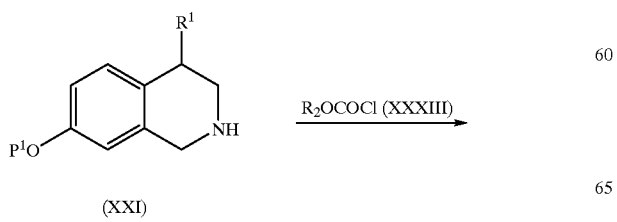

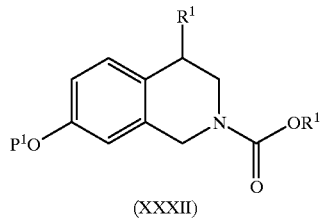

(XXXII)

Compounds of formula (XXXII) can be prepared by reacting the amines of formula (XXI) with a chloroformate of formula (XXXIII) in the presence of a base such as triethylamine, DMAP, NMO, or sodium hydrogen carbonate in a suitable solvent such as dichloromethane, chloroform, aqueous or anhydrous tetrahydrofuran, or dimethylformamide. The reaction can be run at 0° C. to 60° C., though room temperature is preferred.

General Reaction Scheme E

A compound of formula (XXI) (i.e., a compound of formula (II) lacking the $R^2$ group) may also be prepared according to the procedures illustrated in Scheme E.

Scheme E

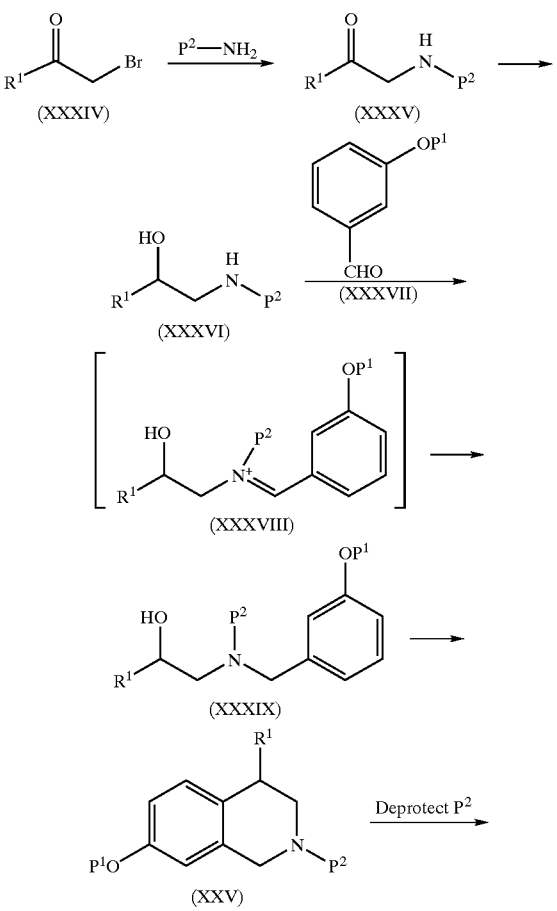

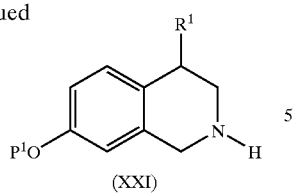

(XXI)

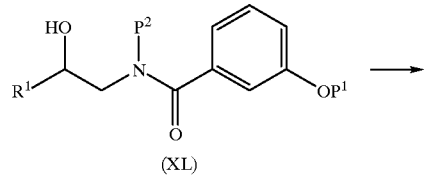

(XL)

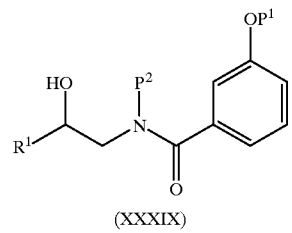

(XXXIX)

An alternative and more preferable synthesis of compounds of formula (XXI) involves reacting an alpha halogenated ketone of formula (XXXIV) with a suitably protected ammonia equivalent, preferably benzylamine, to give an amino-ketone of formula (XXXV). It will be obvious to anyone skilled in the art that the order of some of the next steps may be reversed. The compound of formula (XXXV) can be reduced with a suitable reducing agent, preferably sodium borohydride, di-isobutyl aluminum hydride (DIBAL-H), or lithium aluminum hydride in a suitable solvent. Typically, sodium borohydride reactions are run in protic solvents such as methanol or ethanol, in the temperature range of −10° C. to 40° C. (but preferably at about 0° C.), and the DIBAL-H or lithium aluminum hydride reactions are preferably run in dichloromethane or THF in the temperature range of −78° C. to 30° C. (preferably at about 0° C.) to give the amino alcohol of formula (XXXVI). In the next step, the amino alcohol of formula (XXXVI) is condensed with an aldehyde of formula (XXXVII) to give initially an iminium salt of formula (XXXVIII). The iminium salt of formula (XXXVIII) is reduced in situ with a reducing agent such as sodium borohydride, sodium cyanoborohydride, or sodium triacetoxyborohydride in a solvent such as dichloromethane, chloroform, 1,2 dichloroethane, methanol, or ethanol to give the amino alcohol of formula (XXXIX). For the latter reduction reaction, a temperature range of −10° C. to 50° C. can be employed but a temperature of about 0° C. is preferred.

The amino alcohol of formula (XXXIX) can be cyclodehyrated in the presence of a strong acid such as sulfuric acid or trifluoroacetic acid in a solvent such as dichloromethane, chloroform, or 1,2 dichloroethane in a temperature range of 0° C. to 60° C. to give (after appropriate deprotection) the tetrahydroisoquinoline of formula (XXI).

General Reaction Scheme F

A compound of formula (XXIX) (i.e., the amino alcohol intermediary shown in Scheme E) may be prepared according to the alterntive procedures illustrated in Scheme F.

Scheme F

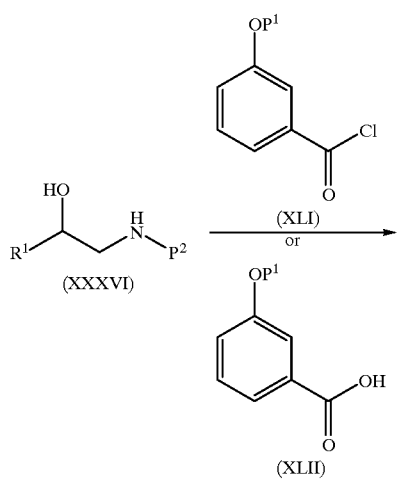

Another option for the synthesis of amino alcohol of formula (XXXIX) is via the amide of formula (XL), which can be prepared by methods known to those of ordinary skill from the amino alcohol (XXXVI). Such methods may include taking the amino-alcohol of formula (XXXVI) and treating this with an acid chloride of formula (XLI) in the presence of a tertiary amine base such as triethylamine or DMAP. The acid chlorides of formula (XLI) are commercially available or can be prepared from carboxylic acids by procedures known to those of ordinary skill in the art. Another method of preparing the amides of formula (XL) involves treating an amino alcohol of formula (XXXVI) with a carboxylic acid of formula (XLII) in the presence of a coupling agent (e.g., DCC, EDC, or PPAA) and a suitable base (e.g., triethylamine, DMAP, or NMO) in a solvent such as dichloromethane, chloroform, or dimethylformamide. Optionally, agents such as HOBt maybe added to the reaction. Typically, the reaction is run in the temperature range of 0° C. to 50° C., with room temperature being preferred.

The amides of formula (XL) can then be reduced to an amino-alcohol of formula (XXXIX) by reaction with a reducing agent such as lithium aluminum hydride or borane in a suitable solvent such as tetrahydrofuran or 1,2 dimethoxyethane at −10° C. to 100° C. (with 0° C. being preferred).

Reactive groups not involved in the above processes can be protected with standard protecting groups during the reactions and removed by standard procedures (Greene & Wuts, Protecting Groups in Organic Synthesis, John Wiley and Sons, Inc., Interscience, 2nd edition, New York) known to those of ordinary skill in the art. Presently preferred protecting groups include methyl and benzyl for the hydroxyl moiety, and trifluoroacetamide and benzyl for the amino moiety.

In each of the general reaction schemes discussed or illustrated above, pressure is not critical unless otherwise indicated. Pressures from about 0.5 atmospheres (~50,000 Pa) to about 5 atmospheres (~500,000 Pa) are generally acceptable, and ambient pressure, i.e. about 1 atmosphere (~100,000 Pa), is preferred as a matter of convenience.

The compounds of this invention may be prepared in racemic form and be resolved into their component enantiomers by standard techniques such as fractional crystallization or preparative chromatography. Alternatively, enantiomers of the invention compounds may be synthesized from the appropriate optically active intermediates or starting materials using any of the general processes described herein.

Further, optically active compounds of this invention may be prepared using enantioselective reactions or by resolution techniques such as the preparation of diastereomers by reacting the racemic material with an optically active reagent.

The compounds of this invention are valuable estrogen agonists or antagonists, and thus valuable pharmaceutical agents. Those that are estrogen agonists are useful for oral contraception, relief of the symptoms of menopause, prevention of threatened or habitual abortion, relief of dysmenorrhea, relief of dysfunctional uterine bleeding, relief of endometriosis, an aid in ovarian development, treatment of acne, diminution of excessive growth of body hair in women (hirsutism), the prevention and/or treatment of cardiovascular disease, prevention and treatment of atherosclerosis, prevention and treatment of osteoporosis, treatment of benign prostatic hyperplasia and prostatic carcinoma, obesity, and suppression of post-partum lactation. These agents also have a beneficial effect on plasma lipid levels and as such are useful in treating and/or preventing hypercholesterolemia.

While the compounds of this invention are typically estrogen agonists in bone, unexpectedly they are also often antiestrogens in breast tissue and as such would be useful in the treatment and prevention of breast cancer.

While the compounds of this invention are expected to be sufficiently active if administered separately, in many instances it will be beneficial to combine these compounds with other compounds in order to even more effectively treat a disease or condition. Exemplary categories of compounds which will be beneficial in combination with the compounds of the present invention include an anabolic agent, a prodrug thereof, or a pharmaceutically acceptable salt of said anabolic agent or said prodrug; a growth hormone or a growth hormone secretagogue, a prodrug thereof, or a pharmaceutically acceptable salt of said growth hormone secretagogue or said prodrug; a prostaglandin agonist/antagonist, a prodrug thereof, or a pharmaceutically acceptable salt of said prostaglandin agonist/antagonist or said prodrug; or a parathyroid hormone or sodium fluoride.

It will also be useful to present the compounds of the present invention in the form of kits useful for treating or preventing a disease, disorder, condition, or symptom mediated by an estrogen receptor and/or caused by lowered estrogen levels, said kit comprising a compound of the present invention and a pharmaceutically acceptable vehicle, carrier, or diluent in a dosage form, and a container for containing said dosage form.

In many instances, it will be preferable for the kit to include, in addition to a compound of the present invention, an anabolic agent, a prodrug thereof, or a pharmaceutically acceptable salt of said anabolic agent or said prodrug; a growth hormone or a growth hormone secretagogue, a prodrug thereof, or a pharmaceutically acceptable salt of said growth hormone secretagogue or said prodrug; a prostaglandin agonist/antagonist, a prodrug thereof, or a pharmaceutically acceptable salt of said prostaglandin agonist/antagonist or said prodrug; or a parathyroid hormone or sodium fluoride.

Methods for Testing the Activity of Invention Compounds
Assay 1: Control and Prevention of Endometriosis A preferred protocol for surgically inducing endometriosis is that described by Jones, Acta Endoerinol (Copenh), 106:282–88 (1984). Adult Charles River Sprague-Dawley CD® female rats (200–240 g) are used. An oblique ventral incision is made through the skin and musculature of the body wall. A segment of the right uterine horn is excised, the myometrium is separated from the endometrium, and the segment is cut longitudinally. A 5×5 mm section of the endometrium, with the epithelial lining apposed to the body wall, is sutured at its four corners to the muscle using polyester braid (Ethiflex, 7-0®). The criterion of a viable graft is the accumulation of fluid similar to that which occurs in the uterus as a result of estrogen stimulation.

Three weeks after transplantation of the endometrial tissue (+3 weeks) the animals are laparotomized, the volume of the explant (length×width×height) in mm is measured with calipers, and treatment is begun. The animals are injected sc for 3 weeks with 10 to 1000 mg/kg/day of a test compound according to the present invention. Control animals bearing endometrial explants are injected sc with 0.1 ml/day of corn oil for 3 weeks. At the end of the 3 week treatment period (+6 weeks), the animals are laparotomized and the volume of the explant determined. Eight weeks after cessation of treatment (+14 weeks) the animals are sacrificed and the explants are measured again. Statistical analysis of the explant volume is by an analysis of variance.

Assay 2: Effect on Prostate Weight

Three-month-old male Sprague-Dawley rats are administered by subcutaneous injection control vehicle (10% ethanol in water), estradiol (30 $\mu$g/kg), testosterone (1 mg/kg), or a test compound according to the present invention daily for 14 days (n=6/group). After 14 days the animals are sacrificed, the prostate is removed, and the wet prostate weight is determined. Mean weight is determined and statistical significance ($p<0.05$) is determined compared to the vehicle-treated group using the Student's t-test.

Active compounds significantly ($P<0.05$) decrease prostate weight compared to controls. Testosterone is expected to have no effect while estrogen at 30 $\mu$g/kg is expected to significantly reduce prostate weight.

Assay 3: In Vitro Estrogen Receptor Binding

An in vitro estrogen receptor binding assay that measures the ability of the compounds of the present invention to displace [$^3$H]-estradiol from human estrogen receptor obtained by recombinant methods in yeast, bacteria, or mammalian cells is used to determine the estrogen receptor binding affinity of the compounds of this invention. The materials used in this assay are: (1) TD-0.3 assay buffer (containing 10 mM Tris, pH 7.6, 0.3 M potassium chloride, and 5 mM DTT); (2) the radioligand used is [$^3$H]-estradiol obtained from New England Nuclear (Boston, Mass.); (3) the cold ligand used is estradiol obtained from Sigma (St. Louis, Mo.); and (4) recombinant human estrogen receptor, hER.

A solution of the compound being tested is prepared in TD-0.3 with 4% DMSO and 16% ethanol. The tritiated estradiol is dissolved in TD-0.3 such that the final concentration in the assay is 5 nM. The hER is also diluted with TD-0.3 such that 0.2 nM hER is in each assay well. Using microtiter plates, each incubate receives 50 $\mu$l of cold estradiol (nonspecific binding) or the test compound solution, 20 $\mu$l of the tritiated estradiol, and 30 $\mu$l of hER solutions. Each plate contains varying concentrations of the compound and total binding controls in triplicate. The plates are incubated overnight at 4° C. The binding reaction is then terminated by the addition and mixing of 100 ml of 3% hydroxylapatite in 10 mM Tris, pH 7.6, followed by incubation for 15 minutes at 4° C. The mixture is centrifuged and the pellet washed four times with 1% Triton-X100 in 10 mM Tris, pH 7.6. The hydroxylapatite pellets are suspended in Ecolite (+) (ICN Biomedicals, Inc., Aurora, Ohio) and radioactivity is assessed using beta scintigraphy. The mean of all triplicate data points (counts per minute, cpm's) is determined. Specific binding is calculated by subtracting nonspecific cpm's (defined as counts that remain following separation of reaction mixture containing recombinant receptor, radioligand, and excess unlabeled ligand) from total bound cpm's (defined as counts that remain following the separation of reaction mixture containing only recombinant receptor, radioligand). Test compound potency is determined by means of $IC_{50}$ determinations (the concentration of a test compound needed to inhibit 50% of the of the total specific tritiated estradiol bound). Specific binding in the presence of varying concentrations of test compound is determined and calculated as percent specific binding of total specific radioligand bound. Data are plotted as percent inhibition by test compound (linear scale) versus test compound concentration (log scale).

Assay 4: Effect on Total Cholesterol Levels

The effect of the compounds of the present invention on plasma levels of total cholesterol is measured as follows. Blood samples are collected via cardiac puncture from anesthetized female (Sprague-Dawley) rats 4–6 months of age that are bilaterally ovariectomized and treated with the test compound (10–1000 μg/kg/day, for example, sc or orally for 28 days or with control vehicle for the same time), or sham operated. The blood is placed in a tube containing 30 μl of 5% EDTA (10 μl EDTA/1 ml of blood). After centrifugation at 2500 rpm for 10 minutes at 20° C. the plasma is removed and stored at −20° C. The total cholesterol is assayed using a standard enzymatic determination kit from Sigma Diagnostics (Procedure No. 352).

Assay 5: Effect on Obesity

Ten-month-old female Sprague-Dawley rats, weighing approximately 450 grams, are sham-operated or ovariectomized and treated orally with vehicle, 17α-ethynyl-estradiol at 30 mg/kg/day, or a compound according to the present invention at 10–1000 mg/kg/day for 8 weeks. There are 6 to 7 rats in each sub group. On the last day of the study, body composition of all rats is determined via dual energy x-ray absorptiometry using a Hologic QDR-1000/W (Hologic, Bedford, Mass.) equipped with whole body scan software that shows the proportions of fat body mass and lean body mass.

A decrease in fat body mass indicates that the test compound is useful in preventing and treating obesity.

ABBREVIATIONS

Abbreviations used in the following examples and preparations include:

1,2 DCE 1,2-Dichloroethane
d Doublet
dd Double Doublet
DMAP 4-Dimethylamino Pyridine
EDC 1-(3-Dimethylaminopropyl)-3-ethylcarbodiimide Hydrochloride
EtOAc Ethyl Acetate
EtOH Ethyl Alcohol or Ethanol
$Et_2O$ Ethyl Ether
$Et_3N$ Triethylamine
HOBt 1-Hydroxybenzotriazole
HPLC High Pressure Liquid Chromatography
hr Hour(s)
m Multiplet
MeOH Methyl Alcohol or Methanol
min Minute(s)
MS Mass Spectrometry
NMR Nuclear Magnetic Resonance
PPAA 1-Propanephosphonic Acid Cyclic Anhydride
q Quartet
RT (or rt) room temperature (about 20–25° C.)
s Singlet
sat. Saturated
t Triplet
TBAF Tetrabutyl Ammonium Fluoride
TFA Trifluoroacetic Acid
THF Tetrahydrofuran

EXAMPLES AND PREPARATIONS

The following examples will serve to illustrate, but do not limit, the invention that is defined by the claims.

Preparation 1
4-Benzyloxy-N-[2-(3-methoxyphenyl)ethyl]benzamide

A mixture of 3-methoxyphenethylamine (16.557 g, 109.5 mmol), 4-benzyloxybenzoic acid (25.000 g, 109.5 mmol), 1-hydroxybenzotriazole hydrate (22.202 g, 164.3 mmol) and 1-(3-dimethylaminopropyl)-3-ethylcarbodiimide hydrochloride (22.047 g, 115.0 mmol) in anhydrous $CH_2Cl_2$ (300 ml) was stirred at 0° C. under $N_2$ for 1 hr, then warmed to rt and stirred at rt for 19 hr. The reaction mixture was washed sequentially with 1M NaOH (150 ml), 1M HCl (150 ml), and $H_2O$ (150 ml), then dried over $MgSO_4$ and concentrated in vacuo to give 39.00 g (99% yield) of yellow solid.

$^1H$ NMR (400 MHz, $CDCl_3$) δ7.63 (d, J=8.7 Hz, 2H), 7.43–7.30 (m, 5H), 7.21 (d, J=7.7 Hz, 1H), 6.95 (d, J=8.7 Hz, 2H), 6.82–6.78 (m, 2H), 6.76 (s, 1H), 6.02 (m, 1H), 5.08 (s, 2H), 3.77 (s, 3H), 3.68 (dd, J=13.07 Hz, J =6.64 Hz, 2H), 2.90–2.86 (m, 2H); MS m/e 362 ($M^+$+1).

Preparation 2
1-(4-Benzyloxyphenyl)-6-methoxy-3,4-dihydroisoquinoline hydrochloride Phosphorus pentachloride (58.557 g, 281.2 mmol) was added in portions to a solution of 4-benzyloxy-N-[2-(3-methoxyphenyl)ethyl]benzamide (59.775 g, 165.4 mmol) in 1,2-dichloroethane (500 ml) at 0° C. under $N_2$. The resulting reaction was stirred at 0° C. for 30 min, then refluxed for 18 hr. After cooling to rt, hexane (1200 ml) was added and the resulting suspension was cooled to 0° C. The solvent was decanted off from the oil that separated and the remaining oil was dried in vacuo to give 54.56 g (87% yield) of orange residue.

MS m/e 344 ($M^+$+1-HCl).

Preparation 3
1-(4-Benzyloxyphenyl)-6-methoxy-1,2,3,4-tetrahydroisoquinoline

Sodium borohydride (10.874 g, 287.3 mmol) was added in small portions to a solution of 1-(4-benzyloxyphenyl)-6-methoxy-3,4-dihydroisoquinoline (54.56 g, 143.6 mmol) in MeOH (600 ml) at 0° C. The reaction mixture was stirred at 0° C. for 1 hr, then quenched by the dropwise addition of $H_2O$ (20 ml). The resulting mixture was concentrated in vacuo to a volume of about 100 ml. The solid that separated was collected to give 35.926 g (72% yield) of white solid.

$^1$H NMR (400 MHz, CDCl$_3$) δ7.42–7.28 (m, 5H), 7.16 (d, J=8.72 Hz, 2H), 6.91 (d, J=8.72 Hz, 2H), 6.67–6.58 (m, 2H), 6.64 (s, 1H), 5.03 (s, 2H), 4.98 (s, 1H), 3.76 (s, 3H), 3.26–3.21 (m, 1H), 3.08–2.95 (m, 2H), 2.79–2.74 (m, 1H); MS m/e 346 (M$^+$+1).

The remaining filtrate was evaporated in vacuo to give an additional 23.85 g of crude material.

Preparation 4
1-[1-(4-Benzyloxyphenyl)-6-methoxy-3,4-dihydro-1H-isoquinolin-2-yl]-2,2,2-trifluoroethanone Trifluoroacetic anhydride (22.620 g, 107.7 mmol) was added to a solution of 1-(4-benzyloxyphenyl)-6-methoxy-1,2,3,4-tetrahydroisoquinoline (28.530 g, 82.6 mmol) and Et$_3$N (15.0 ml, 107.7 mmol) in anhydrous CH$_2$Cl$_2$ (500 ml) at 0° C. under N$_2$. The resulting yellow solution was stirred at 0° C. for 3 hr, diluted with CH$_2$Cl$_2$ (150 ml), and washed first with 1M HCl (2×100 ml) then 1M NaOH (100 ml), dried over MgSO$_4$, and concentrated in vacuo to give 32.09 g of yellow oil. Purification by flash chromatography, eluting with hexane:EtOAc (9:1) gave 26.97 g (74% yield) of yellow oil.

$^1$H NMR (400 MHz, CDCl$_3$) δ7.40–7.29 (m, 5H), 7.11 (d, J=8.72 Hz, 2H), 6.94 (d, J =8.51 Hz, 1H), 6.87 (d, J=8.72 Hz, 2H), 6.77–6.69 (m, 3H), 5.01 (s, 2H), 3.91–3.80 (m, 1H), 3.79 (s, 3H), 3.48–3.41 (m, 1H), 3.10–3.02 (m, 1H), 2.85–2.80 (m, 1H); MS m/e 442 (M$^+$+1).

Preparation 5
1-{6-Benzyloxy-1-[4-(2-pyrrolidin-1-yl-ethoxy)phenyl]-3,4-dihydro-1H-isoquinolin-2-yl}-2,2,2-trifluoroethanone A solution of 2,2,2-trifluoro-1-{6-hydroxy-1-[4-(2-pyrrolidin-1-yl-ethoxy)phenyl]-3,4-dihydro-1H-isoquinolin-2-yl}ethanone (1.886 g, 4.3 mmol) in anhydrous DMF (50 ml) was added to a suspension of NaH (0.104 g, 4.3 mmol) in anhydrous DMF (100 ml) at rt under N$_2$. After stirring at rt for 1 hr, a solution of benzyl bromide (0.782 g, 4.6 mmol) in anhydrous DMF (10 ml) was added and the reaction mixture was heated to 100° C. for 4 hr. The reaction mixture was cooled to rt, diluted with H$_2$O (250 ml), and extracted with EtOAc (4×100 ml). The combined extracts were washed with H$_2$O (2×100 ml), dried over MgSO$_4$, and concentrated in vacuo to give 2.71 g of orange oil. Purification by flash chromatography, eluting with EtOAc:MeOH (7:3) gave 0.745 g (33% yield) of yellow oil.

$^1$H NMR (400 MHz, CDCl$_3$) δ7.42–7.39 (m, 4H), 7.38–7.33 (m, 1H), 7.20–7.10 (m, 2h), 6.95–6.92 (m, 1H), 6.85–6.79 (m, 4H), 6.72 (br s, 1H), 5.05 (s, 2H), 4.30–4.18 (m, 2H), 3.92–3.88 (m, 1H), 3.47–3.40 (m, 1H), 3.30–2.70 (m, 8H), 1.94 (br s, 4H); MS m/e 525 (M$^+$+1).

Preparation 6
6-Benzyloxy-1-[4-(2-pyrrolidin-1-yl-ethoxy)phenyl]-1,2,3,4-tetrahydroisoquinoline A mixture of 1-{6-benzyloxy-1-[4-(2-pyrrolidin-1-yl-ethoxy)phenyl]-3,4-dihydro-1H-isoquinolin-2yl}-2,2,2-trifluoroethanone (1.088 g, 2.1 mmol) and anhydrous K$_2$CO$_3$ (2.861 g, 20.7 mmol) in MeOH (150 ml) was refluxed under N$_2$ for 18 hr, then evaporated in vacuo to give yellow residue. This was dissolved in H$_2$O (25 ml) and extracted with EtOAc (3×50 ml). The combined extracts were dried over MgSO$_4$, and concentrated in vacuo to give 0.881 g of crude yellow product. Purification by flash chromatography, eluting first with EtOAc:MeOH (8:2), then with EtOAc:MeOH (1:1) gave 0.842 g (95% yield) of yellow oil.

$^1$H NMR (400 MHz, CDCl$_3$) δ7.41–7.29 (m, 5H), 7.17–7.12 (m, 2H), 6.86–6.52 (m, 5H), 5.07–5.05 (m, 1H), 5.02–4.98 (m, 2H), 4.12–4.10 (m, 2H), 3.24–3.21 (m, 1H), 3.06–2.95 (m, 1H), 2.91–2.90 (m, 3H), 2.78–2.75 (m, 1H), 2.65 (br s, 4H), 1.81–1.80 (m, 4H); MS m/e 429 (M$^+$+1).

Preparation 7
{6-Benzyloxy-1-[4-(2-pyrrolidin-1-yl-ethoxy)-phenyl]-3,4-dihydro-1H-isoquinolin-2-yl}phenylmethanone Benzoyl chloride (0.013 g, 0.09 mmol) was added to a solution of 6-benzyloxy-1-[4-(2-pyrrolidin-1-yl-ethoxy)phenyl]-1,2,3,4-tetrahydroisoquinoline (0.040 g, 0.09 mmol) and Et$_3$N (0.026 ml, 0.19 mmol) in anhydrous THF (10 ml) at rt under N$_2$. The resulting suspension was stirred at rt for 20 hr, then evaporated in vacuo to give 0.091 g of white solid. Purification by flash chromatography, eluting with EtOAc: MeOH (6:4) gave 0.049 g (98% yield) of white solid.

$^1$H NMR (400 MHz, CDCl$_3$) δ7.44–7.32 (m, 10H), 7.00–6.96 (m, 2H), 6.82–6.79 (m, 6H), 5.05 (m, 2H), 4.22–4.20 (m, 2H), 3.62–3.58 (m, 1H), 3.32–3.26 (m, 2H), 3.11–3.09 (m, 2H), 2.96–2.92 (m, 4H), 2.69–2.65 (m, 1H), 1.92 (br s, 4H); MS m/e 533 (M$^+$+1).

Preparation 8
1-{6-Benzyloxy-1-[4-(2-pyrrolidin-1-yl-ethoxy)phenyl]-3,4-dihydro-1H-isoquinolin-2-yl}-2,2-dimethylpropan-1-one A solution of 6-benzyloxy-1-[4-(2-pyrrolidin-1-yl-ethoxy)phenyl]-1,2,3,4-tetrahydroisoquinoline (0.015 g, 0.04 mmol) and Et$_3$N (0.01 ml, 0.07 mmol) in anhydrous THF (0.35 ml) was added to a solution of trimethylacetyl chloride (0.04 mmol) in anhydrous THF (0.4 ml) at rt in a sealed reaction vessel. The resulting suspension was stirred at rt for 20 hr, then evaporated to dryness. The product was suspended in a mixture of H$_2$O (0.4 ml) and saturated NaHCO$_3$ solution (0.4 ml), then extracted with CH$_2$Cl$_2$ (3×0.75 ml). The combined extracts were evaporated to dryness to give the crude product. Purification by reverse-phase HPLC, eluting first with gradient. Purification by reverse-phase HPLC on a Primesphere (Phenomenex 2320 West 205$^{th}$ St. Torrance, Calif. 90501) C-18HC (50.0 mm×10.0 mm column with 5 m particle size) column, eluting with a linear gradient starting at time 0 min. of H$_2$O:CH$_3$CN:1% TFA/H$_2$O (85:10:5), increasing to H$_2$O:CH$_3$CN:1% TFA/H$_2$O (5:90:5) at 8 min., detected on a Micromass Platform 2 mass spectrometer (DAD 190–600 nM) gave material which, after evaporation to dryness, was purified by reverse-phase HPLC on a Primesphere C-18HC (3.0 mm×2.0 mm column with 5 m particle size) column, eluting with a linear gradient starting at time 0 min. of H$_2$O:CH$_3$CN:TFA (99.9:0:0.1), increasing to H$_2$O:CH$_3$CN:TFA(0:99.9:0.1) at 4 min., detected with a UV detector (300 nM +/−90 nM and 254 nM +/−25 nM), gave an eluent that was evaporated to dryness to give 0.012 g (56% yield) of the pure product. MS 513 m/e (M$^+$+1).

Preparation 9
4-Benzyloxy-N-phenethylbenzamide

A mixture of phenethylamine (5.000 g, 41.3 mmol), 4-benzyloxybenzoic acid (9.427 g, 41.3 mmol), 1-hydroxybenzotriazole hydrate (8.378 g, 62.0 mmol) and 1-(3-dimethylaminopropyl)-3-ethylcarbodiimide hydrochloride (8.320 g, 43.4 mmol) in anhydrous CH$_2$Cl$_2$ (100 ml) was stirred at 0° C. under N$_2$ for 1 hr, then warmed to rt and stirred at rt for 22 hr. The reaction mixture was washed sequentially with 1M NaOH (50 ml), 1M HCl (50 ml), and H$_2$O (50 ml), then dried over MgSO$_4$ and concentrated in vacuo to give 13.61 g of tan solid. Purification by flash chromatography, eluting first with hexane:EtOAc (1:1) and then with EtOAc gave 12.20 g (89% yield) of white solid.

$^1$H NMR (400 MHz, CDCl$_3$) δ7.63 (d, J=8.92 Hz, 2H), 7.42–7.36 (m, 4H), 7.35–7.29 (m, 3H), 7.24–7.21 (m, 3H), 6.95 (d, J=8.92 Hz, 2H), 6.00 (br s, 1H), 5.08 (s, 2H), 3.71–3.66 (m, 2H), 2.92–2.89 (m, 2H); MS m/e 332 (M$^+$+1).

Preparation 10

1-(4-Benzyloxyphenyl)-3,4-dihydroisoquinoline

A solution of 4-benzyloxy-N-phenethylbenzamide (1.000 g, 3.0 mmol) in POCl$_3$ (10 ml, 107.3 mmol) was refluxed under N$_2$ for 18 hr, then the cooled reaction mixture was slowly added to ice-water (50 ml) with stirring. The resulting mixture was extracted with EtOAc (4×20 ml), then the remaining aqueous layer was basified to pH 10 with concentrated ammonia (80 ml). This was extracted with EtOAc (3×50 ml), then the combined extracts were dried over MgSO$_4$ and concentrated in vacuo to give 0.270 g of yellow solid. Purification by flash chromatography, eluting with hexane:EtOAc (6:4) gave 0.151 g (16% yield) of yellow solid.

$^1$H NMR (400 MHz, CDCl$_3$) δ7.55 (d, J=8.92 Hz, 2H), 7.45–7.43 (d, J=7.06 Hz 2H), 7.40–7.29 (m, 6H), 7.26–7.24 (m, 1H), 7.00 (d, J=8.92 Hz, 2H), 5.11 (s, 2H), 3.81–3.78 (m, 2H), 2.79–2.75 (m, 2H); MS m/e 314 (M$^+$+1).

Preparation 11

1-(4-Benzyloxyphenyl)-1,2,3,4-tetrahydroisoquinoline

Sodium borohydride (0.34 g, 0.89 mmol) was added in small portions to a solution of 1-(4-benzyloxyphenyl)-3,4-dihydroisoquinoline (0.139 g, 0.44 mmol) in MeOH (10 ml) at 0° C. The reaction mixture was stirred at 0° C. for 30 min, stirred at rt for 1 hr, then quenched by the dropwise addition of H$_2$O (1.0 ml). The resulting mixture was concentrated in vacuo to remove the methanol, and the remaining aqueous layer was extracted with CHCl$_3$ (4×10 ml). The combined extracts were dried over MgSO$_4$ and concentrated in vacuo to give 0.138 g (99% yield) of colorless oil.

$^1$H NMR (400 MHz, CDCl$_3$) δ7.43–7.29 (m, 5H), 7.18–7.16 (m, 2H), 7.13–7.12 (m, 2H), 7.10–7.00 (m, 1H), 6.92 (d, J=8.72 Hz, 2H), 6.75 (d, J=7.68 Hz, 1H), 5.05 (s, 1H), 5.04 (s, 2H), 3.28–3.23 (m, 1H), 3.11–2.98 (m, 2H), 2.82–2.77 (m, 1H); MS m/e 316 (M$^+$+1).

Preparation 12

1-[1-(4-Benzyloxyphenyl)-3,4-dihydro-1H-isoquinolin-2-yl]-2,2,2-trifluoroethanone Trifluoroacetic anhydride (0.088 g, 0.42 mmol) was added to a solution of 1-(4-benzyloxyphenyl)-1,2,3,4-tetrahydroisoquinoline (0.132 g, 0.42 mmol) and Et$_3$N (0.117 ml, 0.84 mmol) in anhydrous CH$_2$Cl$_2$ (5 ml) at 0° C. under N$_2$. The resulting yellow solution was stirred at rt for 5 hr, washed first with 1M HCl (5 ml) then 1M NaOH (5 ml), dried over MgSO$_4$, and concentrated in vacuo to give 0.186 g of yellow oil. Purification by flash chromatography, eluting with hexane:EtOAc (9:1) gave 0.147 g (85% yield) of yellow oil.

$^1$H NMR (400 MHz, CDCl$_3$) δ7.41–7.26 (m, 6H), 7.23–7.17 (m, 2H), 7.12 (d, J=8.72 Hz, 2H), 7.03 (d, J=7.26 Hz, 1H), 6.88 (d, J=8.72 Hz, 1H), 6.78 (s, 1H), 5.02 (s, 2H), 3.95–3.91 (m, 1H), 3.52–3.44 (m, 1H), 3.14–3.05 (m, 1H), 2.90–2.86 (m, 1H); MS m/e 410 (M$^+$−1).

Preparation 13

Toluene-4-sulfonic acid 4-(6-methoxy-2-trifluoroacetyl-1,2,3,4-tetrahydroisoquinolin-1-yl)phenyl ester A solution of 2,2,2-trifluoro-1-[1-(4-hydroxyphenyl)-6-methoxy-3,4-dihydro-1H-isoquinolin-2-yl]ethanone (3.387 g, 9.64 mmol), p-toluenesulfonyl chloride (2.206 g, 11.6 mmol) and Et$_3$N (1.6 ml, 11.6 mmol) in acetone (50 ml) was refluxed under N$_2$ for 5 hr, then concentrated in vacuo. The remaining residue was suspended in H$_2$O (100 ml) and extracted with CHCl$_3$ (4×75 ml). The combined extracts were dried over MgSO$_4$ and concentrated in vacuo to give 5.622 g of orange oil. Purification by flash chromatography, eluting with hexane:EtOAc (8:2) gave 4.383 g (90% yield) of white solid.

$^1$H NMR (400 MHz, CDCl$_3$) δ7.71–7.66 (m, 2H), 7.31–7.25 (m, 2H), 7.12 (d, J=8.72 Hz, 1H), 7.12–7.03 (m, 1H), 6.98–6.88 (m, 3H), 6.78–6.68 (m, 2H), 6.70 (s, 1H), 3.91–3.87 (m, 1H), 3.80 (s, 3H), 3.49–3.43 (m, 1H), 2.95–2.91 (m, 1H), 2.84–2.80 (m, 1H), 2.43 (d, J=9.13 Hz, 3H); MS m/e 506 (M$^+$+1).

Preparation 14

Toluene-4-sulfonic acid 4-(6-hydroxy-2-trifluoroacetyl-1,2,3,4-tetrahydroisoquinolin-1-yl)phenyl ester A 1M solution of BBr$_3$ in CH$_2$Cl$_2$ (16.2 ml, 16.2 mmol) was added slowly to a solution of toluene-4-sulfonic acid 4-(6-methoxy-2-trifluoroacetyl-1,2,3,4-tetrahydroisoquinolin-1-yl)phenyl ester (7.459 g, 14.8 mmol) in anhydrous CH$_2$Cl$_2$ (500 ml) at 0° C. under N$_2$. After stirring at 0° C. for 1 hr, the reaction mixture was warmed to rt and stirred at rt for 18 hr. MeOH (250 ml) was slowly added with stirring and the resulting solution was concentrated in vacuo to give 9.793 g of brown residue. Purification by flash chromatography, eluting with hexane:EtOAc (7:3) gave 2.764 g (38% yield) of white solid.

$^1$H NMR (400 MHz, CDCl$_3$) δ7.72–7.69 (m, 2H), 7.30 (d, J=8.51 Hz, 2H), 7.12 (d, J=8.92 Hz, 2H), 6.95–6.85 (m, 3H), 6.72–6.67 (m, 3H), 3.93–3.89 (m, 1H), 3.40–3.32 (m, 1H), 3.07–2.94 (m, 1H), 2.81–2.77 (m, 1H), 2.44 (s, 3H); MS m/e 492 (M$^+$+1).

Preparation 15

Toluene-4-sulfonic acid 4-[6-(2-pyrrolidin-1-yl-ethoxy)-2-trifluoroacetyl-1,2,3,4-tetrahydroisoquinolin-1-yl]phenyl ester A solution of toluene-4-sulfonic acid 4-(6-hydroxy-2-trifluoroacetyl-1,2,3,4-tetrahydroisoquinolin-1-yl)phenyl ester (1.790 g, 3.64 mmol) in anhydrous DMF (30 ml) was added to a suspension of NaH (0.175 g, 7.28 mmol) in anhydrous DMF (30 ml) at rt under N$_2$. After stirring at rt for 1 hr, a solution of 1-(2-chloroethyl)pyrrolidine hydrochloride (0.619 g, 3.64 mmol) in anhydrous DMF (20 ml) was added and the reaction mixture was heated to 100° C. for 5 hr. The reaction mixture was cooled to rt, diluted with H$_2$O (200 ml), and extracted with EtOAc (5×50 ml). The combined extracts were washed with H$_2$O (2×50 ml), dried over MgSO$_4$, and concentrated in vacuo to give 2.193 g of brown oil. Purification by flash chromatography, eluting first with EtOAc:MeOH (9:1), and then with EtOAc:MeOH (7:3), gave 0.482 g (22% yield) of yellow oil.

$^1$H NMR (400 MHz, CDCl$_3$) δ7.70 (d, J=8.30 Hz, 2H), 7.31 (d, J=8.09 Hz, 2H), 7.11 (d, J=8.51 Hz, 2H), 6.92–6.89 (m, 3H), 6.76–6.71 (m, 3H), 4.56–4.51 (m, 2H), 3.93–3.89 (m, 3H), 3.47 (br s, 2H), 3.39–3.33 (m, 1H), 3.08–2.97 (m, 3H), 2.84–2.80 (m, 1H), 2.44 (s, 3H) 2.24–2.21 (m, 2H), 2.16–2.10 (m, 2H); MS m/e 589 (M$^+$+1).

Preparation 16

4-Iodo-N-[2-(3-methoxyphenyl)-ethyl]benzamide

A mixture of 3-methoxyphenethylamine (11.7 g, 77.4 mmol), 4-iodobenzoyl chloride (20.6 g, 77.4 mmol), and Et$_3$N (8.2 g, 81.2 mmol) in anhydrous CH$_2$Cl$_2$ (250 ml) was stirred at 0° C. under N$_2$ for 1 hr, then warmed to rt and stirred at rt for 19 hr. The reaction mixture was washed sequentially with 1M HCl (2×150 ml), 1M NaOH (2×150 ml), and saturated NaCl solution (150 ml), then dried over $Na_2SO_4$ and concentrated in vacuo to give 21 g (72% yield) of white solid.

$^1$H NMR (400 MHz, $CDCl_3$) δ7.74 (d, J=8.52 Hz, 2H), 7.39 (d, J=8.52 Hz, 2H), 7.25–7.21 (m, 1H), 6.81–6.75 (m, 3H), 6.06 (br s, 1H), 3.78 (s, 3H), 3.71–3.67 (m, 2H), 2.91–2.87 (m, 2H); MS m/e 382 ($M^+$+1).

Preparation 17

1-(4-Iodophenyl)-6-methoxy-3,4-dihydroisoquinoline hydrochloride

Phosphorus pentachloride (11 g, 52.8 mmol) was added in portions to a solution of 4-iodo-N-[2-(3-methoxyphenyl)-ethyl]benzamide (10.1 g, 26 mmol) in $CHCl_3$ (60 ml) at 0° C. under $N_2$. The resulting reaction was stirred at 0° C. for 10 min, then warmed to rt and stirred at rt for 18 hr. After cooling to 0° C., hexane (500 ml) was added and the resulting suspension was allowed to settle. The solvent was decanted off from the oil that separated and the remaining oil was triturated with EtOH (20 ml) to give a white solid. $Et_2O$ (200 ml) was added, the resulting suspension was stirred for 1 hr, the solid was collected and dried in vacuo to give 7.5 g (72% yield) of white solid.

Preparation 18

1-(4-Iodophenyl)-6-methoxy-1,2,3,4-tetrahydroisoquinoline

Sodium borohydride (2 g, 52.9 mmol) was added in small portions to a solution of 1-(4-iodophenyl)-6-methoxy-3,4-dihydroisoquinoline hydrochloride (7.5 g, 18.7 mmol) in MeOH (100 ml) at 0° C. The reaction mixture was stirred at 0° C. for 1 hr, then quenched by the dropwise addition of $H_2O$ (20 ml). The resulting mixture was concentrated in vacuo to remove most of the MeOH, then EtOAc was added. The resulting mixture was extracted with 1M NaOH (2×25 ml), then saturated NaCl solution (25 ml), dried over $MgSO_4$, and evaporated in vacuo to give 6.2 g (65% yield) of white solid.

$^1$H NMR (400 MHz, $CDCl_3$) δ7.63 (d, J=8.52 Hz, 1H), 7.01 (d, J=8.31 Hz, 2H), 6.66 (d, 1H), 6.61 (d, J=1.45 Hz, 2H), 5.03 (s, 2H), 4.98 (s, 1H), 3.77 (s, 3H), 3.24–3.20 (m, 1H), 3.08–2.96 (m, 2H), 2.80–2.75 (m, 1H); MS m/e 366 ($M^+$+1).

Preparation 19

Cyclohexanecarboxylic acid [2-(3-methoxyphenyl)ethyl] amide

A mixture of 3-methoxyphenethylamine (1.000 g, 6.61 mmol), cyclohexanecarboxylic acid (0.847 g, 6.61 mmol), 1-hydroxybenzotriazole hydrate (1.340 g, 9.92 mmol), and 1-(3-dimethylaminopropyl)-3-ethylcarbodiimide hydrochloride (1.330 g, 6.94 mmol) in anhydrous $CH_2Cl_2$ (20 ml) was stirred at 0° C. under $N_2$ for 1 hr, then warmed to rt and stirred at rt for 18 hr. The reaction mixture was washed sequentially with 1M NaOH (10 ml), 1M HCl (10 ml), and $H_2O$ (10 ml), then dried over $MgSO_4$ and concentrated in vacuo to give 1.301 g of off-white solid. Purification by flash chromatography, eluting with hexane:EtOAc (6:4) gave 1.107 g (64% yield) of white solid.

$^1$H NMR (400 MHz, $CDCl_3$) δ7.23–7.19 (m, 1H), 6.78–6.71 (m, 3H), 5.44 (br s, 3.78 (s, 3H), 3.52–3.47 (m, 2H), 2.79–2.75 (m, 2H), 1.81–1.73 (m, 4H), 1.64 (br s, 1H), 1.41–1.33 (m, 2H), 1.26–1.18 (m, 4H); MS m/e 262 ($M^+$+1).

Preparation 20

1-Cyclohexyl-6-methoxy-3,4-dihydroisoquinoline

A solution of cyclohexanecarboxylic acid [2-(3-methoxyphenyl)ethyl]amide (1.000 g, 3.8 mmol) in $POCl_3$ (7.0 ml, 75.1 mmol) was refluxed under $N_2$ for 24 hr, then the cooled reaction mixture was slowly added to ice-water (30 ml) with stirring. The resulting mixture was extracted with EtOAc (3×20 ml), then the remaining aqueous layer was basified to pH 10 with concentrated ammonia (40 ml). This was extracted with $CHCl_3$ (4×20 ml), then the combined extracts were dried over $MgSO_4$ and concentrated in vacuo to give 0.270 g (93% yield) of yellow oil.

$^1$H NMR (400 MHz, $CDCl_3$) δ7.47 (d, J=8.72 Hz, 1H), 6.79 (dd, J=8.51 Hz, J=2.49 Hz, 1H), 6.70 (d, J=2.28 Hz, 1H), 3.83 (s, 3H), 3.66–3.62 (m, 2H), 2.88–2.82 (m, 1H), 2.65–2.62 (m 2H), 1.87–1.81 (m, 4H), 1.46–1.23 (m, 6H); MS m/e 244 ($M^+$+1).

Preparation 21

1-Cyclohexyl-6-methoxy-1,2,3,4-tetrahydroisoquinoline

Sodium borohydride (0.512 g, 13.5 mmol) was added in small portions to a solution of 1-cyclohexyl-6-methoxy-3,4-dihydroisoquinoline (0.822 g, 3.38 mmol) in MeOH (40 ml) at 0° C. The reaction mixture was stirred at 0° C. for 30 min, warmed to rt and stirred at rt for 15 hr, then quenched by the dropwise addition of $H_2O$ (5.0 ml). The resulting mixture was concentrated in vacuo to remove the MeOH and the remaining aqueous solution was extracted with $CHCl_3$ (4×10 ml). The combined extracts were dried over $MgSO_4$ and concentrated in vacuo to give 0.775 g (93% yield) of yellow oil.

$^1$H NMR (400 MHz, $CDCl_3$) δ7.05 (d, J=8.51 Hz, 1H), 6.73–6.70 (dd, J=8.72 Hz, J=2.91 Hz, 1H), 6.59 (d, J=2.70 Hz, 1H), 3.86 (d, J=3.94 Hz, 1H), 3.77 (s, 3H), 3.30–3.25 (m, 1H), 2.95–2.88 (m, 1H), 2.86–2.79 (m, 1H), 2.67–2.61 (m, 1H), 1.89–1.79 (m, 2H), 1.71–1.64 (m, 4H), 1.40–1.23 (m, 4H), 1.17–1.05 (m, 4H); MS m/e 246 ($M^+$+1).

Preparation 22

N-[2-(3-Methoxyphenyl)ethyl]benzamide

Benzoyl chloride (0.922 g, 6.61 mmol) was added to a solution of 3-methoxyphenethylamine (1.000 g, 6.61 mmol) and $Et_3N$ (2.8 ml, 19.8 mmol) in anhydrous THF (30 ml) at rt under $N_2$. The resulting suspension was stirred at rt under $N_2$ for 20 hr. The reaction mixture was filtered and the filtrate was concentrated in vacuo to give 1.811 g of white solid. Purification by flash chromatography, eluting with hexane:EtOAc (7:3) gave 1.689 g (100% yield) of white solid.

$^1$H NMR (400 MHz, $CDCl_3$) δ7.68–7.66 (m, 2H), 7.49–7.40 (m, 1H), 7.39–7.37 (m, 2H), 7.25–7.19 (m, 1H), 6.83–6.79 (m, 2H), 6.77 (s, 1H), 6.11 (br s, 1H), 3.78 (s, 3H), 3.74–3.69 (m, 2H), 2.92–2.89 (m, 2H); MS m/e 256 ($M^+$+1).

Preparation 23

6-Methoxy-1-phenyl-3,4-dihydroisoquinoline

A solution of N-[2-(3-methoxyphenyl)ethyl]benzamide (1.530 g, 5.99 mmol) in phosphorous oxychloride (10 ml, 107.3 mmol) was refluxed under $N_2$ for 24 hours. The cooled reaction mixture was then slowly added to ice-water (50 ml) with stirring, and basified to pH 10 with concentrated ammonia (60 ml). This was extracted with $CHCl_3$ (4×25 ml), and the combined organic extracts were dried over $MgSO_4$ then concentrated in vacuo to give 1.548 g (100% yield) of yellow oil.

$^1$H NMR (400 MHz, $CDCl_3$) δ7.60–7.58 (m, 2H), 7.47–7.39 (m, 3H), 7.22 (d, J=8.51 Hz, 1H), 6.80 (d, J=2.70 Hz, 1H), 6.74 (dd, J=8.51 Hz, J=2.49 Hz, 1H), 3.85 (s, 3H), 3.84–3.80 (m, 2H), 2.82–2.79 (m, 2H); MS m/e 238 ($M^+$+1).

Preparation 24
6-Methoxy-1-phenyl-1,2,3,4-tetrahydroisoquinoline

Sodium borohydride (0.945 g, 24.96 mmol) was added in small portions to a solution of 6-methoxy-1-phenyl-3,4-dihydroisoquinoline (1.480 g, 6.24 mmol) in MeOH (50 ml) at 0° C. The reaction mixture was stirred for 30 min, warmed to rt and stirred at rt for 19 hr, then quenched by the dropwise addition of $H_2O$ (10 ml). Excess MeOH was removed by evaporation and the resulting aqueous solution was extracted with $CHCl_3$ (4×10 ml). The combined organic extracts were dried over $MgSO_4$ and concentrated in vacuo to give 1.308 g (88% yield) of white solid.

$^1H$ NMR (400 MHz, $CDCl_3$) δ7.33–7.26 (m, 5H), 6.66–6.59 (m, 3H), 5.05 (s, 1H), 3.76 (s, 3H), 3.26–3.20 (m, 1H), 3.08–2.99 (m, 2H), 2.84–2.77 (m, 1H); MS m/e 238 ($M^+$+1). 240 ($M^+$+1).

Preparation 25
Thiophene-2-carboxylic acid [2-(3-methoxyphenyl)ethyl] amide

A mixture of 3-methoxyphenethylamine (1.000 g, 6.61 mmol), 2-thiophenecarboxylic acid (0.847 g, 6.61 mmol), 1-hydroxybenzotriazole hydrate (1.340 g, 9.92 mmol), and 1-(3-diethylaminopropyl)-3-ethylcarbodiimide hydrochloride (1.330 g, 6.94 mmol) in anhydrous $CH_2Cl_2$ (20 ml) was stirred at 0° C. under $N_2$ for 1 hr, then warmed to rt and stirred at rt for 18 hr. The reaction mixture was washed with 1M NaOH (10 ml) followed by 1M HCl (10 ml), dried over $MgSO_4$, and concentrated in vacuo to give 1.859 g of yellow oil. Purification by flash chromatography, eluting with hexane:EtOAc (7:3) gave 1.637 g (95% yield) of yellow oil.

$^1H$ NMR (400 MHz, $CDCl_3$) δ7.43 (dd, J=4.98 Hz, J=1.04 Hz, 1H), 7.38 (dd, J=3.74 Hz, J=1.25 Hz, 1H), 7.25–7.21 (m, 1H), 7.03 (dd, J=4.98 Hz, J=3.74 Hz, 1H), 6.82–6.76 (m, 3H), 5.97 (br s, 1H), 3.78 (s, 3H), 3.70–3.65 (m, 2H), 2.90–2.87 (m, 2H); MS m/e 262 ($M^+$+1).

Preparation 26
6-Methoxy-1-thiophen-2-yl-3,4-dihydroisoquinoline

A solution of thiophene-2-carboxylic acid [2-(3-methoxyphenyl)ethyl]amide (1.480 g, 5.66 mmol) in phosphorous oxychloride (10 ml, 107.3 mmol) was refluxed under $N_2$ for 24 hr. The cooled reaction mixture was then slowly added to ice-water (50 ml) with stirring and basified to pH 10 with concentrated ammonia (60 ml). This was extracted with $CHCl_3$ (4×25 ml) and the combined extracts were dried over $MgSO_4$ then concentrated in vacuo to give 1.517 g (96% yield) of yellow oil.

$^1H$ NMR (400 MHz, $CDCl_3$) δ7.66 (d, J=8.51 Hz, 1H), 7.48–7.45 (m, 2H), 7.13–7.11 (m, 1H), 6.88–6.81 (m, 2H), 3.87 (s, 3H), 3.80–3.76 (m, 2H), 2.79–2.75 (m, 2H); MS m/e 244 ($M^+$+1).

Preparation 27
6-Methoxy-1-thiophen-2-yl-1,2,3,4-tetrahydroisoquinoline

Sodium borohydride (0.916 g, 24.2 mmol) was added in small portions to a solution of 6-methoxy-1-thiophen-2-yl-3,4-dihydroisoquinoline (1.470 g, 6.04 mmol) in MeOH (50 ml) at 0° C. The reaction mixture was stirred for 30 min, warmed to rt and stirred at rt for 21 hr, then quenched by the dropwise addition of $H_2O$ (10 ml). Excess MeOH was removed by evaporation and the resulting aqueous solution was extracted with $CHCl_3$ (4×10 ml). The combined extracts were dried over $MgSO_4$ and concentrated in vacuo to give 1.316 g (89% yield) of yellow solid.

$^1H$ NMR (400 MHz, $CDCl_3$) δ7.23 (d, J=2.91 Hz, 1H), 6.94–6.88 (m, 3H), 6.68–6.65 (m, 2H), 5.39 (s, 1H), 3.77 (s, 3H), 3.28–3.22 (m, 1H), 3.11–3.05 (m, 1H), 2.97–2.90 (m, 1H), 2.87–2.82 (m, 1H); MS m/e 246 ($M^+$+1).

Preparation 28
4-Bromo-N-[2-(3-methoxyphenyl)ethyl]benzamide

To a stirred solution of 3-methoxyphenethylamine (25.0 g, 165 mmol) and $Et_3N$ (30.0 ml, 214.50 mmol) in $CH_2Cl_2$ (500 ml) at 0° C. was added 4-bromobenzoyl chloride (25 g, 181 mmol) in portions, and the mixture stirred for 30 min. 2N HCl was added and stirred for 5 min, and the aqueous layer was separated. The organic phase was washed sequentially with 1N HCl (1×200 ml), $H_2O$ (2×100 ml), and saturated $NaHCO_3$ solution (100 ml), dried over $MgSO_4$, and concentrated in vacuo to give 28.42 g (52% yield) of off-white solid.

$^1H$ NMR (400 MHz, $CDCl_3$) δ7.53 (m, 4H), 7.23 (m, 1H), 6.82–6.73 (m, 3H), 3.77 (s, 3H), 3.75–3.69 (m, 2H), 2.89 (t, 2H); MS m/e 334, 336 bromine isotope pattern ($M^+$+1).

Preparation 29
1-(4-Bromophenyl)-6-methoxy-3,4-dihydroisoquinoline hydrochloride To a solution of 4-bromo-N-[2-(3-methoxyphenyl)ethyl] benzamide (5.00 g, 15.0 mmol) in $CHCl_3$ (30 ml) was added phosphorous pentachloride (5.30 g, 25.0 mmol) and the mixture stirred for 18 hr at rt under $N_2$. Hexane was added to the mixture and the liquid was then decanted off. EtOH (15 ml) was added to the residue and the mixture was triturated with diethyl ether to give 3.65 g (69% yield) of off-white solid.

$^1H$ NMR (400 MHz, $CD_3OD$) δ7.86 (d, J=8.51 Hz, 2H), 7.61 (d, J=8.30 Hz, 2H), 7.47 (d, J=8.92 Hz, 1H), 7.04 (d, J=2.49 Hz, 1H), 7.04 (dd, J=8.92 Hz, J=2.70 Hz, 1H), 3.98–3.94 (m, 5H), 3.29–3.23 (m, 2H).

Preparation 30
1-(4-Bromophenyl)-6-methoxy-1,2,3,4-tetrahydroisoquinoline

Sodium borohydride (0.720 g, 19.0 mmol) was added in small portions to a solution of 1-(4-bromophenyl)-6-methoxy-3,4-dihydroisoquinoline, hydrochloride (3.62 g, 10.2 mmol) in MeOH (30 ml) at 0° C. The reaction mixture was stirred for 30 min, warmed to rt, and stirred at rt for 1 hr, then quenched by the dropwise addition of $H_2O$ (10 ml). Acetic acid (10 drops) was added with stirring, and the resulting mixture was basified to pH 10 with 1N NaOH and extracted with EtOAc (3×25 ml). The combined extracts were washed with 1N NaOH followed by saturated NaCl solution, dried over $Na_2SO_4$, and concentrated in vacuo to give 3.24 g (100% yield) of white solid.

$^1H$ NMR (400 MHz, $CDCl_3$) δ7.43 (d, J=8.51 Hz, 1H), 7.15 (d, J=8.51 Hz, 1H), 6.66–6.60 (m, 3H), 5.02 (s, 1H), 3.76 (s, 3H), 3.23–3.17 (m, 1H), 3.07–3.01 (m, 2H), 2.84–2.78 (m, 1H).

Preparation 31
2-Benzenesulfonyl-6-benzyloxy-1-[4-(2-pyrrolidin-1-yl-ethoxy)phenyl]-1,2,3,4-tetrahydroisoquinoline Benzenesulfonyl chloride (0.016 g, 0.09 mmol) was added to a solution of 6-benzyloxy-1-[4-(2-pyrrolidin-1-yl-ethoxy)phenyl]-1,2,3,4-tetrahydroisoquinoline (0.040 g, 0.09 mmol) and $Et_3N$ (0.026 ml, 0.19 mmol) in anhydrous THF (10 ml) at rt under $N_2$. The resulting suspension was stirred at rt for 18 hr, then evaporated in vacuo to give 0.086 g of yellow residue. Purification by flash chromatography, eluting with EtOAc:MeOH (6:4) gave 0.045 g (85% yield) of white solid.

$^1H$ NMR (400 MHz, $CDCl_3$) δ7.65 (d, J=7.26 Hz, 3H), 7.38 (s, 5H), 7.34–7.32 (m, 1H), 7.28 (d, J=7.06 Hz, 3H), 7.07 (d, J=7.47 Hz, 3H), 6.86 (d, J=7.47 Hz, 1H), 6.76 (d, J=6.64 Hz, 4H), 6.54 (s, 1H), 6.14 (s, 1H), 4.98 (s, 2H), 4.28–4.24 (m, 1H), 3.78–3.74 (m, 1H), 3.33–3.24 (m, 4H), 2.55–2.45 (m, 2H), 1.96 (br s, 4H); MS m/e 569 (M$^+$+1).

Preparation 32
6-Benzyloxy-2-(naphthalene-1-sulfonyl)-1-[4-(2-pyrrolidin-1-yl-ethoxy)-phenyl]-1,2,3,4-tetrahydroisoquinoline A solution of 6-benzyloxy-1-[4-(2-pyrrolidin-1-yl-ethoxy)phenyl]-1,2,3,4-tetrahydroisoquinoline (0.015 g, 0.04 mmol) and Et$_3$N (0.01 ml, 0.07 mmol) in anhydrous THF (0.35 ml) was added to a solution of 1-naphthalenesulfonyl chloride (0.04 mmol) in anhydrous THF (0.4 ml) at rt in a sealed reaction vessel. The resulting suspension was stirred at rt for 20 hr, then evaporated to dryness. The product was suspended in a mixture of H$_2$O (0.4 ml) and saturated NaHCO$_3$ solution (0.4 ml), then extracted with CH$_2$Cl$_2$ (3×0.75 ml). The combined extracts were evaporated to dryness to give the crude product. Purification by reverse-phase HPLC on a Primesphere C-18HC (50.0 mm×10.0 mm column with 5 m particle size) column, eluting with a linear gradient starting at time 0 min. of H$_2$O:CH$_3$CN 1% TFA/H$_2$O (85:10:5), increasing to H$_2$O:CH$_3$CN:1% TFA/H$_2$O (5:90:5) at 8 min., detected on a Micromass Platform 2 mass spectrometer (DAD 190–600 nM) gave material which, after evaporation to dryness, was purified by reverse-phase HPLC on a Primesphere C-18HC (3.0 mm×2.0 mm column with 5 m particle size) column, eluting with a linear gradient starting at time 0 min. of H$_2$O:CH$_3$CN:TFA (99.9:0:0.1), increasing to H$_2$O:CH$_3$CN:TFA (0:99.9:0.1) at 4 min., detected with a UV detector (300 nM +/−90 nM and 254 nM +/−25 nM), gave an eluent that was evaporated to dryness to give the named product. MS m/e 583 (M$^+$+1).

Preparation 33
6-Benzyloxy-2-(3,5-dimethylisoxazole-4-sulfonyl)-1-[4-(2-pyrrolidin-1-yl-ethoxy)phenyl]-1,2,3,4-tetrahydroisoquinoline 3,5-Dimethylisoxazole-4-sulfonyl chloride (0.034 g, 0.18 mmol) was added to a solution of 6-benzyloxy-1-[4-(2-pyrrolidin-1-yl-ethoxy)phenyl]-1,2,3,4-tetrahydroisoquinoline (0.075 g, 0.18 mmol) and Et$_3$N (0.037 ml, 0.26 mmol) in anhydrous THF (10 ml) at rt under N$_2$. The resulting suspension was stirred at rt for 21 hr, then evaporated in vacuo to a residue that was suspended in a mixture of saturated NaHCO$_3$ solution (4 ml) and H$_2$O (4 ml). This was extracted with CHCl$_3$ (4×5 ml) and the combined extracts were dried over MgSO$_4$, then concentrated in vacuo to give 0.110 g of yellow oil. Purification by flash chromatography, eluting with EtOAc:MeOH (1:1) gave 0.078 g (76% yield) of white solid.

$^1$H NMR (400 MHz, CDCl$_3$) δ7.42–7.37 (m, 2H), 7.33 (d, J=6.65 Hz, 1H), 7.19–7.10 (m, 1H), 7.02–6.98 (m, 2H), 6.90–6.87 (m, 2H), 6.81–6.79 (m, 3H), 6.69 (s, 1H), 6.05 (s, 1H), 5.01 (s, 2H), 4.08–4.03 (m, 2H), 3.72–3.67 (m, 1H), 3.35–3.30 (m, 1H), 2.87–2.84 (m, 2H), 2.74–2.71 (m, 1H), 2.67–2.66 (m, 1H), 2.59 (s, 4H), 2.55 (s, 1H), 2.52 (s, 2H), 2.19 (s, 2H), 2.17 (s, 1H), 1.78 (br s, 4H); MS m/e 588 (M$^+$+1).

Preparation 34
1-[4-(2-Pyrrolidin-1-yl-ethoxy)phenyl]-1,2,3,4-tetrahydroisoquinolin-6-ol A mixture of 6-benzyloxy-1-[4-(2-pyrrolidin-1-yl-ethoxy)phenyl]-1,2,3,4-tetrahydroisoquinoline (0.300 g, 0.70 mmol), ammonium formate (0.883 g, 14.0 mmol), and 20% Pd(OH)$_2$/C (0.050 g) in MeOH (50 ml) was refluxed under N$_2$ for 1 hr, then filtered through Celite®. The filtrate was evaporated in vacuo to a yellow residue that was suspended in a mixture of H$_2$O (5 ml) and saturated NaHCO$_3$ solution (5 ml), then extracted with CH$_2$Cl$_2$ (4×10 ml). The combined organic extracts were dried over MgSO$_4$ and concentrated in vacuo to give 0.133 g of yellow oil. The aqueous layer was extracted again with CH$_2$Cl$_2$ (4×50 ml) to give an additional 0.083 g of yellow oil, for a total of 0.216 g (91% yield) of product.

$^1$H NMR (400 MHz, CDCl$_3$) δ7.54 (d, J=8.51 Hz, 1H), 7.09 (d, J=8.51 Hz, 1H), 6.83 (d, J=8.72 Hz, 1H), 6.72 (d, J=8.51 Hz, 1H), 6.57–6.47 (m, 3H), 4.97 (s, 1H), 4.09–4.05 (m, 2H), 3.18–3.15 (m, 1H), 3.01–2.88 (m, 4H), 2.80–2.79 (m, 1H), 2.69 (br s, 4H), 2.16–2.15 (m, 1H), 1.83 (brs, 4H); MS m/e 339 (M$^+$+1).

Preparation 35
6-Benzyloxy-1-[4-(2-pyrrolidin-1-yl-ethoxy)phenyl]-3,4-dihydro-1H-isoquinoline-2-carboxylic acid tert-butyl ester A solution of di-tert-butyl dicarbonate (0.035 g, 0.16 mmol), 6-benzyloxy-1-[4-(2-pyrrolidin-1-yl-ethoxy)phenyl]-1,2,3,4-tetrahydroisoquinoline (0.069 g, 0.16 mmol), and Et$_3$N (0.028 ml, 0.20 mmol) in anhydrous THF (10 ml) was stirred at rt under N$_2$ for 20 hr. The reaction mixture was concentrated in vacuo to give 0.081 g of yellow oil. Purification by flash chromatography, eluting with EtOAc:MeOH (6:4), gave 0.041 g (48% yield) of white solid.

$^1$H NMR (400 MHz, CDCl$_3$) δ7.43–7.27 (m, 5H), 7.20–7.14 (m, 1H), 7.10 (d, J=8.72 Hz, 2H), 6.90 (br s, 1H), 6.80–6.77 (m, 4H), 5.03 (s, 2H), 4.18 (br s, 2H), 3.13–2.65 (m, 10H), 1.89 (br s, 4H), 1.47 (s, 9H); MS, m/e 529 (M$^+$+1).

Preparation 36
6-Benzyloxy-1-[4-(2-pyrrolidin-1-yl-ethoxy)phenyl]-3,4-dihydro-1H-isoquinoline-2-carboxylic acid ethyl ester A solution of ethyl chloroformate (0.017 g, 0.16 mmol), 6-benzyloxy-1-[4-(2-pyrrolidin-1-yl-ethoxy)phenyl]-1,2,3,4-tetrahydroisoquinoline (0.069 g, 0.16 mmol), and Et$_3$N (0.028 ml, 0.20 mmol) in anhydrous THF (10 ml) was stirred at rt under N$_2$ for 20 hr. The reaction mixture was concentrated in vacuo to give 0.115 g of tan solid. Purification by flash chromatography, eluting with EtOAc:MeOH (8:2), gave 0.023 g (28% yield) of white solid.

$^1$H NMR (400 MHz, CDCl$_3$) δ7.43–7.29 (m, 6H), 7.12–7.10 (m, 2H), 6.91 (d, J=7.68 Hz, 1H), 6.80–6.77 (m, 4H), 5.04 (s, 2H), 4.29–3.98 (m, 7H), 3.25–2.67 (m, 7H), 1.97 (br s, 4H), 1.30–1.23 (s, 3H); MS, m/e 501 (M$^+$+1).

Preparation 37
2-(3-Methoxy-phenyl)-N-phenyl-acetamide

The title compound was prepared according to the procedure of Nagarajan et al., *Ind. J. Chem.*, 24B:83–97 (1985).

Preparation 38
[2-(3-Methoxy-phenyl)-ethyl]-phenyl-amine

The title compound was prepared according to the procedure of Nagarajan et al., *Ind. J. Chem.*, 24B:83–97 (1985).

Preparation 39
4-Methoxy-N-[2-(3-methoxy-phenyl)-ethyl]-N-phenyl-benzamide

To a stirred solution of 2-(3-methoxy-phenyl)-ethyl]-phenyl-amine (0.800 g, 3.52 mmol, 1.0 eq.) in CH$_2$Cl$_2$ (4 ml) was added Et$_3$N (2.97 ml, 21.1 mmol, 6.0 eq.), PPAA (50% solution in EtOAc, 7.05 mmol, 2.0 eq.), para-methoxy benzoic acid (0.803 g, 5.29 mmol, 1.5 eq.), and a catalytic amount of DMAP. The reaction was stirred at room temperature for 36 hours. The reaction mixture was diluted with CH$_2$Cl$_2$ (30 ml) and washed successively with 1N HCl (1×20 ml) and saturated NaHCO$_3$ (1×20 ml). The organic layer was dried over MgSO$_4$, filtered, and concentrated in vacuo. Flash chromatography (SiO$_2$, hexanes:EtOAc 7:1 to 3:1) of the residue afforded the desired compound as a colorless oil (1.13 g, 3.13 mmol, 89% yield).

$^1$H NMR (400 MHz, CDCl$_3$) $\delta_H$ 2.95 (2H, t, J 8.0 Hz) 3.68 (3H, s), 3.73 (3H,s), 4.08 (2H, t, J 8.0 Hz), 6.60–7.24 (13H, overlapping m).

Preparation 40
Cyclohexanecarboxylic acid [2-(3-methoxy-phenyl)-ethyl]-phenyl-amide The title compound was prepared by analogy to Preparation 39 except that cyclohexane carboxylic acid was used instead of para-methoxy benzoic acid, and hexanes 7:1 EtOAc was used as the eluent for flash chromatography purification.

$^1$H NMR (400 MHz, CDCl$_3$) $\delta_H$ 0.84–0.94 (2H, overlapping m), 1.09–1.23 (2H, overlapping m), 1.44–1.77 (6H, overlapping m), 2.05 (1H, m), 2.81 (2H, m), 3.73 (3H, s), 3.85 (2H, m), 6.68–6.73 (3H, overlapping m), 7.00–7.02 (2H, overlapping m), 7.13 (1H, m) and 7.31–7.38 (3H overlapping m). MS 338 (M+1).

Preparation 41
N-[2-(3-Methoxy-phenyl)-ethyl]-N-phenyl-isobutyramide

The title compound was prepared by analogy to Preparation 39 except that 2-methyl propanoic acid was used instead of para-methoxy benzoic acid, and hexanes 7:1 EtOAc was used as eluent for flash chromatography purification.

$^1$H NMR (400 MHz, CDCl$_3$) $\delta_H$ 1.00 (6H, d, J 6.5 Hz), 2.40 (1H, septet, J 6.5 Hz), 2.85 (2H, t, 7.5 Hz), 3.75 (3H, s), 3.88 (2H, t, 7.5 Hz), 6.72–6.73 (3H, overlapping m) and 7.31–7.41 (9H overlapping m). MS 298 (M+1).

Preparation 42
N-[2-(3-Methoxy-phenyl)-ethyl]-N-phenyl-benzamide

To a stirred solution of 2-(3-methoxy-phenyl)-ethyl]-phenyl-amine (1.38 g, 6.08 mmol, 1.0 eq.) in CH$_2$Cl$_2$ (30 ml) under an atmosphere of N$_2$ was added EDC (1.05 g, 6.69 mmol, 1.1 eq.) and HOBt (1.23 g, 91.2 mmol, 1.5 eq.). Benzoic acid (1.11 g, 9.12 mmol, 1.5 eq.) was added to this mixture, and stirring was continued at room temperature for 24 hours. Additional EDC (1.1 g, 7.01 mmol, 1.15 eq.) and a catalytic amount of DMAP were added, and stirring was continued at room temperature for a further 24 hours. The reaction mixture was diluted with CH$_2$Cl$_2$ (30 ml) and washed sequentially with sat. NaHCO$_3$ (1×30 ml) and 1N HCl (1×30 ml). The basic aqueous layer was back extracted with CH$_2$Cl$_2$ (1×20 ml). The combined organics were dried over MgSO$_4$, filtered, and concentrated in vacuo. The residue was subjected to flash chromatography (SiO$_2$, hexanes:EtOAc 8:1) to give the desired product (1.41 g, 4.24 mmol, 70% yield).

$^1$H NMR (400 MHz, CDCl$_3$) $\delta_H$ 2.96 (2H, t, J 8.0 Hz), 3.74 (3H, s), 4.08 (2H, t, J 8.0 Hz) and 6.73–7.26 (14H, overlapping m). MS 332 (M+1).

Preparation 43
4-(2E-Ethoxycarbonyl-vinyl)-benzoic acid

To a stirred solution of 4-formyl-benzoic acid (10.0 g, 66.7 mmol) in THF (140 ml) was added carboethoxytriphenylphosphorane (25.0 g, 71.8 mmol). To this solution was added NaOH (2.50 g, 66.7 mmol) as a solution in water (20 ml). The reaction was stirred at rt overnight. The reaction mixture was diluted with water (50 ml) and extracted with EtOAc (3×50 ml). The combined extracts were dried over MgSO$_4$, filtered, and concentrated in vacuo. The residue was purified by flash chromatography (SiO$_2$, 5% MeOH/CH$_2$Cl$_2$) to give the desired compound as a white solid (11.68 g, 53.1 mmol, 80% yield).

$^1$H NMR (400 MHz, d$_6$-acetone) $\delta_H$ 1.28 (3H, t, J 7.0 Hz), 4.20 (2H, q, J 7.0 Hz), 6.65 (1H, d, J 16.0 Hz) and 7.67–8.13 (5H, overlapping m).

Preparation 44
3-(4-{[2E-(3-Methoxy-phenyl)-ethyl]-phenyl-carbamoyl}-phenyl)-acrylic acid ethyl ester The title compound was prepared by analogy to Preparation 39 except that 4-(2E-ethoxycarbonyl-vinyl)-benzoic acid was used instead of para-methoxy benzoic acid and the crude material was taken to the next step without any flash chromatography.

MS 430 (M+1).

Preparation 45
N-[2-(3-Methoxy-phenyl)-ethyl]-2,N-diphenyl-acetamide

The title compound was prepared by analogy to Preparation 39 except that phenyl acetic acid was used instead of para-methoxy benzoic acid, and the crude material was taken to the next step without any flash chromatography.

MS 346 (M+1).

Preparation 46
Thiophene-2-carboxylic acid [2-(3-methoxy-phenyl)-ethyl]-phenyl-amide The title compound was prepared by analogy to Preparation 39 except that thiophene-2-carboxylic acid was used instead of para-methoxy benzoic acid, and hexanes 10:1 EtOAc was used as eluent for flash chromatography purification.

$^1$H NMR (400 MHz, CDCl$_3$) $\delta_H$ 2.98 (2H, m), 3.75 (3H, s), 4.05 (2H, m), 6.65–6.80 (5H, overlapping m) and 7.11–7.39 (7H, overlapping m). MS 337 (M).

Preparation 47
Naphthalene-2-carboxylic acid [2-(3-methoxy-phenyl)-ethyl]-phenyl-amide The title compound was prepared by analogy to Preparation 39 except that naphthalene-2-carboxylic acid was used instead of para-methoxy benzoic acid, and the crude material was taken to the next step without any flash chromatography.

MS 382 (M+1).

Preparation 48
3,4,5-Trifluoro-N-[2-(3-methoxy-phenyl)-ethyl]-N-phenyl-benzamide The title compound was prepared by analogy to Preparation 39 except that 3,4,5-trifluorobenzoic acid was used instead of para-methoxy benzoic acid, and the crude material was taken to the next step without any flash chromatography.

MS 386 (M+1).

Preparation 49
4-Chloro-N-[2-(3-methoxy-phenyl)-ethyl]-N-phenyl-benzamide

The title compound was prepared by analogy to Preparation 39 except that 4-chloro-benzoic acid was used instead of para-methoxy benzoic acid, and the crude material was taken to the next step without any flash chromatography.

MS 365 (M+1).

Preparation 50
Thiazole-2-carboxylic acid [2-(3-methoxy-phenyl)-ethyl]-phenyl-amide The title compound was prepared by analogy to Preparation 39 except that thiazole-2-carboxylic acid (see Metzger, *Bull. Soc. Chim. Fr.*, p. 708 (1953)) was used instead of para-methoxy benzoic acid, and the crude material was taken to the next step without any flash chromatography.
MS 338 (M+1).

Preparation 51
Adamantane-1-carboxylic acid [2-(3-methoxy-phenyl)-ethyl]-phenyl-amide The title compound was prepared by analogy to Preparation 39 except that adamantane-1-carboxylic acid was used instead of para-methoxy benzoic acid, and the crude material was taken to the next step without any flash chromatography.
MS 389 (M).

Preparation 52
N-[2-(3-Methoxy-phenyl)-ethyl]-N-phenyl-isonicotinamide

The title compound was prepared by analogy to Preparation 39 except that isonicotinic acid was used instead of para-methoxy benzoic acid, and hexanes:EtOAc 4:1 was used as eluent for flash chromatography purification.
$^1$H NMR (400 MHz, CDCl$_3$) $\delta_H$ 2.95 (2H, m), 3.75(3H, s), 4.10 (2H, m), 6.74–6.85 (3H, overlapping m), 7.08–7.23 (8H, overlapping m) and 8.41 (2H, m). MS 333 (M+1).

Preparation 53
4-Iodo-N-[2-(3-methoxy-phenyl)-ethyl]-N-phenyl-benzamide

To a stirred suspension of 4-iodobenzoic acid (8.5 g, 34.4 mmol, 1.3 eq.) in toluene (21 ml) under an atmosphere of N$_2$ was added thionyl chloride (17 ml). The suspension was heated at reflux for 2 hours forming a turbid solution. The reaction was allowed to cool to RT and the volatiles were removed in vacuo. The residue was taken up in THF (100 ml) under an atmosphere of N$_2$ and cooled to 0° C. To the ice cold solution was added successively Et$_3$N (14.7 ml, 106.0 mmol, 4.0 eq.), a catalytic amount of DMAP, and 2-(3-methoxy-phenyl)-ethyl]-phenyl-amine (6.0 g, 26.4 mmol, 1.0 eq.). After 1 hour at 0° C. the ice bath was removed and stirring was continued at RT overnight. The reaction mixture was diluted with EtOAc (100 ml) and washed successively with 1N HCl (2×100 ml), water (2×100 ml), and 10% K$_2$CO$_3$ (2×100 ml). The organic layer was dried over MgSO$_4$, filtered, and concentrated in vacuo. The residue was subjected to flash chromatography (SiO$_2$, hexanes:EtOAc 8:1 to 4:1 gradient) to give the desired product (11.0 g, 24.1 mmol, 91% yield).
$^1$H NMR (400 MHz, CDCl$_3$) $\delta_H$ 2.96 (2H, t, J 8.0 Hz), 3.77 (3H, s), 4.10 (2H, t, J 8.0 Hz), 6.75–6.87 (5H, overlapping m), 6.99 (2H, d, J 8.5 Hz), 7.15–7.24 (4H, overlapping m) and 7.49 (2H, d, J 8.5 Hz). MS 458 (M+1).

Preparation 54
1-Trifluoroacetyl-piperidine-4-carbonyl chloride

The title compound was prepared according to the procedure of Hibert et al., *J. Med. Chem.*, 33:1594 (1990). [[Was this done exactly as described, or analogously? Done exactly]]

Preparation 55
1-Trifluoroacetyl-piperidine-4-carboxylic acid [2-(3-methoxy-phenyl)-ethyl]-amide To a stirred solution of 3-methoxy phenylethylamine (9.3 g, 61.6 mmol) and triethylamine (8.1 g, 11.2 ml, 80.1 mmol) in CH$_2$Cl$_2$ (50 ml) at 0° C. under an atmosphere of N$_2$ was added 1-trifluoroacetyl-piperidine-4-carbonyl chloride (15.0 g, 61.6 mmol) as a solution in CH$_2$Cl$_2$ (50 ml) in a dropwise manner. The reaction was allowed to warm to RT overnight. The reaction was quenched with water (50 ml), the layers were separated, and the organic layer was washed with water (1×50 ml). The combined aqueous layers were back extracted with CH$_2$Cl$_2$ (1×75 ml). The combined organic layers were washed with brine (1×75 ml). The organic layer was dried over MgSO$_4$, filtered, and concentrated in vacuo. The resulting solid was triturated with Et$_2$O and filtered to give the desired product (18.8 g, 52.3 mmol, 85% yield).
$^1$H NMR (400 MHz, CDCl$_3$) $\delta_H$ 1.58–1.97 (5H, overlapping m), 2.30 (1H, m), 2.79 (2H, t, J 6.5 Hz), 2.91 (1H, m), 3.17 (1H, m), 3.52 (2H, m), 3.79 (3H,s), 3.99 (1H, m), 4.41(1H, m), 5.45 (1H, broad s), 6.71–6.79 (3H, overlapping m) and 7.23 (1H, t, J 8.0 Hz). MS 359 (M+1).

Preparation 56
2,2,2-Trifluoro-1-[4-(6-methoxy-3,4-dihydro-isoquinolin-1-yl)-piperidin-1-yl]-ethanone A stirred solution of 1-trifluoroacetyl-piperidine-4-carboxylic acid [2-(3-methoxy-phenyl)-ethyl]-amide (1.04 g, 2.9 mmol) in POCl$_3$ under an atmosphere of N$_2$ was heated at reflux for 2.5 hours. The reaction was allowed to cool to RT and the POCl$_3$ was removed in vacuo. The residual oil was suspended in toluene (20 ml) and concentrated in vacuo (this process was repeated twice more), leaving the desired product as a tan colored solid (0.872 g, 2.56 mmol, 88% yield). MS 341 (M+1)

Preparation 57
6-Methoxy-1-piperidin-4-yl-3,4-dihydro-isoquinoline

To a stirred solution of 2,2,2-trifluoro-1-[4-(6-methoxy-3,4-dihydro-isoquinolin-1-yl)-piperidin-1-yl]-ethanone (0.160 g, 0.470 mmol) was added a solution of 10% K$_2$CO$_3$ (2 ml). The cloudy mixture was stirred at RT overnight. The reaction mixture was extracted with EtOAc (3×5 ml), the combined organic extracts were washed with brine (1×5 ml), dried over MgSO$_4$, filtered, and concentrated in vacuo to give the desired compound as a yellow oil (0.101 g, 0.413 mmol, 88% yield).
$^1$H NMR (400 MHz, CDCl$_3$) $\delta_H$ 1.67–1.81 (2H, overlapping m), 1.83–2.02 (2H overlapping m), 2.60 (2H, t, J 7.5 Hz), 2.86 (2H, m), 3.08 (1H, m), 3.28 (2H, m), 3.61 (2H, t, J 7.5 Hz), 3.81 (3H, s), 5.24 (1H, broad s), 6.70 (1H, d, J 3.0 Hz), 6.78 (1H, dd, J 8.0 and 3.0 Hz) and 7.38 (1H, d, J 8.0 Hz). MS 245 (M+1).

Preparation 58
6-Methoxy-1-[1-(1-methyl-1H-imidazole-4-sulfonyl)-piperidin-4-yl]-3,4-dihydro-isoquinoline To a stirred solution of 6-methoxy-1-piperidin-4-yl-3,4-dihydro-isoquinoline (0.094 g, 0.385 mmol) and triethylamine (0.078 g, 0.77 mmol) in CH$_2$Cl$_2$ (3 ml) was added 1-methyl-1H-imidazole-4-sulfonyl chloride (0.070 g, 0.385 mmol). The reaction mixture was stirred at RT under an atmosphere of N$_2$ overnight. The reaction mixture was diluted with CH$_2$Cl$_2$ (10 ml) and washed with water (2×5 ml). The organic layer was dried over MgSO$_4$, filtered, and concentrated in vacuo. The residue was purified via radial chromatography (SiO$_2$, 1 mm, CH$_2$Cl$_2$ to 5% MeOH/CH$_2$Cl$_2$) to give the product as an oil (0.084 g, 0.216 mmol, 56% yield).
MS 389 (M+1).

Preparation 59
6-Methoxy-1-[1-(1-methyl-1H-imidazole-4-sulfonyl)-piperidin-4-yl]-1,2,3,4-tetrahydroisoquinoline To a stirred solution of 6-methoxy-1-[1-(1-methyl-1H-imidazole-4-sulfonyl)-piperidin-4-yl]-3,4-dihydroisoquinoline (0.077 g, 0.197 mmol) in MeOH (3 ml) cooled to 0° C. was added NaBH$_4$. The reaction mixture was then stirred at RT for 2 hours and diluted with water (5 ml) and sat. NaHCO$_3$ (5 ml). The mixture was extracted with EtOAc (3×10 ml). The combined organics were washed with brine (1×10 ml), dried over MgSO$_4$, filtered, and concentrated in vacuo. The residue was purified by radial chromatography (SiO$_2$, 1 mm, CH$_2$Cl$_2$ to 5% MeOH/CH$_2$Cl$_2$) to give the product as an oil (0.055 g, 0.141 mmol, 71% yield).

MS 391 (M+1).

Preparation 60
2-Benzylamino-1-(4-methoxy-phenyl)-ethanone

To a solution of Et$_3$N (13.55 g, 133.9 mmol) and benzylamine (11.96 g, 111.6 mmol) in THF (25 ml) was added 2-bromo-1-(4-methoxy-phenyl)-ethanone (25.56 g, 111.6 mmol). The reaction was stirred at RT for 60 minutes, then filtered and the filtrate concentrated in vacuo. The residue was purified via flash chromatography (SiO$_2$, gradient column 35% to 80% EtOAc/hexanes) to give the title product (17.12 g, 67.0 mmol, 60% yield).

$^1$H NMR (400 MHz, CDCl$_3$) $\delta_H$ 3.85 (3H, s), 3.94 (s, 2H), 4.11 (s, 2H), 6.91 (2H, d, J=9.0 Hz), 7.20–7.41 (m, 5H) and 7.87 (2H, d, J 9.0 Hz). MS 256 (M+1).

Preparation 61
2-Benzylamino-1-(4-methoxy-phenyl)-ethanol

To a solution of 2-benzylamino-1-(4-methoxy-phenyl)-ethanone (1.61 g, 6.30 mmol, see Preparation 60) in MeOH (60 ml) was added NaBH$_4$ (0.48 g, 12.6 mmol) in three equal portions. The reaction was stirred at RT overnight, then it was quenched with a 1:1 mixture of water and sat. NaHCO$_3$ (30 ml). The mixture was extracted with CH$_2$Cl$_2$ (3×40 ml), the organics were combined, dried over MgSO$_4$, filtered, and concentrated in vacuo. The residue was purified via Biotage flash chromatography (SiO$_2$, neat EtOAc) to give the title product (1.216 g, 4.72 mmol, 75% yield).

$^1$H NMR (400 MHz, CDCl$_3$) $\delta_H$ 2.68 (2H, broad s), 2.71 (1H, dd, J 12.5 and 9.0 Hz), 2.87 (1H, dd, J 12.5 and 3.5 Hz), 3.77 (3H, s), 3.81 (2H, m), 4.67 (1H, dd J 9.0 Hz and 3.5 Hz), 6.85 (2H, d J 8.5 Hz) and 7.19–7.38 (7H, m). MS 258 (M+1).

Preparation 62
2-[Benzyl-(3-methoxy-benzyl)-amino]-1-(4-methoxy-phenyl)-ethanone To a solution of 2-benzylamino-1-(4-methoxy-phenyl)-ethanone (12.0 g, 47.0 mmol, see Preparation 60) and 3-methoxy benzaldehyde (6.09 g, 44.8 mmol) in 1,2 DCE (250 ml) was added NaB(OAc)$_3$H. The reaction mixture was stirred at RT overnight. The reaction was poured into sat. NaHCO$_3$ (150 ml) and extracted with CH$_2$Cl$_2$ (3×100 ml). The combined organics were dried over MgSO$_4$, filtered, and concentrated in vacuo. Flash chromatography (SiO$_2$, gradient elution 20% to 50% EtOAc/hexanes) gave the title product (13.85 g, 36.9 mmol, 83% yield).

$^1$H NMR (400 MHz, CDCl$_3$) $\delta_H$ 3.76 (2H, s), 3.77 (3H,s), 3.78 (2H, s), 3.83 (2H, s), 3.84 (3H, s), 6.83–6.93 (5H, m), 7.19–7.36 (6H, m) and 7.83 (2H, d, J 7.5 Hz). MS 376 (M+1).

Preparation 63
2-[Benzyl-(3-methoxy-benzyl)-amino]-1-(4-methoxy-phenyl)-ethanol To a solution of 2-[benzyl-(3-methoxy-benzyl)-amino]-1-(4-methoxy-phenyl)-ethanone (13.8 g, 36.75 mmol, see Preparation 62) in MeOH (150 ml) cooled to 0° C. was added NaBH$_4$ in five equal portions over 30 minutes. The reaction was stirred overnight while slowly warming to RT. Water (100 ml) was added to the reaction mixture, the volume was reduced by half in vacuo, and the mixture extracted with CH$_2$Cl$_2$ (3×100 ml). The combined organics were dried over MgSO$_4$, filtered, and concentrated in vacuo. Flash chromatography of the residue (SiO$_2$, gradient elution 20%–50% EtOAc/hexanes) gave the title product (12.87 g, 34.1 mmol, 93% yield).

Alternatively, to a solution of 2-benzylamino-1-(4-methoxy-phenyl)-ethanol (1.20 g, 4.66 mmol, see Preparation 61) and 3-methoxybenzaldehyde (0.700 g, 5.13 mmol) in 1,2 DCE (25 ml) was added NaB(OAc)$_3$H. The mixture was stirred at RT overnight. The reaction mixture was poured into sat. NaHCO$_3$ (30 ml) and extracted with CH$_2$Cl$_2$ (3×50 ml). The combined organics were dried over MgSO$_4$, filtered, and concentrated in vacuo. The residue was purified via flash chromatography (Biotage 15% EtOAc/hexanes) to give the title product (1.72 g, 4.56 mmol, 98% yield).

$^1$H NMR (400 MHz, CDCl$_3$) $\delta_H$ 2.58 (1H, m), 3.44 (1H, m), 3.72 (1H, m), 3.75 (3H, s), 3.78 (3H, s), 3.88 (1H, m), 4.65 (1H, m), 6.79–6.90 (5H, m) and 7.12–7.32 (8H, m).

MS 378 (M+1).

Preparation 64
7-Methoxy-4-(4-methoxy-phenyl)-1,2,3,4-tetrahydroisoquinoline A suspension of 10% Pd/C (3.80 g) and 2-benzyl-7-methoxy-4-(4-methoxy-phenyl)-1,2,3,4-tetrahydroisoquinoline (3.87 g, 10.8 mmol, see Example 80) in EtOH (160 ml) was hydrogenated at 50 p.s.i. for 12 hours. The catalyst was removed via filtration through diatomaceous earth and the filtrate was concentrated in vacuo. Purification via flash chromatography (Biotage , SiO$_2$, 9:1 EtOAc:MeOH then 1:1 EtOAc:MeOH) gave the title product (2.19 g, 8.13 mmol, 76% yield).

$^1$H NMR (400 MHz, CD$_3$OD) $\delta_H$ 2.88 (1H, dd, J 12.5 and 8.5 Hz), 3.21–3.31 (2H, m), 3.71 (3H, s), 3.73 (3H, s), 3.91–4.06 (2H, m), 6.61 (2H, m), 6.68 (1H, m), 6.81(2H, d J 8.5 Hz) and 6.98 (2H, d, J 8.5 Hz). MS 270 (M+1).

Preparation 65
6-Methoxy-1-(4-methoxy-phenyl)-2-phenyl-1,2,3,4-tetrahydroisoquinoline A stirred solution of 4-methoxy-N-[2-(3-methoxy-phenyl)-ethyl]-N-phenyl-benzamide in POCl$_3$ under an atmosphere of N$_2$ was heated at reflux for 14 hours. The solution was allowed to cool to rt and concentrated in vacuo. The residue was taken up in CH$_2$Cl$_2$ (30 ml) and washed with sat. NaHCO$_3$ until CO$_2$ evolution ceased. The organic layer was dried over MgSO$_4$, filtered, and concentrated in vacuo. The residue was dissolved in MeOH (20 ml), cooled to 0° C., and NaBH$_4$ (0.105 g, 2.77 mmol) was added in a portionwise manner. The reaction was stirred for 2 hours at 0° C., then additional NaBH$_4$ (0.105 g, 2.77 mmol) was added. The reaction was stirred at rt overnight, diluted with CH$_2$Cl$_2$ (50 ml), and washed with sat. NaHCO$_3$ solution (1×50 ml). The organic layer was dried over MgSO$_4$, filtered, and concentrated in vacuo. The residue was subjected to flash chromatography (SiO$_2$, hexanes:EtOAc 10:1) to give the desired compound as a colorless oil (0.550 g, 1.59 mmol, 58% yield).

¹H NMR (400 MHz, CDCl₃) δ$_H$ 2.89 (2H, m,) 3.46 (1H, m), 3.63 (1H, m), 3.73 (3H, s), 3.77 (3H, s), 5.73 (1H, s) 6.69–7.22 (12H, overlapping m).

See also Nagarajan et al., *Ind. J. Chem.*, 24B:83–97 (1985).

Preparation 66
6-Methoxy-1,2-diphenyl-1,2,3,4-tetrahydroisoquinoline

The title compound was prepared by analogy to Preparation 65 except that N-[2-(3-methoxy-phenyl)-ethyl]-N-phenyl-benzamide was used instead of 4-methoxy-N-[2-(3-methoxy-phenyl)-ethyl]-N-phenyl-benzamide and the final residue was subjected to flash column chromatography using hexanes:EtOAc 10:1.

¹H NMR (400 MHz, CDCl₃) δ$_H$ 2.88 (2H, m), 3.47 (1H, m), 3.69 (1H, m), 3.77 (3H, s), 5.77 (1H, s), 6.70–7.24 (13H, overlapping m). MS 316 (M+1).

See also Nagarajan et al., *Ind. J. Chem.*, 24B:83–97 (1985).

Preparation 67
1-(4-Chloro-phenyl)-6-methoxy-2-phenyl-1,2,3,4-tetrahydroisoquinoline The title compound was prepared by analogy to Preparation 65 except that 4-chloro-N-[2-(3-methoxy-phenyl)-ethyl]-N-phenyl-benzamide was used instead of 4-methoxy-N-[2-(3-methoxy-phenyl)-ethyl]-N-phenyl-benzamide, and the final residue was not subjected to flash chromatography. MS 349 (M+1).

See also Nagarajan et al., *Ind. J. Chem.*, 24B:83–97 (1985).

EXAMPLE 1

2,2,2-Trifluoro-1-[1-(4-hydroxyphenyl)-6-methoxy-3,4-dihydro-1H-isoquinolin-2-yl]ethanone 1-[1-(4-Benzyloxyphenyl)-6-methoxy-3,4-dihydro-1H-isoquinolin-2-yl]-2,2,2-trifluoroethanone (26.97 g, 61.1 mmol) was hydrogenated using 10% Pd/C (1.000 g) in EtOH (300 ml) at an initial pressure of 44 psi (~300,000 Pa) at rt for 6 hr. The reaction mixture was filtered through a pad of Celite to remove the catalyst and the filtrate was evaporated in vacuo to give 18.98 g (88% yield) of white solid.

¹H NMR (400 MHz, CDCl₃) δ7.08–7.06 (m, 2H), 6.96–6.92 (m, 1H), 6.79–6.69 (m, 5H), 4.81 (br s, 1H), 3.92–3.88 (m, 1H), 3.80 (s, 3H), 3.48–3.40 (m, 1H), 3.10–3.01 (m, 1H), 2.85–2.81 (m, 1H); MS m/e 352 (M⁺+1).

EXAMPLE 2

2,2,2-Trifluoro-1-{6-methoxy-1-[4-(2-pyrrolidin-1-yl-ethoxy)phenyl]-3,4-dihydro-1H-isoquinolin-2-yl}ethanone A solution of 2,2,2-trifluoro-1-[1-(4-hydroxyphenyl)-6-methoxy-3,4-dihydro-1H-isoquinolin-2-yl]ethanone (18.98 g, 54.0 mmol) in anhydrous DMF (200 ml) was added to a suspension of NaH (2.592 g, 108.0 mmol) in anhydrous DMF (400 ml) at rt under N₂. After stirring at rt for 1 hr, a solution of 1-(2-chloroethyl)pyrrolidine hydrochloride (9.184 g, 54.0 mmol) in anhydrous DMF (200 ml) was added and the reaction mixture was heated to 100° C. for 4 hr. The reaction mixture was cooled to rt, diluted with H₂O (2000 ml), and extracted with EtOAc (4×250 ml). The combined extracts were washed with H₂O (3×250 ml), dried over MgSO₄, and concentrated in vacuo to give 21.15 g of yellow oil. Purification by flash chromatography, eluting with EtOAc:MeOH (8:2) gave 10.503 g (43% yield) of yellow oil.

¹H NMR (400 MHz, CDCl₃) δ7.11–7.09 (m, 2H), 6.93 (d, J=8.51 Hz, 1H), 6.81–6.79 (m, 2H), 6.77–6.73 (m, 1H), 6.71–6.69 (m, 2H), 4.16 (br s, 2H), 3.91–3.87 (m, 1H), 3.79 (s, 3H), 3.47–3.40 (m, 1H), 3.10–2.94 (m, 3H), 2.86–2.77 (m, 5H), 1.86 (s, 4H); MS m/e 449 (M++1).

EXAMPLE 3

2,2,2-Trifluoro-1-{6-hydroxy-1-[4-(2-pyrrolidin-1-yl-ethoxy)phenyl]-3,4-dihydro-1H-isoquinolin-2yl}ethanone A 1M solution of BBr₃ in CH₂Cl₂ (35.0 ml, 35.0 mmol) was added slowly to a solution of 2,2,2-trifluoro-1-{6-methoxy-1-[4-(2-pyrrolidin-1-yl-ethoxy)phenyl]-3,4-dihydro-1H-isoquinolin-2-yl}ethanone (6.26 g, 14.0 mmol) in anhydrous CH₂Cl₂ (400 ml) at 0° C. under N₂. The reaction mixture was warmed to rt and stirred at rt for 21 hr. MeOH (100 ml) was slowly added with stirring and the resulting solution was concentrated in vacuo to a red oil. Purification by flash chromatography, eluting with EtOAc-:MeOH (8:2), gave 1.886 g (31% yield) of yellow solid.

¹H NMR (400 MHz, CDCl₃) δ7.07 (d, J=8.30 Hz, 2H), 6.79 (d, J=8.30 Hz, 1H), 6.71–6.63 (m, 5H), 4.24 (br s, 2H), 3.85–3.81 (m, 1H), 3.37–3.31 (m, 1H), 3.20–2.95 (m, 7H), 2.71–2.66 (m, 1H), 1.98 (s, 4H); MS m/e 435 (M⁺+1).

EXAMPLE 4

{6-Hydroxy-1-[4-(2-pyrrolidin-1-yl-ethoxy)phenyl]-3,4-dihydro-1H-isoquinolin-2-yl}-phenylmethanone A mixture of {6-benzyloxy-1-[4-(2-pyrrolidin-1-yl-ethoxy)-phenyl]-3,4-dihydro-1H-isoquinolin-2-yl}phenylmethanone (0.043 g, 0.08 mmol), ammonium formate (0.127 g, 2.01 mmol), and 20% Pd(OH)₂/C (0.025 g) in MeOH (10 ml) was refluxed under N₂ for 1 hr, then filtered through Celite. The filtrate was evaporated in vacuo to a white residue that was dissolved in CH₂Cl₂ (10 ml) and washed with 1M NaOH (5 ml). The aqueous layer was extracted with CH₂Cl₂ (3×10 ml) and all of the combined organic solutions were dried over MgSO₄ and concentrated in vacuo to give 0.028 g (78% yield) of colorless residue.

¹H NMR (400 MHz, CDCl₃) δ7.38–7.34 (m, 6H), 7.18 (d, J=7.48 Hz), 6.91–6.62 (m, 6H), 4.24–4.22 (m, 2H), 3.72–3.52 (m, 1H), 3.26–2.89 (m, 8H), 2.56–2.52 (m, 1H), 1.95 (br s, 4H); MS m/e 443 (M⁺+1).

EXAMPLE 5

1-{6-Hydroxy-1-[4-(2-pyrrolidin-1-yl-ethoxy)phenyl]-3,4-dihydro-1H-isoquinolin-2-yl}2,2-dimethylpropan-1-one A mixture of 1-{6-benzyloxy-1-[4-(2-pyrrolidin-1-yl-ethoxy)phenyl]-3,4-dihydro-1H-isoquinolin-2yl}-2,2-dimethylpropan-1one, ammonium formate (0.033 g, 0.52 mmol), and 20% Pd(OH)₂/C (0.002 g) in MeOH (10 ml) was refluxed under N₂ for 1.5 hr, then filtered to remove the catalyst. The filtrate was evaporated in vacuo to a residue that was suspended in H₂O (0.4 ml) and saturated NaHCO₃ (0.4 ml). The aqueous mixture was extracted with CH₂Cl₂ (3×0.8 ml) and all of the combined organic solutions were evaporated to give the crude product. Purification by reverse-phase HPLC on a Primesphere C-18HC (50.0 mm×10.0 mm column with 5 m particle size) column, eluting with a linear gradient starting at time 0 min. of H₂O:CH₃CN:1% TFA/H₂O (85:10:5), increasing to H₂O:CH₃CN:1% TFA/H₂O (5:90:5) at 8 min., detected on a Micromass Platform 2 mass spectrometer (DAD 190–600 nM) gave material which, after evaporation to dryness, was purified by reverse-phase HPLC on a Primesphere C-18HC (3.0 mm×2.0 mm column with 5 m particle size) column, eluting with a linear gradient starting at time 0 min. of $H_2O:CH_3CN:TFA$ (99.9:0:0.1), increasing to $H_2O:CH_3CN:TFA$ (0:99.9:0.1) at 4 min., detected with a UV detector (300 nM +/−90 nM and 254 nM +/−25 nM), gave an eluent that was evaporated to dryness to give the pure product.

MS m/e 423 ($M^++1$).

EXAMPLE 6

Cyclohexyl-{6-hydroxy-1-[4-(2-pyrrolidin-1-yl-ethoxy)phenyl]-3,4-dihydro-1H-isoquinolin-2-yl}methanone The title compound was prepared in a two-step sequence. The first step was performed by analogy to Preparation 8, except that trimethylacetyl chloride was replaced with cyclohexanecarbonyl chloride.

MS m/e 539 ($M^++1$).

The second step was performed by analogy to Example 5.
MS m/e 449 ($M^++1$).

EXAMPLE 7

1-{6-Hydroxy-1-[4-(2-pyrrolidin-1-yl-ethoxy)-phenyl]-3,4-dihydro-1H-isoquinolin-2-yl}3-phenyl-propan-1one The title compound was prepared in a two-step sequence. The first step was performed by analogy to Preparation 8, except that trimethylacetyl chloride was replaced with cinnamoyl chloride.

MS m/e 559 ($M^++1$).

The second step was performed by analogy to Example 5.
MS m/e 471 ($M^++1$).

EXAMPLE 8

1-{6-Hydroxy-1-[4-(2-pyrrolidin-1-yl-ethoxy)phenyl]-3,4-dihydro-1H-isoquinolin-2-yl}octan-1-one The title compound was prepared in a two-step sequence. The first step was performed by analogy to Preparation 8, except that trimethylacetyl chloride was replaced with octanoyl chloride.

MS m/e 555 ($M^++1$).

The second step was performed by analogy to Example 5.
MS m/e 465 ($M^++1$).

EXAMPLE 9

{6-Hydroxy-1-[4-(2-pyrrolidin-1-yl-ethoxy)phenyl]-3,4-dihydro-1H-isoquinolin-2-yl}naphthalen-1-yl-methanone The title compound was prepared in a two-step sequence. The first step was performed by analogy to Preparation 8, except that trimethylacetyl chloride was replaced with 1-naphthoyl chloride.

MS m/e 583 ($M^++1$).

The second step was performed by analogy to Example 5.
MS m/e 493 ($M^++1$).

EXAMPLE 10

{6-Hydroxy-1-[4-(2-pyrrolidin-1-yl-ethoxy)phenyl]-3,4-dihydro-1H-isoquinolin-2-yl}-(3-methoxyphenyl)methanone The title compound was prepared in a two-step sequence. The first step was performed by analogy to Preparation 8, except that trimethylacetyl chloride was replaced with 3-methoxybenzoyl chloride.

MS m/e 563 ($M^++1$).

The second step was performed by analogy to Example 5.
MS m/e 473 ($M^++1$).

EXAMPLE 11

3-Cyclopentyl-1-{6-hydroxy-1-[4-(2-pyrrolidin-1-yl-ethoxy)phenyl]-3,4-dihydro-1H-isoquinolin-2-yl}propan-1-one The title compound was prepared in a two-step sequence. The first step was performed by analogy to Preparation 8, except that trimethylacetyl chloride was replaced with 3-cyclopentylpropionyl chloride.

MS m/e 553 ($M^++1$).

The second step was performed by analogy to Example 5.
MS m/e 463 ($M^++1$).

EXAMPLE 12

1-{6-Hydroxy-1-[4-(2-pyrrolidin-1-yl-ethoxy)-phenyl]-3,4-dihydro-1H-isoquinolin-2-yl}-2,2-diphenyl-ethanone The title compound was prepared in a two-step sequence. The first step was performed by analogy to Preparation 8, except that trimethylacetyl chloride was replaced with diphenylacetyl chloride.

MS m/e 633 ($M^++1$).

The second step was performed by analogy to Example 5.
MS m/e 533 ($M^++1$).

EXAMPLE 13

2,2,2-Trifluoro-1-[6-hydroxy-1-(4-hydroxyphenyl)-3,4-dihydro-1H-isoquinolin-2-yl]ethanone A 1M solution of $BBr_3$ in $CH_2Cl_2$ (6.0 ml, 6.0 mmol) was added slowly to a solution of 1-[1-(4-benzyloxyphenyl)-6-methoxy-3,4-dihydro-1H-isoquinolin-2-yl]-2,2,2-trifluoroethanone (1.054 g, 2.4 mmol) in anhydrous $CH_2Cl_2$ (100 ml) at 0° C. under $N_2$. The reaction mixture was warmed to rt and stirred at rt for 17 hr. MeOH (50 ml) was slowly added with stirring and the resulting solution was concentrated in vacuo to a red oil. This was dissolved in MeOH (20 ml) and 1M HCl (20 ml), and the resulting solution was stirred at rt for 4 hr, then neutralized with saturated $NaHCO_3$ solution (60 ml). The resulting suspension was concentrated in vacuo and the remaining material was extracted with EtOAc (4×30 ml). The combined extracts were dried over $MgSO_4$ and evaporated in vacuo to give 0.775 g of crude brown solid. Purification by flash chromatography, eluting with hexane:EtOAc (1:1) gave 0.080 g (10% yield) of white solid.

$^1$H NMR (400 MHz, CDCl$_3$) δ7.06 (d, J=8.72 Hz, 2H), 6.88 (d, J=8.30 Hz, 1H), 6.74–6.66 (m, 5H), 3.84–3.81 (m, 1H), 3.45–3.40 (m, 1H), 3.02–2.94 (m, 1H), 2.77–2.73 (m, 1H); MS m/e 336 (M+−1).

EXAMPLE 14

2,2,2-Trifluoro-1-[6-hydroxy-1-(4-hydroxyphenyl)-3,4-dihydro-1H-isoquinolin-2-yl]-ethanone The racemic material obtained in Example 13 (0.72 g) was separated on a Chiralpak AD® column (Chiral Technologies, Inc., Exton, Pa.), eluting with hexane: isopropanol (9:1) to give the two separate enantiomers. The enantiomer with a retention time of 14.1 minutes was collected and evaporated in vacuo to give 0.018 g (25% recovery) of white solid.

$^1$H NMR (400 MHz, CDCl$_3$) δ7.06 (d, J=8.72 Hz, 2H), 6.88 (d, J=8.30 Hz, 1H), 6.74–6.66 (m, 5H), 3.84–3.81 (m, 1H), 3.45–3.40 (m, 1H), 3.02–2.94 (m, 1H), 2.77–2.73 (m, 1H); MS m/e 336 (M+−1).

EXAMPLE 15

2,2,2-Trifluoro-1-[1-(4-hydroxyphenyl)-3,4-dihydro-1H-isoquinolin-2-yl]ethanone

A mixture of 1-[1-(4-benzyloxyphenyl)-3,4-dihydro-1H-isoquinolin-2-yl]-2,2,2-trifluoroethanone (0.144 g, 0.35 mmol), ammonium formate (0.441 g, 7.00 mmol), and 20% Pd(OH)$_2$/C (0.100 g) in MeOH (50 ml) was refluxed under N$_2$ for 1.5 hr, then filtered through Celite. The filtrate was evaporated in vacuo to a yellow residue that was suspended in a mixture of H$_2$O (15 ml) and saturated NaHCO$_3$ solution (15 ml), then extracted with CHCl$_3$ (4×15 ml). The combined organic extracts were dried over MgSO$_4$ and concentrated in vacuo to give 0.115 g of colorless oil. Purification by flash chromatography, eluting with hexane:EtOAc (8:2) gave 0.100 g (89% yield) of colorless oil.

$^1$H NMR (400 MHz, CDCl$_3$) δ7.29–7.16 (m, 4H), 7.09–7.00 (m, 3H), 6.77–6.72 (m, 2H), 3.96–3.91 (m, 1H), 3.52–3.44 (m, 1H), 3.14–3.05 (m, 1H), 2.90–2.86 (m, 1H); MS m/e 320 (M+−1).

EXAMPLE 16

2,2,2-Trifluoro-1-[1-(4-hydroxyphenyl)-3,4-dihydro-1H-isoquinolin-2-yl]ethanone

The racemic material obtained in Example 15 (0.80 g) was separated on a Chiralpak AD column, eluting with hexane:isopropanol (9:1) to give the two separate enantiomers. The enantiomer with a retention time of 9.7 minutes was collected and evaporated in vacuo to give 0.030 g (38% recovery) of white solid.

$^1$H NMR (400 MHz, CDCl$_3$) δ7.29–7.16 (m, 4H), 7.09–7.00 (m, 3H), 6.77–6.72 (m, 2H), 3.95–3.91 (m, 1H), 3.51–3.43 (m, 1H), 3.14–3.05 (m, 1H), 2.90–2.85 (m, 1H); MS m/e 320 (M+−1).

EXAMPLE 17

2,2,2-Trifluoro-1-[1-(4-hydroxyphenyl)-6-(2-pyrrolidin-1-yl-ethoxy)-3,4-dihydro-1H-isoquinolin-2yl]ethanone A solution of 1M TBAF in THF (2.8 ml, 2.82 mmol) and toluene-4-sulfonic acid 4-[6-(2-pyrrolidin-1-yl-ethoxy)-2-trifluoroacetyl-1,2,3,4-tetrahydroisoquinolin-1-yl]phenyl ester (0.415 g, 0.71 mmol) in anhydrous THF (50 ml) was refluxed under N$_2$ for 18 hr, then concentrated in vacuo to a green oil. This was suspended in sat. NaHCO$_3$ solution (25 ml), then extracted with EtOAc (3×40 ml). The combined extracts were dried over MgSO$_4$ and concentrated in vacuo to give 0.566 g of green oil. Purification by flash chromatography, eluting with EtOAc:MeOH (8:2) gave 0.241 g (79% yield) of yellow oil.

$^1$H NMR (400 MHz, CDCl$_3$) δ7.06–6.99 (m, 2H), 6.94–6.87 (m, 1H), 6.83 (d, J=8.51 Hz, 1H), 6.71 (d, J=8.51 Hz, 1H), 6.66 (m, 1H), 6.64–6.57 (m, 2H), 4.23–4.21 (m, 2H), 3.90–3.85 (m, 1H), 3.46–3.35 (m, 1H), 3.13 (s, 2H), 3.05–2.95 (m, 5H), 2.79–2.74 (m, 1H), 1.95 (s, 4H); MS m/e 435 (M$^+$+1).

EXAMPLE 18

2,2,2-Trifluoro-1-[1-(4-iodophenyl)-6-methoxy-3,4-dihydro-1H-isoquinolin-2-yl]ethanone Trifluoroacetic anhydride (1.76 g, 8.36 mmol) was added to a solution of 1-(4-iodophenyl)-6-methoxy-1,2,3,4-tetrahydroisoquinoline (2.35 g, 6.44 mmol) and Et$_3$N (1.0 ml, 7.1 mmol) in anhydrous CH$_2$Cl$_2$ (50 ml) at 0° C. under N$_2$. The resulting yellow solution was stirred at 0° C. for 2 hr, then washed first with 1M HCl (2×25 ml) followed by 50% saturated NaHCO$_3$ solution (2×25 ml), dried over Na$_2$SO$_4$, and concentrated in vacuo to give a yellow oil. Purification by flash chromatography, eluting with hexane:EtOAc (6:1) gave 1.87 g (63% yield) of yellow oil.

$^1$H NMR (400 MHz, CDCl$_3$) δ7.62 (d, J=8.31 Hz, 2H), 6.97–6.91 (m, 3H), 6.79–6.76 (m, 1H), 6.71–6.69 (m, 2H), 3.95–3.91 (m, 1H), 3.81 (s, 3H), 3.45–3.37 (m, 1H), 3.07–3.02 (m, 1H), 2.87–2.81 (m, 1H); MS m/e 460 (M$^+$−1).

EXAMPLE 19

2,2,2-Trifluoro-1-[6-hydroxy-1-(4-iodophenyl)-3,4-dihydro-1H-isoquinolin-2-yl]ethanone A 1M solution of BBr$_3$ in CH$_2$Cl$_2$ (0.49 ml, 0.49 mmol) was added slowly to a solution of 2,2,2-trifluoro-1-[1-(4-iodophenyl)-6-methoxy-3,4-dihydro-1H-isoquinolin-2-yl]ethanone (0.150 g, 0.33 mmol) in anhydrous CH$_2$Cl$_2$ (10 ml) at 0° C. under N$_2$. The reaction mixture was stirred at 0° C. for 1 hr, then warmed to rt and stirred at rt for 19 hr. MeOH (10 ml) was slowly added with stirring and the resulting solution was concentrated in vacuo to a yellow oil. Purification by flash chromatography, eluting with hexane:EtOAc (8:2) gave 0.121 g (83% yield) of yellow solid.

$^1$H NMR (400 MHz, CDCl$_3$) δ7.62 (d, J=8.51 Hz, 2H), 6.94 (d, J=8.51 Hz, 2H), 6.87 (d, J=8.30 Hz, 1H), 6.71–6.68 (m, 3H), 3.94–3.89 (m, 1H), 3.44–3.36 (m, 1H), 3.08–2.99 (m, 1H), 2.83–2.78 (m, 1H), MS m/e 446 (M$^+$−1).

EXAMPLE 20

1-(1-Cyclohexyl-6-methoxy-3,4-dihydro-1H-isoquinolin-2-yl)-2,2,2-trifluoroethanone Trifluoroacetic anhydride (0.128 g, 0.61 mmol) was added to a solution of 1-cyclohexyl-6-methoxy-1,2,3,4-tetrahydroisoquinoline (0.150 g, 0.61 mmol) and Et$_3$N (0.17 ml, 0.1.22 mmol) in anhydrous CH$_2$Cl$_2$ (20 ml) at 0° C. under N$_2$. The resulting yellow solution was stirred at rt for 22 hr, washed first with 1M HCl (5 ml) then 1M NaHCO$_3$ (5 ml), dried over MgSO$_4$, and concentrated in vacuo to give 0.248 g of yellow oil. Purification by flash chromatography, eluting with hexane:EtOAc (19:1) gave 0.198 g (95% yield) of yellow oil.

$^1$H NMR (400 MHz, CDCl$_3$) δ7.02 (d, J=8.51 Hz, 1H), 6.72 (dd, J=8.51 Hz, J=2.70) Hz, 1H), 6.65 (d, J=2.49 Hz, 1H), 5.16 (d, J=9.13 Hz, 1H), 3.97–3.94 (m, 1H), 3.77 (s,

3H), 3.75–3.68 (m, 1H), 3.09–2.88 (m, 2H), 1.75 (br s, 4H), 1.11–1.02 (m, 5H);

MS m/e 342 (M$^+$+1).

Example 21

1-(1-Cyclohexyl-6-hydroxy-3,4-dihydro-1H-isoquinolin-2-yl)-2,2,2-trifluoroethanone A 1M solution of BBr$_3$ in CH$_2$Cl$_2$ (0.77 ml, 0.77 mmol) was added slowly to a solution of 1-(1-cyclohexyl-6-methoxy-3,4-dihydro-1H-isoquinolin-2-yl)-2,2,2-trifluoroethanone (0.176 g, 0.52 mmol) in anhydrous CH$_2$Cl$_2$ (10 ml) at 0° C. under N$_2$. The reaction mixture was stirred at 0° C. for 30 min, then warmed to rt and stirred at rt for 21 hr. MeOH (10 ml) was slowly added with stirring and the resulting solution was concentrated in vacuo to a orange oil. Purification by flash chromatography, eluting with hexane:EtOAc (8:2) gave 0.193 g (100% yield) of white solid.

$^1$H NMR (400 MHz, CDCl$_3$) δ6.97 (d, J=8.52 Hz, 1H), 6.66–6.60 (m, 3H), 5.15 (d, J=8.93 Hz, 1H), 4.69 (br s, 1H), 3.97–3.94 (m, 1H), 3.75–3.67 (m, 1H), 3.04–2.87 (m, 3H), 1.75 (br s, 4H), 1.12–1.10 (m, 5H); MS m/e 326 (M$^+$–1).

EXAMPLE 22

2,2,2-Trifluoro-1-(6-methoxy-1-phenyl-3,4-dihydro-1H-isoquinolin-2-yl)ethanone

Trifluoroacetic anhydride (0.089 ml, 0.627 mmol) was added to a solution of 6-methoxy-1-phenyl-1,2,3,4-tetrahydoisoquinoline (0.150 g, 0.627 mmol) and Et$_3$N (0.174 ml, 1.25 mmol) in anhydrous CH$_2$Cl$_2$ (20 ml) at 0° C. under N$_2$. The resulting solution was warmed to rt and stirred at rt for 68 hr, washed with 1M HCl (5 ml), then with sat. NaHCO$_3$ solution (5 ml), dried over MgSO$_4$, and concentrated in vacuo to give 0.216 g of colorless oil. Purification by flash chromatography, eluting with hexane:EtOAc (19:1) gave 0.188 g (89% yield) of colorless oil.

$^1$H NMR (400 MHz, CDCl$_3$) δ7.30–7.28 (m, 3H), 7.21–7.18 (m, 2H), 6.96 (d, J=8.72 Hz, 1H), 6.79–6.76 (m, 2H), 6.72 (s, 1H), 3.93–3.90-(m, 1H), 3.81 (s, 3H), 3.50–3.42 (m, 1H), 3.08–3.03 (m, 1H), 2.86–2.82 (m, 1H); MS m/e 334 (M$^+$–1).

EXAMPLE 23

2,2,2-Trifluoro-1-(6-hydroxy-1-phenyl-3,4-dihydro-1H-isoquinolin-2-yl)ethanone

A 1M solution of BBr$_3$ in CH$_2$Cl$_2$ (0.77 ml, 0.77 mmol) was added slowly to a solution of 2,2,2-trifluoro-1-(6-methoxy-1-phenyl-3,4-dihydro-1H-isoquinoline-2-yl) ethanone (0.172 g, 0.513 mmol) in anhydrous CH$_2$Cl$_2$ (10 ml) at 0° C. under N$_2$. The resulting yellow solution was stirred at 0° C. for 30 min, then warmed to rt and stirred at rt for 22 hr. MeOH (5 ml) was slowly added to the reaction mixture with stirring and the resulting solution was concentrated in vacuo to give 0.242 g of yellow oil. Purification by flash chromatography, eluting with hexane:EtOAc (8:2) gave 0.143 g (87% yield) of white solid.

$^1$H NMR (400 MHz, CDCl$_3$) δ7.30–7.27 (m, 3H), 7.20–7.17 (m, 2H), 6.91 (d, J=8.09 Hz, 1H), 6.76 (s, 1H), 6.70–6.74 (m, 2H), 4.76 (br s, 1H), 3.92–3.88 (m, 1H), 3.49–3.41 (m, 1H), 3.09–2.97 (m, 1H), 2.83–2.79 (m, 1H); MS m/e 320 (M$^+$–1).

EXAMPLE 24

2,2,2-Trifluoro-1-(6-methoxy-1-thiophen-2-yl-3,4-dihydro-1H-isoquinolin-2-yl)ethanone Trifluoroacetic anhydride (0.70 ml, 4.97 mmol) was added to a solution of 6-methoxy-1-thiophen-2-yl-1,2,3,4-tetrahydroisoquinoline (1.220 g, 4.97 mmol) and Et$_3$N (1.39 ml, 9.94 mmol) in anhydrous CH$_2$Cl$_2$ (40 ml) at 0° C. under N$_2$. The resulting solution was warmed to rt and stirred at rt for 68 hr, washed with 1M HCl (20 ml) followed by sat. NaHCO$_3$ solution (20 ml), dried over MgSO$_4$, then concentrated in vacuo to give 1.863 g of red oil. Purification by flash chromatography, eluting with hexane:EtOAc (19:1) gave 1.340 g (79% yield) of yellow oil.

$^1$H NMR (400 MHz, CDCl$_3$) δ7.24–7.23 (m, 1H), 7.09 (d, J=8.72 Hz, 1H), 6.92–6.90 (m, 1H), 6.84–6.83 (m, 2H), 6.83–6.77 (m, 1H), 6.69 (s, 1H), 3.98–3.95 (m, 1H), 3.81 (s, 3H), 3.62–3.55 (m, 1H), 3.11–3.02 (m, 1H), 2.88–2.84 (m, 1H); MS m/e 340 (M$^+$–1).

EXAMPLE 25

2,2,2-Trifluoro-1-(6-hydroxy-1-thiophen-2-yl-3,4-dihydro-1H-isoquinolin-2-yl)ethanone A 1M solution of BBr$_3$ in CH$_2$Cl$_2$ (0.66 ml, 0.66 mmol) was added slowly to a solution of 2,2,2-trifluoro-1-(6-methoxy-1-thiophen-2-yl-3,4-dihydro-1H-isoquinolin-2-yl) ethanone (0.150 g, 0.439 mmol) in anhydrous CH$_2$Cl$_2$ (10 ml) at 0° C. under N$_2$. The resulting red solution was stirred at 0° C. for 30 min, then warmed to rt and stirred at rt for 20 hr. MeOH (5 ml) was slowly added to the reaction mixture with stirring and the resulting solution was concentrated in vacuo to give 0.138 g of a black residue. Purification by flash chromatography, eluting with hexane:EtOAc (8:2) gave 0.006 g (4% yield) of white solid.

$^1$H NMR (400 MHz, CDCl$_3$) δ7.24 (s, 1H), 7.04 (d, J=8.72 Hz, 1H), 6.90–6.89 (m, 1H), 6.82 (m, 2H), 6.69 (d, J=8.92 Hz, 1H), 6.65 (s, 1H), 3.96–3.93 (m, 1H), 3.60—3.54 (m, 1H), 3.03–3.00 (m, 1H), 2.84–2.80 (m, 1H); MS m/e 326 (M$^+$–1).

EXAMPLE 26

1-[1-(4-Bromophenyl)-6-methoxy-3,4-dihydro-1H-isoquinolin-2-yl]-2,2,2-trifluoroethanone Trifluoroacetic anhydride (0.067 ml, 0.471 mmol) was added to a solution of 1-(4-bromophenyl)-6-methoxy-1,2,3,4-tetrahydroisoquinoline (0.150 g 0.471 mmol) and Et$_3$N (0.13 ml, 0.942 mmol) in anhydrous CH$_2$Cl$_2$ (20 ml) at 0° C. under N$_2$. The resulting solution was warmed to rt and stirred at rt for 68 hr, washed with 1M HCl (5 ml) and then with sat. NaHCO$_3$ solution (5 ml), dried over MgSO$_4$, and concentrated in vacuo to give 0.220 g of yellow oil. Purification by flash chromatography, eluting with hexane:EtOAc (19:1) gave 0.181 g (93% yield) of white solid.

$^1$H NMR (400 MHz, CDCl$_3$) δ7.41 (d, J=8.51 Hz, 2H), 7.07 (d, J=8.51 Hz, 2H), 6.91 (d, J=8.51 Hz, 1H), 6.77 (dd, J=8.30 Hz, J=2.49 Hz, 1H), 6.70 (s, 2H), 3.93–3.81 (m, 1H), 3.80 (s, 3H), 3.44–3.67 (m, 1H), 3.11–3.02 (m, 1H), 2.85–2.82 (m, 1H); MS m/e 412, 414 bromine isotope pattern (M$^+$–1).

EXAMPLE 27

1-[1-(4-Bromophenyl)-6-hydroxy-3,4-dihydro-1H-isoquinolin-2-yl]-2,2,2-trifluoroethanone A 1M solution of BBr$_3$ in CH$_2$Cl$_2$ (0.61 ml, 0.61 mmol) was added slowly to a solution of 1-[1-(4-bromophenyl)-6-methoxy-3,4-dihydro-1H-isoquinolin-2-yl]-2,2,2-trifluoroethanone (0.168 g, 0.406 mmol) in anhydrous CH$_2$Cl$_2$ (10 ml) at 0° C. under N$_2$. The resulting orange solution was stirred at 0° C. for 30 min, then warmed to rt and stirred at rt for 21 hr. MeOH (5 ml) was slowly added to the reaction mixture with stirring and the resulting solution was concentrated in vacuo to give 0.201 g of yellow residue. Purification by flash chromatography, eluting with hexane:EtOAc (8:2) gave 0.149 g (92% yield) of white solid.

$^1$H NMR (400 MHz, CDCl$_3$) δ7.44–7.41 (m, 2H), 7.09–7.07 (m, 2H), 6.88 (d, J=8.10 Hz, 1H), 6.71–6.68 (m, 3H), 3.94–3.90 (m, 1H), 3.43–3.36 (m, 1H), 3.09–2.98 (m, 1H), 2.83–2.79 (m, 1H); MS m/e 400, 398 bromine isotope pattern (M$^+$−1).

EXAMPLE 28

2-Benzenesulfonyl-1-[4-(2-pyrrolidin-1-yl-ethoxy) phenyl]-1,2,3,4-tetrahydroisoquinolin-6-ol A mixture of 2-benzenesulfonyl-6-benzyloxy-1-[4-(2-pyrrolidin-1-yl-ethoxy)phenyl]-1,2,3,4-tetrahydroisoquinoline (0.043 g, 0.08 mmol), ammonium formate (0.096 g, 1.52 mmol), and 20% Pd(OH)$_2$/C (0.025 g) in MeOH (10 ml) was refluxed under N$_2$ for 1 hr, then filtered through Celite. The filtrate was evaporated in vacuo to a white residue that was dissolved in CH$_2$Cl$_2$ (10 ml) and washed with 1M NaOH (5 ml). The aqueous layer was extracted with CH$_2$Cl$_2$ (3×10 ml), and all of the combined organic solutions were dried over MgSO$_4$ and concentrated in vacuo to give 0.026 g (72% yield) of colorless residue.

$^1$H NMR (400 MHz, CDCl$_3$) δ7.65 (d, J=8.09 Hz, 4H), 7.40–7.38 (m, 2H), 7.29 (d, J=7.47 Hz, 4H), 6.73 (d, J=8.51 Hz, 2H), 6.68 (d, J=8.09 Hz, 2H), 6.56 (d, J=9.13 Hz, 1H), 6.37 (s, 1H), 6.09 (s, 1H), 4.21 (br s, 2H), 3.69–3.65 (m, 1H), 3.17–3.13 (m, 4H), 2.48–2.44 (m, 1H), 2.35–2.29 (m, 1H), 1.96 (br s, 4H); MS m/e 479 (M$^+$+1).

EXAMPLE 29

2-(Naphthalene-1-sulfonyl)-1-[4-(2-pyrrolidin-1-yl-ethoxy)phenyl]-1,2,3,4-tetrahydroisoquinolin-6-ol A mixture of 6-benzyloxy-2-(naphthalene-1-sulfonyl)-1-[4-(2-pyrrolidin-1-yl-ethoxy)-phenyl]-1,2,3,4-tetrahydroisoquinoline (0.012 g, 0.019 mmol), ammonium formate (0.033 g, 0.52 mmol), and 20% Pd(OH)$_2$/C (0.002 g) in MeOH (10 ml) was refluxed under N$_2$ for 1.5 hr, then filtered to remove the catalyst. The filtrate was evaporated in vacuo to a residue that was suspended in a mixture of H$_2$O (0.4 ml) and sat. NaHCO$_3$ (0.4 ml). The aqueous mixture was extracted with CH$_2$Cl$_2$ (3×0.8 ml), and all of the combined organic solutions were evaporated to give the crude product. Purification by reverse-phase HPLC, eluting with gradient Primesphere C-18HC (3.0 mm×2.0 mm column with 5 m particle size) column, eluting with a linear gradient starting at time 0 min. of H$_2$O:CH$_3$CN:TFA (99.9:0:0.1), increasing to H$_2$O CH$_3$CN:TFA (0:99.9:0.1) at 4 min., detected with a UV detector (300 nM +/−90 nM and 254 nM +/−25 nM), gave an eluent that was evaporated to dryness to give the named product. MS m/e 493 (M$^+$+1).

EXAMPLE 30

2-Phenylmethanesulfonyl-1-[4-(2-pyrrolidin-1-yl-ethoxy)phenyl]-1,2,3,4-tetrahydroisoquinolin-6-ol The title compound was prepared in a two-step sequence. The first step was performed by analogy to Preparation 32, except that 1-naphthalenesulfonyl chloride was replaced with α-toluenesulfonyl chloride.

MS m/e 583 (M$^+$+1).

The second step was performed by analogy to Example 29.

MS m/e 493 (M$^+$+1).

EXAMPLE 31

2-(Butane-1-sulfonyl)-1-[4-(2-pyrrolidin-1-yl-ethoxy)phenyl]-1,2,3,4-tetrahydroisoquinolin-6-ol The title compound was prepared in a two-step sequence. The first step was performed by analogy to Preparation 32, except that 1-naphthalenesulfonyl chloride was replaced with 1-butanesulfonyl chloride.

MS m/e 549 (M$^+$+1).

The second step was performed by analogy to Example 29.

MS m/e 459 (M$^+$+1).

EXAMPLE 32

2-Methanesulfonyl-1-[4-(2-pyrrolidin-1-yl-ethoxy) phenyl]-1,2,3,4-tetrahydroisoquinolin-6-ol The title compound was prepared in a two-step sequence. The first step was performed by analogy to Preparation 32, except that 1-naphthalenesulfonyl chloride was replaced with methanesulfonyl chloride.

MS m/e 507 (M$^+$+1).

The second step was performed by analogy to Example 29.

MS m/e 417 (M$^+$+1).

EXAMPLE 33

2-(4-Propylbenzenesulfonyl)-1-[4-(2-pyrrolidin-1-yl-ethoxy)phenyl]-1,2,3,4-tetrahydroisoquinolin-6-ol The title compound was prepared in a two-step sequence. The first step was performed by analogy to Preparation 32, except that 1-naphthalenesulfonyl chloride was replaced with p-n-propylbenzenesulfonyl chloride.

MS m/e 611 (M$^+$+1).

The second step was performed by analogy to Example 29.

MS m/e 521 (M$^+$+1).

EXAMPLE 34

2-(4-Isopropylbenzenesulfonyl)-1-[4-(2-pyrrolidin-1-yl-ethoxy)phenyl]-1,2,3,4-tetrahydroisoquinolin-6-ol The title compound was prepared in a two-step sequence. The first step was performed by analogy to Preparation 32, except that 1-naphthalenesulfonyl chloride was replaced with 4-isopropylbenzenesulfonyl chloride.

MS m/e 611 (M$^+$+1).

The second step was performed by analogy to Example 29.

MS m/e 521 (M$^+$+1).

EXAMPLE 35

1-[4-(2-Pyrrolidin-1-yl-ethoxy)phenyl]-2-(toluene-4-sulfonyl)-1,2,3,4-tetrahydroisoquinolin-6-ol The title compound was prepared in a two-step sequence. The first step was performed by analogy to Preparation 32, except that 1-naphthalenesulfonyl chloride was replaced with 4-methylbenzenesulfonyl chloride.

MS m/e 583 (M$^+$+1).

The second step was performed by analogy to Example 29.

MS m/e 493 (M$^+$+1).

EXAMPLE 36

2-(1-Methyl-1H-imidazole-4-sulfonyl)-1-[4-(2-pyrrolidin-1-yl-ethoxy)phenyl]-1,2,3,4-tetrahydroisoquinolin-6-ol The title compound was prepared in a two-step sequence. The first step was performed by analogy to Preparation 32, except that 1-naphthalenesulfonyl chloride was replaced with 1-methylimidazolesulfonyl chloride.

MS m/e 573 (M$^+$+1).

The second step was performed by analogy to Example 29.

MS m/e 483 (M$^+$+1).

EXAMPLE 37

N-(4-{6-Hydroxy-1-[4-(2-pyrrolidin-1-yl-ethoxy)phenyl]-3,4-dihydro-1H-isoquinoline-2-sulfonyl}phenyl)acetamide The title compound was prepared in a two-step sequence. The first step was performed by analogy to Preparation 32, except that 1-naphthalenesulfonyl chloride was replaced with p-acetamidobenzenesulfonyl chloride.

MS m/e 626 (M$^+$+1).

The second step was performed by analogy to Example 29.

MS m/e 536 (M$^+$+1).

EXAMPLE 38

4-Amino-3-{6-hydroxy-1-[4-(2-pyrrolidin-1-yl-ethoxy)phenyl]-3,4-dihydro-1H-isoquinoline-2sulfonyl}pent-3-en-2-one A mixture of 6-benzyloxy-2-(3,5-dimethylisoxazole-4-sulfonyl)-1-[4-(2-pyrrolidin-1-yl-ethoxy)phenyl]-1,2,3,4-tetrahydroisoquinoline (0.036 g, 0.061 mmol), ammonium formate (0.077 g, 1.22 mmol), and 20% Pd(OH)$_2$/C (0.020 g) in MeOH (20 ml) was refluxed under N$_2$ for 1.5 hr, then filtered through Celite. The filtrate was evaporated in vacuo to a yellow residue that was suspended in a mixture of H$_2$O (3 ml) and sat. NaHCO$_3$ solution (3 ml), then extracted with CH$_2$Cl$_2$ (3×3 ml). The combined organic extracts were dried over MgSO$_4$ and concentrated in vacuo to give 0.023 g (76% yield) of yellow oil. Further purification by preparative TLC, eluting with SiO$_2$, EtOAc:MeOH (1:1), gave 0.019 g (63% yield) of colorless oil.

$^1$H NMR (400 MHz, CDCl$_3$) δ11.73–11.65 (m, 1H), 6.95–6.88 (m, 3H), 6.75 (d, J=8.52 Hz, 1H), 6.68 (d, J=8.10 Hz, 1H), 6.67–6.52 (m, 3H), 6.08 (br s, 1H), 5.80 (s, 1H), 4.05–4.02 (m, 2H), 3.55–3.52 (m, 1H), 3.10–2.97 (m, 2H), 2.90–2.84 (m, 1H), 2.79–2.63 (m, 4H), 2.50 (s, 1H), 2.37 (s, 3H), 2.34 (s, 3H), 1.84–1.79 (m, 4H); MS m/e 500 (M$^+$+1).

EXAMPLE 39

2-(3,5-Dimethylisoxazole-4-sulfonyl)-1-[4-(2-pyrrolidin-1-yl-ethoxy)phenyl]-1,2,3,4-tetrahydroisoquinolin-6-ol A 1M solution of BBr$_3$ in CH$_2$Cl$_2$ (0.095 ml, 0.095 mmol) was added slowly to a solution of 6-benzyloxy-2-(3,5-dimethylisoxazole-4-sulfonyl)-1-[4-(2-pyrrolidin-1-yl-ethoxy)phenyl]-1,2,3,4-tetrahydroisoquinoline (0.037 g, 0.063 mmol) in anhydrous CH$_2$Cl$_2$ (10 ml) at 0° C. under N$_2$. The reaction mixture was stirred at 0° C. for 1 hr, then warmed to rt and stirred at rt for 4 hr. MeOH (5 ml) was slowly added with stirring and the resulting solution was concentrated in vacuo to an orange residue. Purification by preparative TLC, eluting with EtOAc:MeOH (1:1), and then purification again by preparative TLC, eluting with EtOAc:MeOH (8:2), gave 0.011 g (35% yield) of white solid.

$^1$H NMR (400 MHz, CDCl$_3$) δ6.99 (d, J=8.72 Hz, 2H), 6.75 (d, J=8.51 Hz, 1H), 6.69 (d, J=8.72 Hz, 2H), 6.61 (dd, J=8.30 Hz, J=2.49 Hz, 1H), 6.51 (d, J=2.28 Hz, 1H), 6.01 (s, 1H), 4.25 (br s, 2H), 3.62–3.57 (m, 1H), 3.24–3.16 (m, 3H), 3.05 (br s, 4H), 2.66–2.57 (m, 1H), 2.52 (s, 3H), 2.47–2.42 (m, 1H), 2.18 (s, 3H), 2.00 (br s, 4H); MS m/e 498 (M$^+$+1).

EXAMPLE 40

2-(4-Imidazol-1-yl-benzyl)-1-[4-(2-pyrrolidin-1-yl-ethoxy)phenyl]-1,2,3,4-tetrahydroisoquinolin-6-ol A solution of 1-[4-(2-pyrrolidin-1-yl-ethoxy)phenyl]-1,2,3,4-tetrahydroisoquinolin-6-ol (0.023 g, 0.067 mmol), 4-imidazol-1-yl-benzaldehyde (0.011 g, 0.063 mmol), NaOAc (0.011 g, 0.14 mmol), and sodium cyanoborohydride (0.004 g, 0.063 mmol) in MeOH (2.0 ml) was stirred at rt for 18 hr. The reaction mixture was evaporated in vacuo to a yellow residue that was dissolved in EtOAc (5 ml) and washed first with sat. NaHCO$_3$ solution (5 ml) and then with H$_2$O (5 ml). The organic solution was dried over MgSO$_4$ and evaporated to give 0.035 g of yellow residue. Purification by preparative TLC, eluting with EtOAc:MeOH (7:3), gave 0.007 g (23% yield) of white solid.

MS m/e 495 (M$^+$+1).

EXAMPLE 41

2-Benzo[1,3]dioxol-5-yl-methyl-1-[4-(2-pyrrolidin-1-yl-ethoxy)phenyl]-1,2,3,4-tetrahydroisoquinolin-6-ol The title compound was prepared by analogy to Example 40, except that 3,4-(methylenedioxy)benzaldehyde was used in place of 4-imidazol-1-yl-benzaldehyde.

MS m/e 473 (M$^+$+1).

EXAMPLE 42

1-[4-(2-Pyrrolidin-1-yl-ethoxy)phenyl]-2-(tetrahydropyran-4-yl)-1,2,3,4-tetrahydroisoquinolin-6-ol The title compound was prepared by analogy to Example 40, except that tetrahydro-4H-pyran-4-one was used in place of 4-imidazol-1-yl-benzaldehyde.

$^1$H NMR (400 MHz, CDCl$_3$) δ7.14 (d, J=8.52 Hz, 2H), 6.81–6.79 (m, 1H), 6.75 (d, J=8.52 Hz, 2H), 6.57 (s, 1H), 6.53–6.47 (m, 1H), 4.80 (s, 1H), 4.28 (br s, 2H), 4.00–3.97 (m, 1H), 3.91–3.89 (m, 1H), 3.26–3.18 (m, 5H), 3.11–3.08 (m, 2H), 2.73–2.65 (m, 3H), 2.00 (s, 6H), 1.80–1.77 (m, 3H), 1.60–1.57 (m, 2H), 1.43–1.20 (m, 1H);

MS m/e 423 (M$^+$+1).

EXAMPLE 43

2-(4,4-Dimethylcyclohexyl)-1-[4-(2-pyrrolidin-1-yl-ethoxy)phenyl]-1,2,3,4-tetrahydroisoquinolin-6-ol The title compound was prepared by analogy to Example 40, except that 4,4-dimethyl-2-cyclohexene-1-one was used in place of 4-imidazol-1-yl-benzaldehyde.

MS m/e 449 ($M^+$+1).

EXAMPLE 44

2-Cyclohexyl-1-[4-(2-pyrrolidin-1-yl-ethoxy)phenyl]-1,2,3,4-tetrahydroisoquinolin-6-ol The title compound was prepared by analogy to Example 40, except that cyclohexanone was used in place of 4-imidazol-1-yl-benzaldehyde.

MS m/e 421 ($M^+$+1).

EXAMPLE 45

2-Benzyl-1-[4-(2-pyrrolidin-1-yl-ethoxy)phenyl]-1,2,3,4-tetrahydroisoquinolin-6-ol The title compound was prepared by analogy to Example 40, except that benzaldehyde was used in place of 4-imidazol-1-yl-benzaldehyde.

$^1$H NMR (400 MHz, CDCl$_3$) δ7.33–7.21 (m, 9H), 6.76 (d, J=8.51 Hz, 1H), 6.55–6.47 (m, 2H), 4.45 (s, 1H), 4.19 (br s, 2H), 3.76 (d, J=13.70 Hz, 1H), 3.17 (d, J=13.70 Hz, 1H), 3.04–2.87 (m, 9H), 2.66 (d, J=16.39 Hz, 1H), 2.47–2.43 (m, 1H), 1.91 (br s, 4H); MS m/e 429 ($M^+$+1).

EXAMPLE 46

6-Hydroxy-1-[4-(2-pyrrolidin-1-yl-ethoxy)phenyl]-3,4-dihydro-1H-isoquinoline-2-carboxylic acid tert-butyl ester The title compound was prepared by analogy to Example 4, except that 6-benzyloxy-1-[4-(2-pyrrolidin-1-yl-ethoxy)-phenyl]-3,4-dihydro-1H-isoquinoline-2-carboxylic acid tert-butyl ester was used in place of {6-benzyloxy-1-[4-(2-pyrrolidin-1-yl-ethoxy)-phenyl]-3,4-dihydro-1H-isoquinolin-2-yl}phenylmethanone.

$^1$H NMR (400 MHz, CDCl$_3$) δ7.22–7.06 (m, 3H), 6.81–6.77 (m, 1H), 6.73 (d, J=8.72 Hz, 1H), 6.63–6.61 (m, 1H), 6.30–6.08 (m, 2H), 4.26 (br s, 2H), 3.97–3.93 (m, 1H), 3.17–2.84 (m, 8H), 2.60–2.56 (m, 1H), 1.98 (br s, 4H), 1.47 (s, 9H); MS m/e 439 ($M^+$+1).

EXAMPLE 47

6-Hydroxy-1-[4-(2-pyrrolidin-1-yl-ethoxy)phenyl]-3,4-dihydro-1H-isoquinoline-2-carboxylic acid ethyl ester The title compound was prepared by analogy to Example 4, except that 6-benzyloxy-1-[4-(2-pyrrolidin-1-yl-ethoxy)-phenyl]-3,4-dihydro-1H-isoquinoline-2-carboxylic acid ethyl ester was used in place of {6-benzyloxy-1-[4-(2-pyrrolidin-1-yl-ethoxy)-phenyl]-3,4-dihydro-1H-isoquinolin-2-yl}phenylmethanone.

$^1$H NMR (400 MHz, CDCl$_3$) δ7.16–7.14 (m, 1H), 7.03 (brs, 2H), 6.77 (d, J=8.51 Hz, 1H), 6.65 (d, J=8.72 Hz, 2H), 6.59–6.57 (m, 2H), 4.14 (br s, 4H), 3.96–3.90 (m, 2H), 3.10–3.03 (m, 3H), 2.84 (br s, 5H), 2.50 (d, J=16.19 Hz, 1H), 1.89 (br s, 4H), 1.26 (br s, 3H); MS m/e 411 ($M^+$+1).

EXAMPLE 48

1-(4-Hydroxy-phenyl)-2-phenyl-1,2,3,4-tetrahydroisoquinolin-6-ol

To a stirred solution of 6-methoxy-1-(4-methoxy-phenyl)-2-phenyl-1,2,3,4-tetrahydroisoquinoline (0.075 g, 0.217 mmol, 1.0 eq.) in CH$_2$Cl$_2$ (3 ml) cooled to −78° C. under an atmosphere of N$_2$ was added BBr$_3$ as a 1.0 M solution in CH$_2$Cl$_2$ (0.65 ml, 0.65 mmol, 3.0 eq.). The reaction was stirred overnight, slowly allowing the reaction mixture to warm to rt. The reaction was quenched with MeOH (2 ml) and stirring was continued for 1 hour. The mixture was diluted with EtOAc (20 ml), water (2 ml), and sat. NaHCO$_3$ (2 ml, until the pH of the aqueous layer was approximately 8). The layers were separated and the aqueous layer diluted with water (10 ml), then extracted with EtOAc (2×20 ml) and CH$_2$Cl$_2$ (2×20 ml). The combined organics were dried over MgSO$_4$, filtered, and concentrated in vacuo. The residue was subjected to flash chromatography (SiO$_2$, hexanes:EtOAc 3:2) to give the desired compound (0.053 g, 0.167 mmol, 77% yield).

$^1$H NMR (400 MHz, CDCl$_3$) δ$_H$ 2.85 (2H, m,) 3.41 (1H, m), 3.62 (1H, m), 5.74 (1H, s) 6.62–7.14 (12H, overlapping m).

EXAMPLE 49

1-Cyclohexyl-6-methoxy-2-phenyl-1,2,3,4-tetrahydroisoquinoline

A stirred solution of cyclohexanecarboxylic acid [2-(3-methoxy-phenyl)-ethyl]-phenyl-amide in POCl$_3$ under an atmosphere of N$_2$ was heated at reflux for 14 hours. The solution was allowed to cool to rt and concentrated in vacuo. The residue was taken up in CH$_2$Cl$_2$ (30 ml) and washed with sat. NaHCO$_3$ until CO$_2$ evolution ceased. The organic layer was dried over MgSO$_4$, filtered, and concentrated in vacuo. The residue was dissolved in MeOH (20 ml), cooled to 0° C., and NaBH$_4$ (0.105 g, 2.77 mmol) was added in a portionwise manner. The reaction was stirred for 2 hours at 0° C., then additional NaBH$_4$ (0.105 g, 2.77 mmol) was added. The reaction was stirred at rt overnight, diluted with CH$_2$Cl$_2$ (50 ml), and washed with sat. NaHCO$_3$ solution (1×50 ml). The organic layer was dried over MgSO$_4$, filtered, and concentrated in vacuo, to give the desired compound as a yellow oil (0.234 g, 0.729 mmol, 73% yield).

$^1$H NMR (400 MHz, CDCl$_3$) δ$_H$ 0.84–1.18 (6H, overlapping m,) 1.58–1.76 (4H, overlapping m), 1.95 (1H, m), 2.95 (2H, m), 3.43 (1H, m), 3.69 (1H, m), 3.76 (3H, s), 4.35 (1H, d, J 8.0 Hz), 6.64–7.23 (8H, overlapping m). MS 322 (M+1)

EXAMPLE 50

1-Cyclohexyl-2-phenyl-1,2,3,4-tetrahydroisoquinolin-6-ol

The title compound was prepared by analogy to Example 48 except that 1-cyclohexyl-6-methoxy-2-phenyl-1,2,3,4-tetrahydroisoquinoline was used instead of 6-methoxy-1-(4-methoxy-phenyl)-2-phenyl-1,2,3,4-tetrahydroisoquinoline, and hexanes:EtOAc 6:1 was used as eluent for flash chromatography purification.

$^1$H NMR (400 MHz, CDCl$_3$) δ$_H$ 0.90–1.15 (6H, overlapping m,) 1.60–1.70 (4H, overlapping m), 1.93 (1H, m), 2.90 (2H, m), 3.41 (1H, m), 3.66 (1H, m), 4.11 (1H, d, J 7.5 Hz), 4.98 (1H, broad s), 6.55–6.59 (2H, overlapping m), 6.65 (1H, t, J 7.0 Hz), 6.82 (2H, d, J 8.5 Hz), 6.90 (1H, d, J 8.0 Hz) and 7.17-7.23 (2H, overlapping m). MS 308 (M+1).

EXAMPLE 51

1-Isopropyl-6-methoxy-2-phenyl-1,2,3,4-tetrahydroisoquinoline

The title compound was prepared by analogy to Preparation 65 except that N-[2-(3-methoxy-phenyl)-ethyl]-N-phenyl-isobutyramide was used instead of 4-methoxy-N-[-2-(3-methoxy-phenyl)-ethyl]-N-phenyl-benzamide, and the final residue was not subjected to flash chromatography.

$^1$H NMR (400 MHz, CDCl$_3$) $\delta_H$ 0.92 (3H, d, J 6.5 Hz), 1.05 (3H, d, J 7.0 Hz), 2.11 (1H, m), 2.95 (2H, m), 3.42 (1H, m), 3.70 (1H, m), 3.76 (3H, s), 4.32 (1H, d, J 8.0 Hz) and 6.73–7.23 (8H, overlapping m). MS 282 (M+1).

EXAMPLE 52

1-Isopropyl-2-phenyl-1,2,3,4-tetrahydroisoquinolin-6-ol

The title compound was prepared by analogy to Example 48 except that 1-isopropyl-6-methoxy-2-phenyl-1,2,3,4-tetrahydroisoquinoline was used instead of 6-methoxy-1-(4-methoxy-phenyl)-2-phenyl-1,2,3,4-tetrahydroisoquinoline, and hexanes:EtOAc 6:1 was used as eluent for flash chromatography purification.

$^1$H NMR (400 MHz, CDCl$_3$) $\delta_H$ 0.90 (3H, d, J 6.5 Hz), 1.02 (3H, d, J 7.0 Hz), 2.11 (1H, m,), 2.90 (2H, m), 3.42 (1H, m), 3.66 (1H, m), 4.29 (1H, d, J 8.0 Hz), 4.77 (1H, s) and 6.56–7.23 (8H, overlapping m). MS 268 (M+1).

EXAMPLE 53

1,2-Diphenyl-1,2,3,4-tetrahydroisoquinolin-6-ol

The title compound was prepared by analogy to Example 48 except that 6-methoxy-1,2-diphenyl-1,2,3,4-tetrahydroisoquinoline was used instead of 6-methoxy-1-(4-methoxy-phenyl)-2-phenyl-1,2,3,4-tetrahydroisoquinoline, and hexanes:EtOAc 6:1 was used as eluent for flash chromatography purification.

$^1$H NMR (400 MHz, CDCl$_3$) $\delta_H$ 2.84 (2H, m), 3.45 (1H, m), 3.65 (1H, m), 4.98 (1H, broad s), 5.74 (1H, s), 6.56–7.24 (13H, overlapping m). MS 302 (M+1).

EXAMPLE 54

3-[4-(6-Methoxy-2-phenyl-1,2,3,4-tetrahydroisoquinolin-1-yl)-phenyl]-E-acrylic acid methyl/ethyl ester The title compound was prepared by analogy to Preparation 65 except that 3-(4-{[2-(3-methoxy-phenyl)-ethyl]-phenyl-carbamoyl}-phenyl)-E-acrylic acid ethyl ester was used instead of 4-methoxy-N-[2-(3-methoxy-phenyl)-ethyl]-N-phenyl-benzamide. This compound was obtained as an approximately 1:1 mixture of methyl and ethyl esters (as determined by thin layer chromatography and mass spectrometry) due to transesterification.

MS 400 (R=Me, M+1) and 414 (R=Et, M+1).

EXAMPLE 55

-3-[4-(6-Hydroxy-2-phenyl-1,2,3,4-tetrahydro-isoquinolin-1-yl)-phenyl]-E-acrylic acid methyl/ethyl esters The title compound was prepared by analogy to Example 48 except that E-3-[4-(6-methoxy-2-phenyl-1,2,3,4-tetrahydro-isoquinolin-1-yl)-phenyl]-acrylic acid methyl/ethyl esters was used instead of 6-methoxy-1-(4-methoxy-phenyl)-2-phenyl-1,2,3,4-tetrahydroisoquinoline, and hexanes:EtOAc 3:1 was used as the eluent for flash chromatography purification.

EXAMPLE 56

3-[4-(6-Hydroxy-2-phenyl-1,2,3,4-tetrahydroisoquinolin-1-yl)-phenyl]-E-acrylic acid methyl ester To 5 ml of the crude mixture of E-3-[4-(6-hydroxy-2-phenyl-1,2,3,4-tetrahydroisoquinolin-1-yl)-phenyl]-acrylic acid methyl/ethyl esters (0.045 g) in MeOH (see Ex. 55) was added a catalytic amount of NaOMe (prepared by dissolving Na in MeOH) as a solution in MeOH (1 ml). The reaction was stirred at rt for 36 hours. The pH of the solution was adjusted to about 7 to 8 with 1N HCl and the product was extracted with CH$_2$Cl$_2$:EtOAc (4:1, 3×15 ml). The combined organics were dried over MgSO$_4$, filtered, and concentrated in vacuo. The residue was subjected to flash chromatography (SiO$_2$, hexanes:EtOAc 3:1) to give the desired product (0.012 g, 27% yield).

$^1$H NMR (400 MHz, CDCl$_3$) $\delta_H$ 2.84 (2H, m), 3.44 (1H, m), 3.64 (1H, m), 3.76 (3H, s), 5.71 (1H, s), 6.34 (1H, d, J 16.0 Hz), 6.63–6.80 (5H, overlapping m) 7.08–7.35 (5H, overlapping m), 7.36 (2H, d, J 8.5 Hz) and 7.60 (1H, d, J 16.0 Hz). MS 386 (M+1).

EXAMPLE 57

3-[4-(6-Hydroxy-2-phenyl-1,2,3,4-tetrahydroisoquinolin-1-yl)-phenyl]-E-acrylic acid To a solution of 3-[4-(6-hydroxy-2-phenyl-1,2,3,4-tetrahydroisoquinolin-1-yl)-phenyl]-E-acrylic acid methyl/ethyl esters (0.045 g, 0.115 mmol, 1.0 eq.) in THF (2 ml) was added NaOH (0.009 g, 0.230 mmol, 2.0 eq.) as a solution in water (0.2 ml). Water (1.0 ml) was added and the reaction mixture was stirred at rt for 12 hours. The mixture was diluted with water (5 ml) and acidified to a pH of about 5. The aqueous mixture was extracted with CH$_2$Cl$_2$:EtOAc (4:1, 4×25 ml). The combined organics were dried over MgSO$_4$, filtered, and concentrated in vacuo. The residue was subjected to flash chromatography (SiO$_2$, CH$_2$Cl$_2$:MeOH 10:1) to give the desired compound (0.035 g, 0.0945 mmol, 82% yield).

$^1$H NMR (400 MHz, CDCl$_3$) $\delta_H$ 2.87 (2H, m), 3.47 (1H, m), 3.68 (1H, m), 5.75 (1H, s), 6.37 (1H, d, J 16.0 Hz), 6.65–6.83 (5H, overlapping m), 7.13 (1H, d, J 8.0 Hz), 7.21–7.28 (4H, overlapping m), 7.42 (2H, d, J 8.5 Hz) and 7.72 (1H, d, J 16.0 Hz). MS 372 (M+H).

EXAMPLE 58

1-Benzyl-6-methoxy-2-phenyl-1,2,3,4-tetrahydroisoquinoline

The title compound was prepared by analogy to Preparation 65 except that N-[2-(3-methoxy-phenyl)-ethyl]-2,N-diphenyl-acetamide was used instead of 4-methoxy-N-[2-(3-methoxy-phenyl)-ethyl]-N-phenyl-benzamide, and the final residue was not subjected to flash chromatography.

MS 330 (M+1).

EXAMPLE 59

1-Benzyl-2-phenyl-1,2,3,4-tetrahydroisoquinolin-6-ol

The title compound was prepared by analogy to Example 48 except that 1-benzyl-6-methoxy-2-phenyl-1,2,3,4- tetrahydroisoquinoline was used instead of 6-methoxy-1-(4-methoxy-phenyl)-2-phenyl-1,2,3,4-tetrahydroisoquinoline, and hexanes:EtOAc 6:1 was used as eluent for flash chromatography purification.

$^1$H NMR (400 MHz, CDCl$_3$) $\delta_H$ 2.68 (1H, m), 2.67 (1H, m), 2.94 (1H, dd, 13.5 and 7.5 Hz), 3.21 (1H, dd, J 13.5 and 5.5 Hz), 3.49 (1H, m), 3.58 (1H, m), 4.83 (1H, dd, J 7.5 and 5.5 Hz), 5.18 (1H, broad s), 6.47–6.58 (3H, overlapping m), 6.74 (1H, t, J 7.5 Hz), 6.84 (2H, d, J 8.0 Hz), 7.00 (2H, dd, 7.0 and 1.5 Hz) and 7.17–7.26 (5H, overlapping m). MS 314 (M+1).

EXAMPLE 60

6-Methoxy-2-phenyl-1-thiophen-2-yl-1,2,3,4-tetrahydroisoquinoline

The title compound was prepared by analogy to Preparation 65 except that thiophene-2-carboxylic acid [2-(3-methoxy-phenyl)-ethyl]-phenyl-amide was used instead of 4-methoxy-N-[2-(3-methoxy-phenyl)-ethyl]-N-phenyl-benzamide, and the final residue was not subjected to flash chromatography.

$^1$H NMR (400 MHz, CDCl$_3$) $\delta_H$ 2.90 (1H, m), 2.98 (1H, m), 3.54 (1H, m), 3.60 (1H, m), 3.80 (3H, s), 5.99 (1H, s) and 6.67–7.27 (11 H overlapping m). MS 321 (M).

EXAMPLE 61

2-Phenyl-1-thiophen-2-yl-1,2,3,4-tetrahydroisoquinolin-6-ol

The title compound was prepared by analogy to Example 48 except that 6-methoxy-2-phenyl-1-thiophen-2-yl-1,2,3,4-tetrahydroisoquinoline was used instead of 6-methoxy-1-(4-methoxy-phenyl)-2-phenyl-1,2,3,4-tetrahydroisoquinoline, and hexanes:EtOAc from 4:1 to 1:1 was used as eluent for flash chromatography purification.

$^1$H NMR (400 MHz, CDCl$_3$) $\delta_H$ 2.84 (1H, m), 2.91 (1H, m), 3.50 (1H, m), 3.56 (1H, m), 5.96 (1H, s), 6.61–6.67 (3H, overlapping m), 6.76–6.84 (2H overlapping m), 6.91 (2H, d J 7.5 Hz), 7.09 (2H, m) and 7.23 (2H, m). MS 308 (M+H).

EXAMPLE 62

6-Methoxy-1-naphthalen-2-yl-2-phenyl-1,2,3,4-tetrahydroisoquinoline

The title compound was prepared by analogy to Preparation 65 except that naphthalene-2-carboxylic acid [2-(3-methoxy-phenyl)-ethyl]-phenyl-amide was used instead of 4-methoxy-N-[2-(3-methoxy-phenyl)-ethyl]-N-phenyl-benzamide, and the final residue was not subjected to flash chromatography. MS (M) 365.

EXAMPLE 63

1-Naphthalen-2-yl-2-phenyl-1,2,3,4-tetrahydroisoquinolin-6-ol

The title compound was prepared by analogy to Example 48 except that 6-methoxy-1-naphthalen-2-yl-2-phenyl-1,2,3,4-tetrahydroisoquinoline was used instead of 6-methoxy-1-(4-methoxy-phenyl)-2-phenyl-1,2,3,4-tetrahydroisoquinoline, and neat CH$_2$Cl$_2$ to 10% MeOH/CH$_2$Cl$_2$ was used as eluent for flash chromatography purification.

$^1$H NMR (400 MHz, CD$_3$OD) $\delta_H$ 2.86 (2H, m), 3.44 (1H, m), 3.65 (1H, m), 5.87 (1H, s), 6.60–6.68(3H, overlapping m), 6.87 (2H, d J 8.0 Hz), 7.12 (3H, m), 7.37 (3H, m), 7.51 (1H, s) and 3H, m). MS 352 (M+1).

EXAMPLE 64

6-Methoxy-2-phenyl-1-(3,4,5-trifluoro-phenyl)-1,2,3,4-tetrahydroisoquinoline

The title compound was prepared by analogy to Preparation 65 except that 3,4,5-trifluoro-N-[2-(3-methoxy-phenyl)-ethyl]-N-phenyl-benzamide was used instead of 4-methoxy-N-[2-(3-methoxy-phenyl)-ethyl]-N-phenyl-benzamide, and the final residue was not subjected to flash chromatography.

MS 369 (M+1).

EXAMPLE 65

2-Phenyl-1-(3,4,5-trifluoro-phenyl)-1,2,3,4-tetrahydroisoquinolin-6-ol

The title compound was prepared by analogy to Example 48 except that 6-methoxy-2-phenyl-1-(3,4,5-trifluoro-phenyl)-1,2,3,4-tetrahydroisoquinoline was used instead of 6-methoxy-1-(4-methoxy-phenyl)-2-phenyl-1,2,3,4-tetrahydroisoquinoline, and neat CH$_2$Cl$_2$ to 10% MeOH/CH$_2$Cl$_2$ was used as eluent for flash chromatography purification.

$^1$H NMR (400 MHz, CD$_3$OD) $\delta_H$ 2.83 (2H, m), 3.38 (1H, m), 3.59 (1H, m), 5.70 (1H, s) and 6.61–7.18 (10H, overlapping m). MS 356 (M+1).

EXAMPLE 66

1-(4-Chloro-phenyl)-2-phenyl-1,2,3,4-tetrahydroisoquinolin-6-ol

The title compound was prepared by analogy to Example 48 except that 1-(4-chloro-phenyl)-6-methoxy-2-phenyl-1,2,3,4-tetrahydroisoquinoline was used instead of 6-methoxy-1-(4-methoxy-phenyl)-2-phenyl-1,2,3,4-tetrahydroisoquinoline, and neat CH$_2$Cl$_2$ to 10% MeOH/CH$_2$Cl$_2$ was used as eluent for flash chromatography purification.

$^1$H NMR (400 MHz, CD$_3$OD) $\delta_H$ 2.83 (2H, m), 3.37 (1H, m), 3.58 (1H, m), 5.71 (1H, s) and 6.62–7.18 (12H, overlapping m). MS 336/338 (M+1).

EXAMPLE 67

6-Methoxy-2-phenyl-1-thiazol-2-yl-1,2,3,4-tetrahydroisoquinoline

The title compound was prepared by analogy to Preparation 65 except that thiazole-2-carboxylic acid [2-(3-methoxy-phenyl)-ethyl]-phenyl-amide was used instead of 4-methoxy-N-[2-(3-methoxy-phenyl)-ethyl]-N-phenyl-benzamide, and the final residue was not subjected to flash chromatography.

MS 322 (M+1).

EXAMPLE 68

2-Phenyl-1-thiazol-2-yl-1,2,3,4-tetrahydroisoquinolin-6-ol

The title compound was prepared by analogy to Example 48 except that 6-methoxy-2-phenyl-1-thiazol-2-yl-1,2,3,4-tetrahydroisoquinoline was used instead of 6-methoxy-1-(4-methoxy-phenyl)-2-phenyl-1,2,3,4-tetrahydroisoquinoline, and neat $CH_2Cl_2$ to 10% $MeOH/CH_2Cl_2$ was used as eluent for flash chromatography purification.

$^1$H NMR (400 MHz, $CDCl_3$) $\delta_H$ 2.93 (1H, m), 3.01 (1H, m), 3.40 (1H, m), 3.77 (1H, m), 5.94 (1H, s), 6.59–6.86 (5H, overlapping m), 7.12 (1H, d J 3.0 Hz), 7.16–7.27 (3H, overlapping m) and 7.64 (1H, d J 3.0 Hz). MS 309 (M+1).

EXAMPLE 69

1-Adamantan-1-yl-6-methoxy-2-phenyl-1,2,3,4-tetrahydroisoquinoline

The title compound was prepared by analogy to Preparation 65 except that adamantane-1-carboxylic acid [2-(3-methoxy-phenyl)-ethyl]-phenyl-amide was used instead of 4-methoxy-N-[2-(3-methoxy-phenyl)-ethyl]-N-phenyl-benzamide, and the final residue was subjected to flash chromatography using hexanes:EtOAc from 20:1 to 10:1. MS (M) 373.

EXAMPLE 70

1-Adamantan-1-yl-2-phenyl-1,2,3,4-tetrahydroisoquinolin-6-ol

The title compound was prepared by analogy to Example 48 except that 1-adamantan-1-yl-6-methoxy-2-phenyl-1,2,3,4-tetrahydroisoquinoline was used instead of 6-methoxy-1-(4-methoxy-phenyl)-2-phenyl-1,2,3,4-tetrahydroisoquinoline, and neat $CH_2Cl_2$ to 10% $MeOH/CH_2Cl_2$ was used as eluent for flash chromatography purification.

$^1$H NMR (400 MHz, $CDCl_3$) $\delta_H$ 1.54–2.10 (15H, overlapping m), 2.86(1H, m), 3.06 (1H, m), 33.38 (1H, m), 3.84 (1H, m), 4.45(1H, s) and 6.50–7.19 (8H, overlapping m). MS 360 (M+1).

EXAMPLE 71

6-Methoxy-2-phenyl-1-pyridin-4-yl-1,2,3,4-tetrahydroisoquinoline

The title compound was prepared by analogy to Preparation 65 except that N-[2-(3-methoxy-phenyl)-ethyl]-N-phenyl-isonicotinamide was used instead of 4-methoxy-N-[2-(3-methoxy-phenyl)-ethyl]-N-phenyl-benzamide, and the final residue was subjected to flash chromatography using hexanes:EtOAc from 4:1 to 2:1.

$^1$H NMR (400 MHz, $CDCl_3$) $\delta_H$ 2.82(1H, m), 2.90 (1H, m), 3.47 (1H, m), 3.66 (1H, m), 3.79 (3H, s), 5.70 (1H, s), 5.70 (1H, s), 6.71–6.80(5H, overlapping m), 7.18–7.25 (5H, overlapping m) and 8.46 (2H, m). MS 317 (M+1).

EXAMPLE 72

2-Phenyl-1-pyridin-4-yl-1,2,3,4-tetrahydroisoquinolin-6-ol

The title compound was prepared by analogy to Example 48 except that 6-methoxy-2-phenyl-1-pyridin-4-yl-1,2,3,4-tetrahydroisoquinoline was used instead of 6-methoxy-1-(4-methoxy-phenyl)-2-phenyl-1,2,3,4-tetrahydroisoquinoline, and hexanes:EtOAc from 4:1 to 1:1 was used as eluent for flash chromatography purification.

$^1$H NMR (400 MHz, $CD_3OD$) $\delta_H$ 2.84 (2H, overlapping m), 3.38 (1H, m), 3.65 (1H, m), 5.77 (1H, s), 6.60–6.71 (4H, overlapping m), 6.79 (2H, d, J 8.0 Hz), 7.15 (4H, ,m), 7.28 (2H, m) and 8.34 (1H, broad s). MS 303 (M+1).

EXAMPLE 73

1-(4-Iodo-phenyl)-6-methoxy-2-phenyl-1,2,3,4-tetrahydroisoquinoline

The title compound was prepared by analogy to Preparation 65 except that 4-iodo-N-[2-(3-methoxy-phenyl)-ethyl]-N-phenyl-benzamide was used instead of 4-methoxy-N-[2-(3-methoxy-phenyl)-ethyl]-N-phenyl-benzamide, and the final residue was subjected to flash chromatography using a gradient from neat $CH_2Cl_2$ to $CH_2Cl_2$:MeOH 60:1.

$^1$H NMR (400 MHz, $CDCl_3$) $\delta_H$ 2.83 (2H, m,) 3.42 (1H, m), 3.62 (1H, m), 3.75 (3H, s), 5.65 (1H, s) 6.67–6.80 (5H, overlapping m), 6.94 (2H, d, J 8.5 Hz), 7.08–7.11 (3H, overlapping m) and 7.50 (2H, d, J 8.5 Hz). MS 442 (M+1).

EXAMPLE 74

1-(4-Iodo-phenyl)-2-phenyl-1,2,3,4-tetrahydroisoquinolin-6-ol

The title compound was prepared by analogy to Example 48 except that 1-(4-iodo-phenyl)-6-methoxy-2-phenyl-1,2,3,4-tetrahydroisoquinoline was used instead of 6-methoxy-1-(4-methoxy-phenyl)-2-phenyl-1,2,3,4-tetrahydroisoquinoline, and $CH_2Cl_2$:MeOH in a gradient from 20:1 to 9:1 was used as eluent for flash chromatography purification.

$^1$H NMR (400 MHz, $CDCl_3$) $\delta_H$ 2.80 (2H, m,) 3.43 (1H, m), 3.61 (1H, m), 5.65 (1H, s) 6.62–6.65 (2H, overlapping m), 6.74–6.81 (3H, overlapping m), 6.94 (2H, d, J 8.5 Hz), 7.05 (1H, m), 7.18–7.22 (2H, overlapping m) and 7.51 (2H, d, J 8.5 Hz). MS 428 (M+1).

EXAMPLE 75

E-3-[4-(6-Hydroxy-2-phenyl-1,2,3,4-tetrahydroisoquinolin-1-yl)-phenyl]-1-piperidin-1-yl-propenone To a stirred solution of piperidine (0.61 ml, 6.19 mmol, 1.0 eq.) and $Et_3N$ (2.58 ml, 18.6 mmol, 3.0 eq.) in toluene (10 ml) was added acryloyl chloride (1.14 g, 12.4 mmol, 2.0 eq.) in a dropwise manner. The reaction was stirred overnight at RT. The reaction mixture was diluted with $CH_2Cl_2$ (20 ml) and washed sequentially with 1N HCl (1×20 ml) and sat. $NaHCO_3$ (1×20 ml). The organic layer was dried over $MgSO_4$, filtered, and concentrated in vacuo. The resulting material (1-piperidin-1-yl-propenone) was used without purification.

To a stirred solution of 1-(4-iodo-phenyl)-2-phenyl-1,2,3,4-tetrahydroisoquinolin-6-ol (0.100 g, 0.234 mmol, 1.0 eq.), 1-piperidin-1-yl-propenone (0.043 g, 0.351 mmol, 1.5 eq.), and $Et_3N$ (0.163 ml, 1.17 mmol, 5.0 eq.) in dry DMF (2 ml) under an atmosphere of $N_2$ was added $Pd(PPh_3)_4$ (0.013 g, 11.3 μmol, 0.05 eq.). The reaction mixture was heated to 100° C. overnight. The reaction mixture was allowed to cool to RT, diluted with water (10 ml), and extracted with EtOAc (2×10 ml). The combined organics were dried over $Na_2SO_4$, filtered, and concentrated in vacuo. The residue was subjected to flash chromatography ($SiO_2$, $CH_2Cl_2$ to $CH_2Cl_2$:MeOH 19:1) to give the desired compound.

$^1$H NMR (400 MHz, $CDCl_3$) $\delta_H$ 1.53–1.64 (6H, overlapping m), 2.77 (2H, m), 3.44–3.62 (6H, overlapping m), 5.68 (1H, s), 6.19–7.64 (14H, overlapping m). MS 439 (M+1).

EXAMPLE 76

E-3-[4-(6-Hydroxy-2-phenyl-1,2,3,4-tetrahydroisoquinolin-1-yl)-phenyl]-acrylamide To a stirred solution of 1-(4-iodo-phenyl)-2-phenyl-1,2,3,4-tetrahydroisoquinolin-6-ol (0.100 g, 0.234 mmol), triethylamine (0.163 ml, 1.17 mmol), and acrylamide (0.082 g, 0.351 mmol) in DMF (2 ml), under an atmosphere of $N_2$, was added $Pd(PPh_3)_4$ (0.014 g, 0.012 mmol). The solution was heated to 100° C. overnight, then cooled to RT and diluted with water (20 ml). The aqueous mixture was extracted with EtOAc (3×10 ml). The combined organics were dried over $MgSO_4$, filtered, and concentrated in vacuo. The residue was subjected to flash chromatography ($SiO_2$, 5% $MeOH/CH_2Cl_2$) to give the desired product (0.030 g, 0.089 mmol, 35% yield).

$^1H$ NMR (400 MHz, $CDCl_3$) $\delta_H$ 2.80 (2H, m,), 3.19 (1H, m), 3.42 (1H, m) 5.67(1H, s), 5.88 (1H, br s), 6.17 (1H, br s), 6.38 (1H, d, J 15.5 Hz), 6.67–6.78 (5H, overlapping m), 7.04–7.32 (7H, overlapping m) and 7.52 (1H, d, 15.5 Hz). MS 371 (M+1).

EXAMPLE 77

E-3-[4-(6-Hydroxy-2-phenyl-1,2,3,4-tetrahydroisoquinolin-1-yl)-phenyl]-1-morpholin-4-yl-propenone The title compound was prepared by analogy to Example 75 except that morpholine was used instead piperidine.

$^1H$ NMR (400 MHz, $CDCl_3$) $\delta_H$ 3.10 (2H, m), 3.56–3.74 (10H, overlapping m), 5.71 (1H, s), 6.49–7.67 (14H, overlapping m). MS 441 (M+1).

EXAMPLE 78

E-3-[4-(6-Hydroxy-2-phenyl-1,2,3,4-tetrahydroisoquinolin-1-yl)-phenyl]-N,N-dimethyl-acrylamide The title compound was prepared by analogy to Example 75 except that dimethylamine was used instead piperidine. MS 399 (M+1).

EXAMPLE 79

2,2,2-Trifluoro-1-{6-methoxy-1-[1-(1-methyl-1H-imidazole4-sulfonyl)-piperidin4-yl]-3,4-dihydro-1H-isoquinolin-2-yl}-ethanone To a stirred solution of 6-methoxy-1-[1-(1-methyl-1H-imidazole-4-sulfonyl)-piperidin-4-yl]-1,2,3,4tetrahydroisoquinoline (0.049 g, 0.126 mmol) and triethylamine (0.135 g, 0.132 mmol) in $CH_2Cl_2$ (5 ml) cooled to 0° C. under an atmosphere of $N_2$ was added trifluoroacetic acid anhydride (0.028 g, 0.132 mmol). The reaction mixture was stirred overnight, slowly warming to RT. The reaction was quenched by the addition of water (1 ml) and diluted with $CH_2Cl_2$ (5 ml). The layers were separated and the organic layer was further diluted with $CH_2Cl_2$ (15 ml), washed with sat. $NaHCO_3$ (2×3 ml) and brine (1×3 ml), dried over $MgSO_4$, filtered, and concentrated in vacuo. The residue was purified by radial chromatography ($SiO_2$, 1 mm $CH_2Cl_2$ to 2% $MeOH/CH_2Cl_2$) to give the desired product as an oil (0.043 g, 0.088 mmol, 71% yield).

$^1H$ NMR (400 MHz, $CDCl_3$) $\delta_H$ 1.41–1.80 (5H, overlapping m), 2.53 (2H, m), 2.92 (2H, m), 3.68 (1H, m), 3.73 (3H, s), 3.77 (3H, s), 3.90 (3H, m), 5.23 (1H, d, J 8.0 Hz), 6.65–7.00 (3H, m), 7.39 (1H, d, J 1.5 Hz), and 7.45 (1H, d, J 1.5 Hz).

EXAMPLE 80

2,2,2-Trifluoro-1-{6-hydroxy-1-[1-(1-methyl-1H-imidazole-4-sulfonyl)-piperidin-4-yl]-3,4-dihydro-1H-isoquinolin-2-yl}-ethanone To a stirred solution of 2,2,2-trifluoro-1-{6-methoxy-1-[1-(1-methyl-1H-imidazole-4-sulfonyl)-piperidin-4-yl]-3,4-dihydro-1H-isoquinolin-2-yl}-ethanone (0.036 g, 0.074 mmol) in $CH_2Cl_2$ (3 ml) under an atmosphere of $N_2$ cooled to −78° C. was added boron tribromide as a 1.0 M solution in $CH_2Cl_2$ (0.3 ml, 0.3 mmol). The reaction mixture was stirred overnight slowly, while allowing it to warm to RT. MeOH (1 ml) was added to the reaction mixture and stirring was continued at RT for 10 minutes. Sat. $NaHCO_3$ was added to the reaction mixture until the pH of the aqueous layer was 7. The mixture was then extracted with EtOAc (3×20 ml), the combined organics were washed with brine (1×20 ml), dried over $MgSO_4$, filtered, and concentrated in vacuo to give the desired product as an off white solid (0.028 g, 0.059 mmol, 80% yield).

MS 473 (M+1).

EXAMPLE 81

2-Benzyl-7-methoxy-4-(4-methoxy-phenyl)-1,2,3,4-tetrahydroisoquinoline

To a solution of 2-[benzyl-(3-methoxy-benzyl)-amino]-1-(4-methoxy-phenyl)-ethanol (16.23 g, 43.0 mmol, see Preparation 63) in $CH_2Cl_2$ (280 ml) was added TFA (40.0 g, 27.0 ml, 350 mmol). The mixture was refluxed overnight. The reaction mixture was allowed to cool to RT and poured onto ice-water containing sat. $NaHCO_3$ (250 ml). The mixture was extracted with $CH_2Cl_2$ (3×150 ml) and the combined organics were dried over $MgSO_4$, filtered, and concentrated in vacuo. Flash chromatography ($SiO_2$, gradient elution 10–40% EtOAc/Hexanes) of the residue afforded the title product (7.67 g, 21.3 mmol, 50% yield).

$^1H$ NMR (400 MHz, $CDCl_3$) $\delta_H$ 2.60 (1H, m), 3.03 (1H, m), 3.67 (2H, m), 3.77 (3H,s), 4.13 (1H, m), 6.54 (1H, d J 2.5 Hz), 6.62 (1H, dd, J 8.5 and 2.5 Hz), 6.78 (3H, m), 7.08 (2H, d, J 8.5 Hz) and 7.73–7.28 (5H, m). MS 360 (M+1).

EXAMPLE 82

2,2,2-Trifluoro-1-[7-methoxy-4-(4-methoxy-phenyl)-3,4-dihydro-1H-isoquinolin-2-yl]-ethanone To a solution of 7-methoxy-4-(4-methoxy-phenyl)-1,2,3,4-tetrahydroisoquinoline (1.43 g, 5.31 mmol, see Preparation 64) and $Et_3N$ (1.08 g, 10.6 mmol) in $CH_2Cl_2$ (50 ml) cooled to 0° C. was added trifluoroacetic anhydride (1.89 g, 1.27 ml, 9.03 mmol). The reaction was stirred at 0° C. for 4 hours, then the reaction mixture was poured into sat. $NaHCO_3$ (50 ml). The mixture was extracted with $CH_2Cl_2$ (3×50 ml). The organics were combined, dried over $MgSO_4$, filtered, and concentrated in vacuo. Flash chromatography (Biotage, $SiO_2$, 10% EtOAc/hexanes) gave the title product (1.74 g, 4.76 mmol, 90% yield).

$^1H$ NMR (400 MHz, $CDCl_3$) $\delta_H$ 3.69–3.75 (1H, m), 3.78 (3H, s), 3.79 (3H, s (2H, m), 4.72–4.99 (2H, m), 6.65–6.75 (2H, m), 6.81–6.87 (3H, m) and 6.98–7.02 (2H, m). MS 366 (M+1).

EXAMPLE 83

2,2,2-Trifluoro-1-[7-hydroxy-4-(4-hydroxy-phenyl)-3,4-dihydro-1H-isoquinolin-2-yl]-ethanone To a solution of 2,2,2-trifluoro-1-[7-methoxy-4-(4-methoxy-phenyl)-3,4-dihydro-1H-isoquinolin-2-yl]-ethanone (1.74 g, 4.76 mmol, see Example 82) in $CH_2Cl_2$ (100 ml) cooled to 0° C. was added $BBr_3$ as a 1.0 M solution in $CH_2Cl_2$ (14.28 ml, 14.28 mmol) in a dropwise manner. The reaction mixture was stirred at 0° C. for 60 minutes, the ice bath removed, and stirring continued at RT for 90 minutes. MeOH (10 ml) was added to the reaction and stirring was continued at RT for 10 minutes. The reaction mixture was concentrated in vacuo and purified by flash chromatography (Biotage, $SiO_2$, 25–40% EtOAc/hexanes) to give the title product (1.36 g, 4.03 mmol, 85% yield).

$^1$H NMR (400 MHz, $CD_3OD$) $\delta_H$ 3.77–4.13 (3H, m), 4.72–4.86 (2H, m), 6.59–6.76 (5H, m) and 6.86–6.90 (2H, m). MS 338 (M+1).

EXAMPLE 84

Cyclohexyl-[7-hydroxy-4-(4-hydroxy-phenyl)-3,4-dihydro-1H-isoquinolin-2-yl]-methanone A solution of 7-methoxy-4-(4-methoxy-phenyl)-1,2,3,4-tetrahydroisoquinoline (0.103 g, 0.382 mmol, 1.0 eq., see Preparation 64) and triethylamine (0.107 ml, 0.764 mmol, 2.0 eq.) in $CH_2Cl_2$ (2 ml) was added to a vial containing cyclohexanecarbonyl chloride (0.084 g, 0.573 mmol, 1.5 eq.). The reaction mixture was stirred overnight at RT. To this mixture was added $BBr_3$ as a 1.0M solution in $CH_2Cl_2$ (1.15 ml, 1.15 mmol, 3.0 eq.). The reaction mixture was stirred overnight at rt, then cooled to −78° C. and quenched with MeOH (1.5 ml). The reaction mixture was evaporated under a stream of nitrogen and purified by reverse phase HPLC (gradient elution 98:2 $H_2O$:0.1% TFA, then 2:98 $MeCN$:$H_2O$). The exact yield was not determined.

$^1$H NMR (400 MHz, $CD_3OD$) $^6$H 1.12–1.94 (10H, overlapping m), 2.67 (1H, m), 3.77 (1H, m), 3.94 (1H, m), 4.09 (1H, m), 4.35 (1H, d, J 17.5 Hz), 5.06 (1H, d, J 17.5 Hz) and 6.58–6.88 (7H, overlapping m). MS 352 (M+1).

EXAMPLE 85

[7-Hydroxy-4-(4-hydroxy-phenyl)-3,4-dihydro-1H-isoquinolin-2-yl]-phenyl-methanone The title compound was prepared by analogy to Example 84 except benzoyl chloride was used in place of cyclohexanecarbonyl chloride.

$^1$H NMR (400 MHz, $CD_3OD$) $\delta_H$ 3.68 (2H, m), 3.84–4.18 (3H, overlapping m), 4.52 (1H, d, J 17.5 Hz), 5.22 (1H, d J 17.5 Hz), 6.57–6.96 (8H, overlapping m) and 7.19–7.46 (4H, m). MS 346 (M+1).

EXAMPLE 86

2-Benzenesulfonyl-4-(4-hydroxy-phenyl)-1,2,3,4-tetrahydroisoquinolin-7-ol

A solution of 7-methoxy-4-(4-methoxy-phenyl)-1,2,3,4-tetrahydroisoquinoline (0.103 g, 0.382 mmol, 1.0 eq., see Preparation 64) and triethylamine (0.107 ml, 0.764 mmol, 2.0 eq.) in $CH_2Cl_2$ (2 ml) was added to a vial containing benzenesulfonyl chloride (0.101 g, 0.573 mmol, 1.5 eq.). The reaction mixture was stirred overnight at RT. To this mixture was added $BBr_3$ as a 1.0M solution in $CH_2Cl_2$ (1.15 ml, 1.15 mmol, 3.0 eq.). The reaction mixture was again stirred overnight at RT, then cooled to −78° C. and quenched with MeOH (1.5 ml). The reaction mixture was evaporated under a stream of nitrogen and purified by reverse phase HPLC (gradient elution 98:2 $H_2O$:0.1% TFA, then 2:98 $MeCN$:$H_2O$). The exact yield was not determined.

$^1$H NMR (400 MHz, $CD_3OD$) $\delta_H$ 3.04 (1H, dd, J 12.0 and 7.5 Hz), 3.55 (1H, dd, J 12.0 and 5.0 Hz), 4.02 (1H, dd J 6.5 and 6.0 Hz), 4.12 (1H, d, J 15.0 Hz), 4.27 (1H, d, J 15.0 Hz), 6.52 (2H, m), 6.65 (3H, m), 6.87 (1H, d, J 8.5 Hz), 7.55 (2H, m), 7.56 (1H, m) and 7.75 (1H, d, J 8.0 Hz). MS 382 (M+1).

EXAMPLE 87

4-(4-Hydroxy-phenyl)-2-(naphthalene-1-sulfonyl)-1,2,3,4-tetrahydroisoquinolin-7-ol The title compound was prepared by analogy to Example 86 except naphthalene-1-sulfonyl chloride was used in place of benzenesulfonyl chloride.

$^1$H NMR (400 MHz, $CD_3OD$) $\delta_H$ 3.34 (1H, dd, J 12.0 and 7.0 Hz), 3.64 (1H, dd, J 12.0 and 4.5 Hz), 3.93 (1H, t, J 6.0 Hz), 4.36 (1H, d, 15.5 Hz), 4.42 (1H, d, J 15.5 Hz), 6.45–6.68 (7H, overlapping m), 7.93 (1H, m), 8.10–8.18 (2H, overlapping m) and 8.54 (1H, m). MS 432 (M+1).

EXAMPLE 88

2-(Biphenyl-4-sulfonyl)-4-(4-hydroxy-phenyl)-1,2,3,4-tetrahydroisoquinolin-7-ol

The title compound was prepared by analogy to Example 86 except biphenyl-4-sulfonyl chloride was used in place of benzenesulfonyl chloride.

$^1$H NMR (400 MHz, $CD_3OD$) $\delta_H$ 3.09 (1H, dd, J 12.0 and 7.5 Hz), 3.59 (1H, dd, J 12.0 and 5.0 Hz), 4.05 (1H, dd, J 7.5 and 5.0 Hz), 4.17 (1H, d, J 15.0 Hz), 4.32 (1H, J 15.0 Hz), 6.54 (3H, m), 6.64 (3H, m), 6.88 (2H, m), 7.36–7.47 (3H, overlapping m), 7.66 (2H, m) and 7.80 (2H, m). MS 458 (M+1).

EXAMPLE 89

4-(4-Hydroxy-phenyl)-2-phenylmethanesulfonyl-1,2,3,4-tetrahydroisoquinolin-7-ol

The title compound was prepared by analogy to Example 86 except phenyl-methanesulfonyl chloride was used in place of benzenesulfonyl chloride.

$^1$H NMR (400 MHz, $CD_3OD$) $\delta_H$ 3.19 (1H, m), 3.56 (1H, dd, 12.5 and 5.0 Hz), 3.88 (1H, J 7.5 and 6.0 Hz), 4.20–4.39 (4H, overlapping m), 6.48–6.58 (2H, overlapping m), 6.52–6.71 (3H, overlapping m), 6.85 (2H, m) and 7.22–7.38 (5H, overlapping m). MS 396 (M+1).

What is claimed is:
1. A compound of the formula:

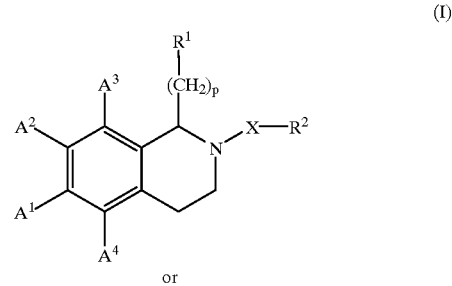

or

-continued

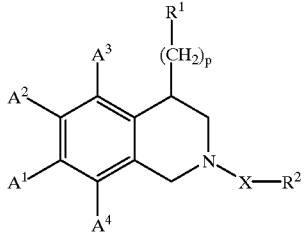

(II)

wherein:
A$^1$ is hydrogen, hydroxy, (C$_1$–C$_4$)alkoxy, or (C$_1$–C$_4$) alkanoyloxy, said (C$_1$–C$_4$)alkoxy or said (C$_1$–C$_4$) alkanoyloxy optionally substituted by hydroxy, halo, di(C$_1$–C$_4$alkyl)amino or a partially saturated, fully saturated, or fully unsaturated five to twelve membered ring optionally comprising one to four heteroatoms independently selected from oxygen, sulfur, and nitrogen;

A$^2$, A$^3$, and A$^4$ are independently selected from hydrogen, hydroxy, (C$_1$–C$_4$)alkoxy, and halo;

R$^1$ is (C$_1$–C$_7$)alkyl; adamantyl; a partially saturated, fully saturated, or fully unsaturated three to twelve membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, said bicyclic ring system optionally comprising one to four heteroatoms independently selected from oxygen, sulfur, and nitrogen; wherein each of the above R$^1$ groups is optionally substituted with one to seven fluoro, or optionally substituted with one to three substituents independently selected from Group A, wherein Group A consists of hydroxy, chloro, bromo, iodo, (C$_1$–C$_4$)alkyl, (C$_1$–C$_4$) alkoxy, (C$_3$–C$_8$)cycloalkyl, R$^3$—(C$_1$–C$_4$)alkoxy, (C$_2$–C$_4$)alkenyl-COOR$^7$, (C$_0$–C$_4$)alkyl-COOR$^7$, (C$_1$–C$_4$)alkanoyloxy-(C$_2$–C$_4$)alkenyl, (C$_2$–C$_4$)alkenyl-CONR$^4$R$^5$, (C$_0$–C$_4$)alkyl-CONR$^4$R$^5$, (C$_0$–C$_4$)alkyl-NR$^4$R$^5$, OCH$_2$CH$_2$NR$^8$R$^9$, propyl-R$^8$R$^9$, and SO$_2$—R$^6$;

X is (CH$_2$)$_n$ wherein n is 1, 2, or 3, (C$_0$–C$_1$)alkylene-phenylene-(C$_0$–C$_1$)alkylene, CO$_2$, (C$_0$–C$_3$)alkylene-CO—(C$_0$–C$_3$)alkylene, or (C$_0$–C$_4$)alkylene-SO$_2$—(C$_0$–C$_4$)alkylene;

R$^2$ is (C$_1$–C$_9$)alkyl; (C$_2$–C$_4$)alkenyl; benzhydryl; a partially saturated, fully saturated, or fully unsaturated three to eight membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, and said bicyclic ring system optionally comprising one to four heteroatoms independently selected from oxygen, sulfur, and nitrogen; wherein said (C$_1$–C$_9$)alkyl is optionally substituted with one to seven fluoro, or optionally substituted with one to three substituents independently selected from Group B, wherein Group B consists of chloro, (C$_1$–C$_4$)alkoxy, amino, and (C$_1$–C$_4$)alkylcarbonyl; wherein said (C$_2$–C$_4$)alkenyl is optionally substituted with one to three substituents independently selected from Group C, wherein Group C consists of halo, (C$_1$–C$_4$)alkoxy, amino, and (C$_1$–C$_4$) alkylcarbonyl; and wherein said benzhydryl, said three to eight membered ring, said bicyclic ring, and said bicyclic ring system are each optionally substituted with one to three substituents independently selected from Group D, wherein Group D consists of halo, hydroxy, (C$_1$–C$_4$)alkyl, (C$_1$–C$_4$)alkoxy, imidazolyl, amino, (C$_1$–C$_4$)alkylcarbonylamino, and (C$_1$–C$_4$) alkylcarbonyl;

R$^3$ at each occurrence is independently pyrrolidino, piperidino, morpholino, or dimethylamino;

R$^4$ and R$^5$ at each occurrence are independently hydrogen, (C$_1$–C$_4$)alkyl, hydroxy(C$_1$–C$_4$)alkyl, (C$_1$–C$_4$)alkoxy-(C$_1$–C$_4$)alkylene, or (C$_3$–C$_8$) cycloalkyl, or R$^4$ and R$^5$ taken together with the nitrogen atom to which they are attached are pyrrolidino, piperidino, morpholino, or hexamethyleneimino;

R$^6$ at each occurrence is independently imidazolyl, thienyl, benzathienyl, or isoxazyl, said imidazolyl, thienyl, benzathienyl, or isoxazyl each optionally substituted with one to three substituents independently selected from (C$_1$–C$_4$)alkyl;

R$^7$ at each occurrence is independently hydrogen or (C$_1$–C$_4$)alkyl;

R$^8$ and R$^9$ are independently methyl or ethyl, or R$^8$ and R$^9$ taken together with the nitrogen atom to which they are attached are pyrrolidino, piperidino, morpholino, or hexamethyleneimino; and p is 0, 1, or 2;

with the proviso that
when X is (CH$_2$)$_2$ or (CH$_2$)$_3$, p is 0, and R$^1$ is phenyl or phenyl substituted with one chloro, fluoro, bromo, hydroxy, methoxy, pyrrolidinoethoxy, piperidinoethoxy, or morpholinoethoxy substituent, then R$^2$ is not phenyl, methoxyphenyl, tert-butyl, or cyclopentyl; and when X is CH$_2$, (CH$_2$)$_2$, COCH$_2$, or CH$_2$CO, A$^1$ is hydrogen, and R$^1$ is phenyl, then R$^2$ is not phenyl.

2. A compound of claim 1 wherein:
A$^1$ is hydroxy;
A$^2$, A$^3$, and A$^4$ are hydrogen; and
p is 0.

3. A compound of claim 1 wherein R$^1$ is (C$_1$–C$_4$)alkyl, adamantyl, naphthyl, or a partially saturated, fully saturated, or fully unsaturated five to six membered ring optionally comprising one to two heteroatoms selected independently from oxygen, sulfur, and nitrogen; wherein each of said R$^1$ groups is optionally substituted with one to seven fluoro, or optionally substituted with one to three substituents independently selected from Group A.

4. A compound of claim 3 wherein R$^1$ is phenyl, cyclohexyl, pyridyl, thienyl, isopropyl, or adamantyl; wherein each of said R$^1$ groups is optionally substituted with one to seven fluoro, or optionally substituted with one to three substituents independently selected from Group A.

5. A compound of claim 4 wherein $R^1$ is phenyl or cyclohexyl;
wherein each of said $R^1$ groups is optionally substituted with one to seven fluoro, or optionally substituted with one to three substituents independently selected from Group A.

6. A compound of claim 3 wherein each of said $R^1$ groups is optionally substituted with one to three bromo, chloro, fluoro or iodo, or optionally substituted with one substituent selected from hydroxy, $(C_1–C_2)$alkoxy, pyrrolidino-$(C_1–C_4)$ alkoxy, dimethylamino, $(C_2–C_4)$alkenyl-COOR$^7$, COOR$^7$, $(C_2–C_4)$alkenyl-CONR$^4$R$^5$ or SO$_2$—R$^6$;
$R^4$ and $R^5$ are independently hydrogen, $(C_1–C_4)$alkyl, hydroxy$(C_1–C_4)$alkyl, —(CH$_2$CH$_2$—O—CH$_3$), or $(C_5–C_6)$cycloalkyl, or $R^4$ and $R^5$ taken together with the nitrogen atom to which they are attached are piperidino or morpholino; and
$R^6$ is imidazolyl optionally substituted with one to three substituents independently selected from $(C_1–C_4)$alkyl.

7. A compound of claim 6 wherein each of said $R^1$ groups is optionally substituted with one to three fluoro, or optionally substituted with one substituent selected from iodo, chloro, bromo, hydroxy, methoxy, pyrrolidino-ethoxy, dimethylamino, COOR$^7$ or ethenyl-CONR$^4$R$^5$;
$R^4$ and $R^5$ are each methyl, or $R^4$ and $R^5$ taken together with the nitrogen atom to which they are attached are piperidino or morpholino; and
$R^7$ is hydrogen or methyl.

8. A compound of claim 7 wherein each of said $R^1$ groups is optionally substituted with one hydroxy or pyrrolidino-ethoxy.

9. A compound of claim 1 wherein X is CH$_2$, CH$_2$-phenylene, CO$_2$, CO—(C$_0$–C$_2$)alkylene, or SO$_2$—(C$_0$–C$_2$) alkylene.

10. A compound of claim 1 wherein X is CO or SO$_2$.

11. A compound of claim 1 wherein $R^2$ is $(C_1–C_7)$alkyl; propenyl; a partially saturated, fully saturated, or fully unsaturated five to seven membered ring optionally comprising one to two heteroatoms selected independently from oxygen, sulfur, and nitrogen; a bicyclic ring consisting of two fused independently partially saturated, fully saturated, or fully unsaturated five to six membered rings, said bicyclic ring optionally comprising one to two oxygen atoms; or biphenyl; wherein said $(C_1–C_7)$alkyl is optionally substituted with one to seven fluoro, or optionally substituted with one to three substituents independently selected from Group B; wherein said propenyl is optionally substituted with one to three substituents independently selected from Group C; and wherein each of said five to seven membered ring, said bicyclic ring, and said biphenyl is optionally substituted with one to three substituents independently selected from Group D.

12. A compound of claim 11 wherein $R^2$ is methyl, t-butyl, phenyl, cyclohexyl, isoxazolyl, tetrahydropyranyl, naphthyl, or benzodioxolyl; wherein each of said methyl or t-butyl is optionally substituted with one to seven fluoro, or optionally substituted with one to three substituents independently selected from Group B; and wherein each of said phenyl, cyclohexyl, isoxazolyl, tetrahydropyranyl, naphthyl, or benzodioxolyl is optionally substituted with one to three substituents independently selected from Group D.

13. A compound of claim 12 wherein $R^2$ is trifluoromethyl or phenyl; wherein said phenyl is optionally substituted with one to three substituents independently selected from Group D.

14. A compound of claim 11 wherein each of said $(C_1–C_7)$ alkyl and said propenyl in the definition of $R^2$ is optionally substituted with one to three fluoro, or optionally substituted with one to two substituents independently selected from amino and methylcarbonyl; and wherein each of said five to seven membered ring, said bicyclic ring, and said biphenyl in the definition of $R^2$ is optionally substituted with one to three fluoro, or optionally substituted with one to two substituents independently selected from hydroxy, $(C_1–C_3)$ alkyl, amino, and methylcarbonyl.

15. A compound of claim 1 wherein:
$A^1$ is hydroxy;
$A^2$, $A^3$, and $A^4$ are hydrogen;
p is 0;
$R^1$ is phenyl, cyclohexyl, pyridyl, thienyl, isopropyl, or adamantyl; wherein each of said $R^1$ groups is optionally substituted with one to three fluoro, or optionally substituted with one substituent selected from iodo, chloro, bromo, hydroxy, methoxy, pyrrolidino-ethoxy, dimethylamino, COOR$^7$ or ethenyl-CONR$^4$R$^5$;
X is CH$_2$, CH$_2$-phenylene, CO$_2$, CO—(C$_0$–C$_2$)alkylene, or SO$_2$—(C$_0$–C$_2$)alkylene; and
$R^2$ is methyl, t-butyl, phenyl, cyclohexyl, isoxazoyl, tetrahydropyranyl, naphthyl, or benzodioxolyl; wherein each of said methyl or t-butyl is optionally substituted with one to three fluoro, or optionally substituted with one to two substituents independently selected from amino and methylcarbonyl; and wherein each of said phenyl, cyclohexyl, isoxazolyl, tetrahydropyranyl, naphthyl, or benzodiozolyl is optionally sutstituted with one to three fluoro, or optionally substituted with one to two substituents independently selected from hydroxy, $(C_1–C_3)$alkyl, amino, and methylcarbonyl;
$R^4$ $R^5$ are each methyl, or $R^4$ and $R^5$ taken together with the nitrogen atom to which they are attached are piperidino or morpholino; and
$R^7$ is hydrogen or methyl.

16. A compound of claim 15 wherein $R^1$ is phenyl or cyclohexyl, wherein each of said phenyl or said cyclohexyl is optionally substituted with one to three fluoro, or optionally substituted with one substituent selected from iodo, chloro, bromo hydroxy, methoxy, pyrrolidino-ethoxy, dimethylamino, COOR$^7$ or ethenyl-CONR$^4$R$^5$;
$R^4$ and $R^5$ are each methyl, or $R^4$ and $R^5$ taken together with the nitrogen atom to which they are attached are piperidino or morpholino; and
$R^7$ is hydrogen or methyl.

17. A compound of claim 15 wherein said phenyl or said cyclohexyl in the definition of $R^1$ is optionally substituted with one hydroxy or pyrrolidino-ethoxy.

18. A compound of claim 15 wherein X is CO or SO$_2$.

19. A compound of claim 15 wherein $R^2$ is trifluoromethyl or phenyl, wherein said phenyl is optionally substituted with one to three fluoro, or optionally substituted with one to two substituents independently selected from hydroxy, $(C_1–C_3)$ alkyl, amino, and methylcarbonyl.

20. A compound of claim 15 wherein:
$R^1$ is phenyl or cyclohexyl, said phenyl or said cyclohexyl each optionally substituted with one hydroxy or pyrrolidino-ethoxy;
X is CO or SO$_2$; and
$R^2$ is trifluoromethyl or phenyl; wherein said phenyl is optionally substituted with one to three fluoro, or optionally substituted with one to two substituents independently selected from hydroxy, $(C_1–C_3)$alkyl, amino, and methylcarbonyl.

21. A compound of claim 15 wherein said compound is 1-(4-hydroxy-phenyl)-2-phenyl-1,2,3,4-tetrahydroisoquinolin-6-ol, having the structure

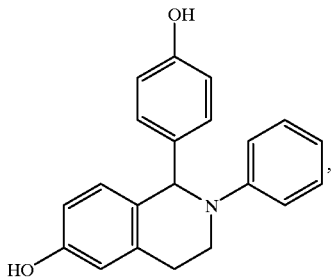

3-[4-(6-hydroxy-2-phenyl-1,2,3,4-tetrahydroisoquinolin-1-yl)-phenyl]-1-piperidin-1-yl-propenone, having the structure

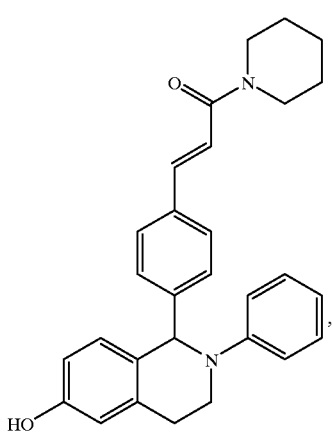

3-[4-(6-hydroxy-2-phenyl-1,2,3,4-tetrahydroisoquinolin-1-yl)-phenyl]-1-morpholin-4-yl-propenone, having the structure

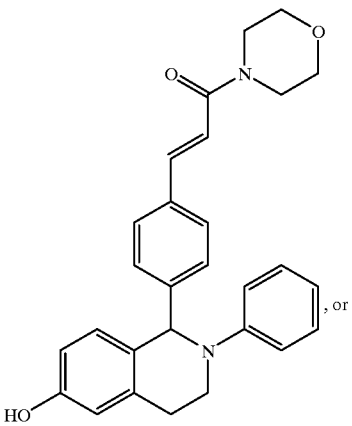

3-[4-(6-hydroxy-2-phenyl-1,2,3,4-tetrahydroisoquinolin-1-yl)-phenyl]-N,N-dimethyl-acrylamide, having the structure

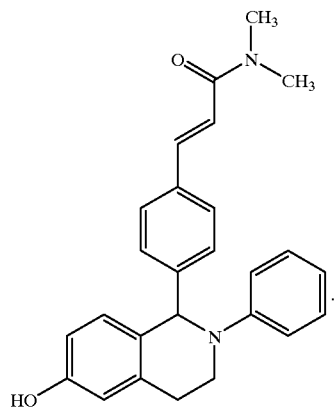

22. A compound of claim 15 wherein said compound is 2-benzyl-1-[4-(2-pyrrolidin-1-yl-ethoxy)phenyl]-1,2,3,4-tetrahydroisoquinolin-6-ol, having the structure

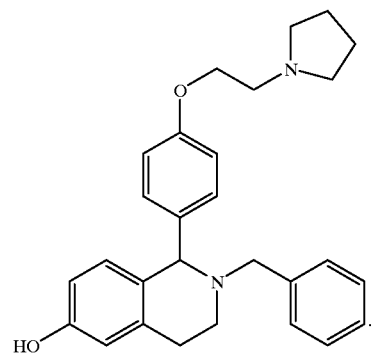

23. A compound of claim 15 wherein said compound is 2,2,2-trifluoro-1-[6-hydroxy-1-(4-hydroxyphenyl)-3,4-dihydro-1H-isoquinolin-2-yl]-ethanone, having the structure

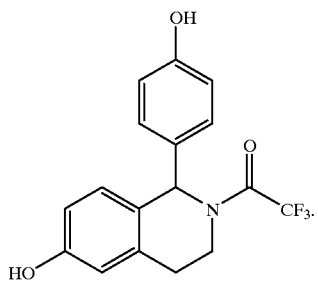

24. A compound of claim 23 wherein said compound is 2,2,2-trifluoro-1-[6-hydroxy-1(R)-(4-hydroxyphenyl)-3,4-dihydro-1H-isoquinolin-2-yl]-ethanone, having the structure

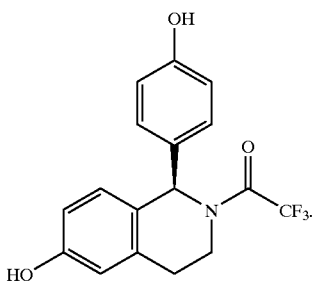

25. A compound of claim 15 wherein said compound is 2-benzenesulfonyl-1-[4-(2-pyrrolidin-1yl-ethoxy)phenyl]-1,2,3,4-tetrahydroisoquinolin-6-ol, having the structure

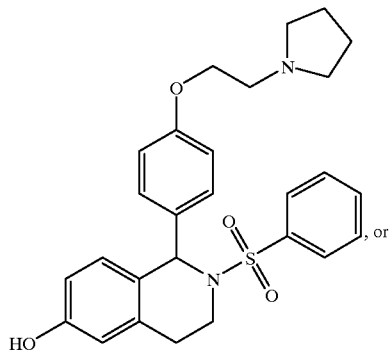, or 2-(4-isopropylbenzenesulfonyl)1-[4-(2-pyrrolidin-1-yl-ethoxy)phenyl]-1,2,3,4-tetrahydroisoquinolin-6-ol, having the structure

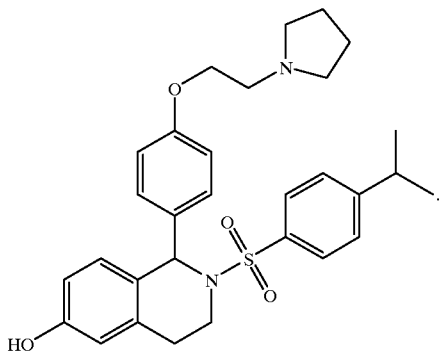.

26. A compound of claim 1 wherein said compound is of formula (I):

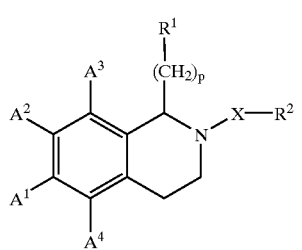

wherein:
$A^1$ is hydroxy, $(C_1-C_4)$alkoxy, $(C_1-C_4)$alkanoyloxy, or pyrrolidino-ethoxy;
$A^2$, $A^3$, and $A^4$ are hydrogen;
p is 0 or 1;
$R^1$ is $(C_1-C_4)$alkyl, $(C_4-C_7)$cycloalkyl, adamantyl, phenyl, pyridyl, or thienyl, wherein each of said phenyl, pyridyl, or thienyl groups is optionally substituted with one to three fluoro, or optionally substituted with one substituent selected from iodo, chloro, bromo, hydroxy, methoxy, dimethylamino, $OCH_2CH_2NR^8R^9$, $COOR^7$, ethenyl-$COOR^7$ or ethenyl-$CONR^4R^5$;
X is $CH_2$, $CH_2$-phenylene, $CO_2$, CO—$(C_0-C_2)$alkylene, or $SO_2$—$(C_0-C_2)$alkylene;

$R^2$ is $(C_1-C_7)$alkyl, phenyl, benzyl, thienyl, $(C_5-C_7)$cycloalkyl, isoxazolyl, imidazolyl, tetrahydropyranyl, naphthyl, or benzodioxolyl, wherein said $(C_1-C_7)$alkyl is optionally substituted with one to three fluoro, or optionally substituted with one to two substituents independently selected from amino and methylcarbonyl, and wherein each of said phenyl, thienyl, $(C_5-C_7)$cycloalkyl, isoxazolyl, tetrahydropyranyl, naphthyl, and benzodioxolyl is optionally substituted with one to three fluoro, or optionally substituted with one to two substituents independently selected from hydroxy, methoxy, $(C_1-C_3)$alkyl, amino, and methylcarbonyl; and
$R^4$ and $R^5$ are each methyl, or $R^4$ and $R^5$ taken together with the nitrogen atom to which they are attached are pyrrolidino, piperidino, hexamethyleneimino, or morpholino.

27. A compound of claim 26 wherein:
p is 0;
X is $SO_2$;
$R^1$ is $(C_1-C_4)$alkyl, $(C_4-C_7)$cycloalkyl, adamantyl, phenyl, pyridyl, or thienyl, wherein each of said phenyl, pyridyl, or thienyl groups is optionally substituted with one to three fluoro, or with one substituent selected from iodo, chloro, bromo, hydroxy, methoxy, dimethylamino, $OCH_2CH_2NR^8R^9$, $COOR^7$ or ethenyl-$CONR^4R^5$;
$R^2$ is phenyl, benzyl, napthyl, isoxazoyl, $(C_5-C_7)$cycloalkyl, or $(C_1-C_4)$alkyl, wherein each of said phenyl, benzyl, napthyl, and isoxazoyl is optionally substituted with one to two $(C_1-C_3)$alkyl groups; and
$R^4$ and $R^5$ are each methyl, or $R^4$ and $R^5$ taken together with the nitrogen atom to which they are attached are pyrrolidino, piperidino, hexamethyleneimino, or morpholino.

28. A compound of claim 27 wherein $R^1$ is phenyl or thienyl, said phenyl or thienyl each optionally substituted with one to three fluoro or with one $OCH_2CH_2NR^8R^9$.

29. A compound of claim 29 wherein:
p is 0;
X is CO;
$R^1$ is $(C_1-C_4)$alkyl, $(C_4-C_7)$cycloalkyl, adamantyl, phenyl, pyridyl, or thienyl, wherein each of said phenyl, pyridyl, or thienyl groups is optionally substituted with one to three fluoro, or optionally substituted with one substituent selected from iodo, chloro, bromo, hydroxy, methoxy, dimethylamino, $OCH_2CH_2NR^8R^9$, $COOR^7$, or ethenyl-$CONR^4R^5$ wherein $R^4$ and $R^5$ are both methyl, or $R^4$ and $R^5$ taken together with the nitrogen atom to which they are attached form pyrrolidino, piperidino, hexamethyleneimino, or morpholino; and
$R^2$ is $(C_5-C_7)$cycloalkyl, $(C_3-C_7)$alkyl, napthyl, or trifluoromethyl, wherein said $(C_3-C_7)$alkyl is optionally substituted with one to three fluoro.

30. A compound of claim 29 wherein $R^1$ is phenyl or thienyl, said phenyl or thienyl each optionally substituted with one to three fluoro or with one $OCH_2CH_2NR^8R^9$.

31. A compound of claim 26 wherein:
p is 0;
X is $CH_2$;
$R^1$ is $(C_1-C_4)$alkyl, $(C_4-C_7)$cycloalkyl, adamantyl, phenyl, pyridyl, or thienyl, wherein each of said phenyl, pyridyl, or thienyl groups is optionally substituted with one to three fluoro, or with one substituent selected from iodo, chloro, bromo, hydroxy, methoxy, dimethylamino, OCH$_2$CH$_2$NR$^8$R$^9$, COOR$^7$, or ethenyl-CONR$^4$R$^5$ wherein R$^4$ and R$^5$ are both methyl, or R$^4$ and R$^5$ taken together with the nitrogen atom to which they are attached form pyrrolidino, piperidino, hexamethyleneimino, or morpholino; and R$^2$ is phenyl, thienyl, or benzodioxolyl, said phenyl, thienyl, or benzodioxolyl each optionally substituted with one to three fluoro or one imidazoyl group.

32. A compound of claim 31 wherein R$^1$ is phenyl or thienyl, said phenyl or thienyl each optionally substituted with one to three fluoro or with one OCH$_2$CH$_2$NR$^8$R$^9$.

33. A compound of claim 26 wherein:

p is 0;

X is CO$_2$;

R$^1$ is (C$_1$–C$_4$)alkyl, (C$_4$–C$_7$)cycloalkyl, adamantyl, phenyl, pyridyl, or thienyl, wherein each of said phenyl, pyridyl, or thienyl groups is optionally substituted with one to three fluoro, or with one substituent selected from iodo, chloro, bromo, hydroxy, methoxy, dimethylamino, OCH$_2$CH$_2$NR$^8$R$^9$, COOR$^7$, or ethenyl-CONR$^4$R$^5$ wherein R$^4$ and R$^5$ are both methyl, or R$^4$ and R$^5$ taken together with the nitrogen atom to which they are attached form pyrrolidino, piperidino, hexamethyleneimino, or morpholino; and R$^2$ is phenyl or (C$_1$–C$_4$)alkyl, said phenyl or (C$_1$–C$_4$)alkyl each optionally substituted with one to three fluoro.

34. A compound of claim 33 wherein R$^1$ is phenyl or thienyl, said phenyl or thienyl each optionally substituted with one to three fluoro or with one OCH$_2$CH$_2$NR$^8$R$^9$.

35. A compound of claim 1 wherein said compound is of formula (II):

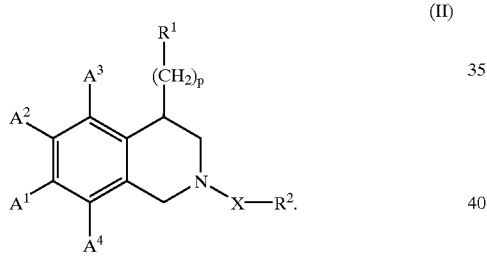

(II)

36. A compound of claim 35 wherein:

A$^1$ is hydroxy, (C$_1$–C$_4$)alkoxy, or (C$_1$–C$_4$)alkanoyloxy;

A$^2$, A$^3$, and A$^4$ are hydrogen;

p is 0 or 1;

R$^1$ is (C$_1$–C$_4$)alkyl, (C$_4$–C$_7$)cycloalkyl, adamantyl, phenyl, pyridyl, or thienyl, wherein each of said phenyl, pyridyl, thienyl, or (C$_4$–C$_7$)cycloalkyl groups is optionally substituted with one to three fluoro, or optionally substituted with one substituent selected from iodo, chloro, bromo, hydroxy, methoxy, dimethylamino, OCH$_2$CH$_2$NR$^8$R$^9$, COOR$^7$ or ethenyl-CONR$^4$R$^5$;

X is CH$_2$, CH$_2$-phenylene, CO$_2$, CO—(C$_0$–C$_2$)alkylene, or SO$_2$—(C$_0$–C$_2$)alkylene;

R$^2$ is (C$_1$–C$_7$)alkyl, phenyl, benzyl, thienyl, (C$_5$–C$_7$) cycloalkyl, isoxazolyl, tetrahydropyranyl, naphthyl, or benzodioxolyl, wherein said (C$_1$–C$_7$)alkyl is optionally substituted with one to three fluoro, or optionally substituted with one to two substituents independently selected from amino and methylcarbonyl, and wherein each of said phenyl, thienyl, (C$_5$–C$_7$)cycloalkyl, isoxazolyl, tetrahydropyranyl, naphthyl, and benzodioxolyl is optionally substituted with one to three fluoro, or optionally substituted with one to two substituents independently selected from hydroxy, methoxy, and (C$_1$–C$_3$)alkyl; and R$^4$ and R$^5$ are each methyl, or R$^4$ and R$^5$ taken together with the nitrogen atom to which they are attached are pyrrolidino, piperidino, hexamethyleneimino, or morpholino.

37. A compound of claim 15 wherein said compound is of formula (II).

38. A compound of claim 37 if wherein said compound is 2,2,2-trifluoro-1-[7-hydroxy-4-(4-hydroxy-phenyl)-3,4-dihydro-1H-isoquinolin-2-yl]-ethanone, having the structure

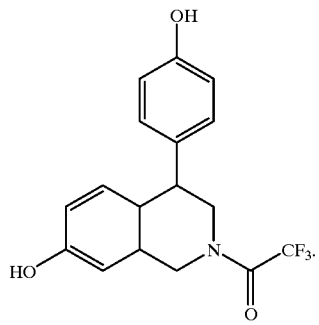

39. A compound of the formula:

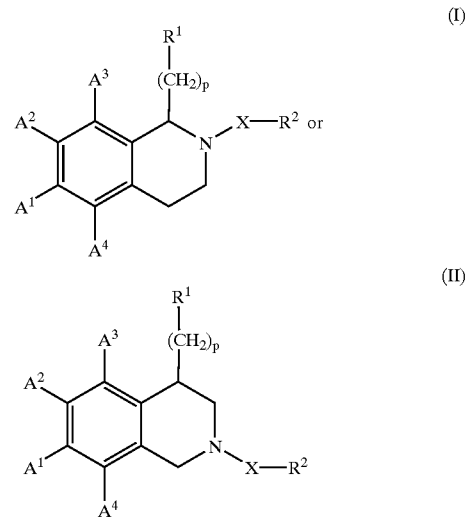

wherein:

A$^1$ is hydrogen, hydroxy, (C$_1$–C$_4$)alkoxy, or (C$_1$–C$_4$) alkanoyloxy, said (C$_1$–C$_4$)alkoxy or said (C$_1$–C$_4$)

alkanoyloxy being optionally substituted by hydroxy, halo, di($C_1$–$C_4$alkyl)amino or a partially saturated, fully saturated, or fully unsaturated five to twelve membered ring optionally comprising one to four heteroatoms independently selected from oxygen, sulfur, and nitrogen;

$A^2$, $A^3$, and $A^4$ are independently selected from hydrogen, hydroxy, ($C_1$–$C_4$)alkoxy, and halo;

$R^1$ is ($C_1$–$C_7$)alkyl; adamantyl; a partially saturated, fully saturated, or fully unsaturated three to twelve membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, said bicyclic ring system optionally comprising one to four heteroatoms independently selected from oxygen, sulfur, and nitrogen; wherein each of the above $R^1$ groups is optionally substituted with one to seven fluoro, or optionally substituted with one to three substituents independently selected from Group A, wherein Group A consists of hydroxy, chloro, bromo, iodo, ($C_1$–$C^4$)alkyl, ($C_1$–$C_4$)alkoxy, ($C_3$–$C_8$)cycloalkyl, $R^3$—($C_1$–$C_4$)alkoxy, ($C_2$–$C_4$)alkenyl-COOR$^7$, ($C_0$–$C_4$)alkyl-COOR$^7$, ($C_1$–$C_4$)alkanoyloxy-($C_2$–$C_4$)alkenyl, ($C_2$–$C_4$)alkenyl-CONR$^4$R$^5$, ($C_0$–$C_4$)alkyl-CONR$^4$R$^5$, ($C_0$–$C_4$)alkyl-NR$^4$R$^5$, OCH$_2$CH$_2$NR$^8$R$^9$, propyl-R$^8$R$^9$, and SO$_2$—R$^6$;

X is ($C_0$–$C_1$)alkylene-phenylene-($C_0$–$C_1$)alkylene, CO$_2$, CO, ($C_1$–$C_3$)alkylene-CO—($C_1$–$C_3$)alkylene, ($C_0$–$C_3$)alkylene-CO—($C_2$–$C_3$)alkylene, ($C_2$–$C_3$)alkylene-CO—($C_0$–$C_3$)alkylene, or ($C_0$–$C_4$)alkylene-SO$_2$—($C_0$–$C_4$)alkylene;

$R^2$ is ($C_1$–$C_9$)alkyl; ($C_2$–$C_4$)alkenyl; benzhydryl; a partially saturated, fully saturated, or fully unsaturated three to eight membered ring optionally comprising one to four heteroatoms selected independently from oxygen, sulfur, and nitrogen; a bicyclic ring consisting of two fused independently partially saturated, fully saturated, or fully unsaturated five to six membered rings, and said bicyclic ring optionally comprising one to four heteroatoms independently selected from oxygen, sulfur, and nitrogen; or a bicyclic ring system consisting of two rings joined by a covalent bond said rings being independently partially saturated, fully saturated, or fully unsaturated three to eight membered rings, and said bicyclic ring system optionally comprising one to four heteroatoms independently selected from oxygen, sulfur, and nitrogen; wherein said ($C_1$–$C_9$)alkyl is optionally substituted with one to seven fluoro, or optionally substituted with one to three substituents independently selected from Group B, wherein Group B consists of chloro, ($C_1$–$C_4$)alkoxy, amino, and ($C_1$–$C_4$)alkylcarbonyl; wherein said ($C_2$–$C_4$)alkenyl is optionally substituted with one to three substituents independently selected from Group C, wherein Group C consists of halo, ($C_1$–$C_4$)alkoxy, amino, and ($C_1$–$C_4$)alkylcarbonyl; and wherein said benzhydryl, said three to eight membered ring, said bicyclic ring, and said bicyclic ring system are each optionally substituted with one to three substituents independently selected from Group D, wherein Group D consists of halo, hydroxy, ($C_1$–$C_4$)alkyl, ($C_1$–$C_4$alkoxy, imidazolyl, amino, ($C_1$–$C_4$) alkylcarbonylamino, and ($C_1$–$C_4$)alkylcarbonyl;

$R^3$ at each occurrence is independently pyrrolidino, piperidino, morpholino, or dimethylamino;

$R^4$ and $R^5$ at each occurrence are independently hydrogen, ($C_1$–$C_4$)alkyl, hydroxy($C_1$–$C_4$)alkyl, ($C_1$–$C_4$)alkoxy-($C_1$–$C_4$)alkylene, or ($C_3$–$C_8$) cycloalkyl, or $R^4$ and $R^5$ taken together with the nitrogen atom to which they are attached are pyrrolidino, piperidino, morpholino, or hexamethyleneimino;

$R^6$ at each occurrence is independently imidazolyl, thienyl, benzathienyl, or isoxazyl, each optionally substituted with one to three substituents independently selected from ($C_1$–$C_4$)alkyl;

$R^7$ at each occurrence is independently hydrogen or ($C_1$–$C_4$)alkyl;

$R^8$ and $R^9$ are independently methyl or ethyl, or $R^8$ and $R^9$ taken together with the nitrogen atom to which they are attached are pyrrolidino, piperidino, morpholino, or hexamethyleneimino; and p is 0, 1, or 2.

40. A compound of the formula:

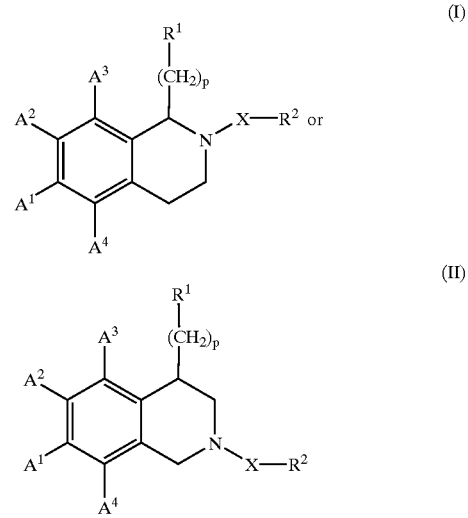

wherein:

$A^1$ is hydrogen, hydroxy, ($C_1$–$C_4$)alkoxy, or ($C_1$–$C_4$) alkanoyloxy, said ($C_1$–$C_4$)alkoxy or said ($C_1$–$C_4$) alkanoyloxy being optionally substituted by hydroxy, halo, di($C_1$–$C_4$alkyl)amino or a partially saturated, fully saturated, or fully unsaturated five to twelve membered ring optionally having up to four heteroatoms independently selected from oxygen, sulfur, and nitrogen;

$A^2$, $A^3$, and $A^4$ are independently selected from hydrogen, hydroxy, ($C_1$–$C_4$)alkoxy, and halo;

$R^1$ is ($C_1$–$C_7$)alkyl; adamantyl; a partially saturated, fully saturated, or fully unsaturated three to twelve membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, said bicyclic ring system optionally comprising one to four heteroatoms independently selected from oxygen, sulfur, and nitrogen; wherein each of the above $R^1$ groups is optionally substituted with one to seven fluoro, or optionally substituted with one to three substituents independently selected from Group A, wherein Group A consists of hydroxy, chloro, bromo, iodo, $(C_1-C_4)$alkyl, $(C_1-C_4)$alkoxy, $(C_3-C_8)$cycloalkyl, $R^3$—$(C_1-C_4)$alkoxy, $(C_2-C_4)$alkenyl-$COOR^7$, $(C_0-C_4)$alkyl-$COOR^7$, $(C_1-C_4)$alkanoyloxy-$(C_2-C_4)$alkenyl, $(C_2-C_4)$alkenyl-$CONR^4R^5$, $(C_0-C_4)$alkyl-$CONR^4R^5$, $(C_0-C_4)$alkyl-$NR^4R^5$, $OCH_2CH_2NR^8R^9$, propyl-$R^8R^9$ and $SO_2$—$R^6$;

X is a covalent bond, $(CH_2)_n$ wherein n is 1, 2, or 3, $(C_0-C_1)$alkylene-phenylene-$(C_0-C_1)$alkylene, $CO_2$, $(C_0-C_3)$alkylene-CO—$(C_0-C_3)$alkylene, or $(C_0-C_4)$alkylene-$SO_2$—$(C_0-C_4$alkylene);

$R^2$ is $(C_1-C_9)$alkyl; $(C_2-C_4)$alkenyl; benzhydryl; a partially saturated, fully saturated, or fully unsaturated four to five membered ring optionally comprising one to three heteroatoms selected independently from oxygen, sulfur, and nitrogen; a partially saturated, fully saturated, or fully unsaturated seven to eight membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, wherein said bicyclic ring system optionally comprises one to four heteroatoms independently selected from oxygen, sulfur, and nitrogen; wherein said $(C_1-C_9)$alkyl is optionally substituted with one to seven fluoro, or optionally substituted with one to three substituents independently selected from Group B, wherein Group B consists of chloro, $(C_1-C_4)$alkoxy, amino, and $(C_1-C_4)$alkylcarbonyl; wherein said $(C_2-C_4)$alkenyl is optionally substituted with one to three substituents independently selected from Group C, wherein Group C consists of halo, $(C_1-C_4)$alkoxy, amino, and $(C_1-C_4)$alkylcarbonyl; and wherein said benzhydryl, said four to five membered ring, said seven to eight membered ring, said bicyclic ring, and said bicyclic ring system are optionally substituted with one to three substituents independently selected from Group D, wherein Group D consists of halo, hydroxy, $(C_1-C_4)$alkyl, $(C_1-C_4)$alkoxy, imidazolyl, amino, $(C_1-C_4)$alkylcarbonylamino, and $(C_1-C_4)$alkylcarbonyl;

$R^3$ at each occurrence is independently pyrrolidino, piperidino, morpholino, or dimethylamino;

$R^4$ and $R^5$ at each occurrence are independently hydrogen, $(C_1-C_4)$alkyl, hydroxy$(C_1-C_4)$alkyl, $(C_1-C_4)$alkoxy-$(C_1-C_4)$alkylene, or $(C_3-C_8)$cycloalkyl, or $R^4$ and $R^5$ taken together with the nitrogen atom to which they are attached form pyrrolidino, piperidino, morpholino, or hexamethyleneimino;

$R^6$ at each occurrence is independently imidazolyl, thienyl, benzathienyl, or isoxazyl, said imidazolyl, thienyl, benzathienyl, or isoxazyl each optionally substituted with one to thee substituents independently selected from $(C_1-C_4)$alkyl;

$R^7$ at each occurrence is independently hydrogen or $(C_1-C_4)$alkyl;

$R^8$ and $R^9$ at each occurrence are independently methyl or ethyl, or $R^8$ and $R^9$ taken together with the nitrogen atom to which they are attached are pyrrolidino, piperidino, morpholino, or hexamethyleneimino; and p is 0, 1, or 2;

with the proviso that when X is $(CH_2)_2$ or $(CH_2)_3$, p is 0, and $R^1$ is phenyl or phenyl substituted with a single chloro, fluoro, bromo, hydroxy, methoxy, pyrrolidinoethoxy, piperidinoethoxy or morpholinoethoxy substituent, then $R^2$ is not tert-butyl or cyclopentyl.

41. A compound of claim 40 wherein:

$A^1$ is hydroxy;

$A^2$, $A^3$, and $A^4$ are hydrogen; and p is 0.

42. A compound of claim 41 wherein $R^1$ is phenyl optionally substituted with one to three fluoro, or optionally substituted with one substituent selected from Group A.

43. A compound of claim 41 wherein $R^1$ is phenyl substituted with one substituent selected from hydroxy, halo, piperidino-ethoxy, pyrrolidino-ethoxy, or morpholino-ethoxy.

44. A compound of claim 41 wherein $R^2$ is $(C_1-C_7)$alkyl; propenyl; a partially saturated, fully saturated, or fully unsaturated five membered ring optionally comprising one to two heteroatoms selected independently from oxygen, sulfur, and nitrogen; a bicyclic ring consisting of two fused independently partially saturated, fully saturated, or fully unsaturated five to six membered rings, wherein said bicyclic ring optionally comprises one to two oxygen atoms; or biphenyl; wherein said $(C_1-C_7)$alkyl is optionally substituted with one to seven fluoro, or optionally substituted with one to three substituents independently selected from Group B; wherein said propenyl is optionally substituted with one to three substituents independently selected from Group C; and wherein each of said five membered ring, said bicyclic ring, and said biphenyl is optionally substituted with one to three substituents independently selected from Group D.

45. A compound of claim 44 wherein $R^2$ is trifluoromethyl.

46. A compound of claim 41 wherein X is a covalent bond, $CH_2$, $CH_2$-phenylene, $CO_2$, CO—$(C_0-C_2)$alkylene, or $SO_2$—$(C_0-C_2)$alkylene.

47. A compound of claim 46 wherein X is CO or $SO_2$.

48. A compound of the formula:

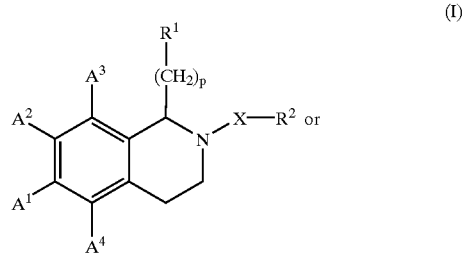

(I)

-continued (II)

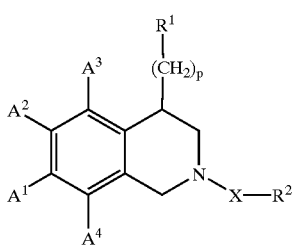

wherein:
- $A^1$ is hydrogen, hydroxy, $(C_1-C_4)$alkoxy, or $(C_1-C_4)$ alkanoyloxy, said $(C_1-C_4)$alkoxy or said $(C_1-C_4)$ alkanoyloxy optionally substituted by hydroxy, halo, di$(C_1-C_4$alkyl)amino or a partially saturated, fully saturated, or fully unsaturated five to twelve membered ring optionally comprising one to four heteroatoms independently selected from oxygen, sulfur, and nitrogen;
- $A^2$, $A^3$, and $A^4$ are independently selected from hydrogen, hydroxy, $(C_1-C_4)$alkoxy, and halo;
- $R^1$ is $(C_1-C_7)$alkyl; adamantyl; a partially saturated, fully saturated, or fully unsaturated three to twelve membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, said bicyclic ring system optionally comprising one to four heteroatoms independently selected from oxygen, sulfur, and nitrogen; wherein each of the above $R^1$ groups is optionally substituted with one to seven fluoro, or optionally substituted with one to three substituents independently selected from Group A, wherein Group A consists of hydroxy, chloro, bromo, iodo, $(C_1-C_4)$alkyl, $(C_1-C_4)$ alkoxy, $(C_3-C_8)$cycloalkyl, $R^3$—$(C_1-C_4)$alkoxy, $(C_2-C_4)$alkenyl-COOR$^7$, $(C_0-C_4$alkyl-COOR$^7$, $(C_1-C_4)$alkanoyloxy-$(C_2-C_4)$alkenyl, $(C_2-C_4)$alkenyl-CONR$^4$R$^5$, $(C_0-C_4)$alkyl-CONR$^4$R$^5$, $(C_0-C_4)$alkyl-NR$^4$R$^5$, OCH$_2$CH$_2$NR$^8$R$^9$, propyl-R$^8$R$^9$ and SO$_2$—R$^6$;
- X is a covalent bond, $(CH_2)_n$ where n is 1, 2, or 3, $(C_0-C_1)$alkylene-phenylene-$(C_0-C_1)$alkylene, CO$_2$, $(C_0-C_3)$alkylene-CO—$(C_0-C_3)$alkylene, or $(C_0-C_4)$ alkylene-SO$_2$—$(C_0-C_4)$alkylene;
- $R^2$ is a partially saturated or fully saturated six membered ring optionally comprising one to three heteroatoms selected independently from oxygen, sulfur, and nitrogen; wherein said six membered ring is optionally substituted with one to three substituents independently selected from Group D, wherein Group D consists of halo, hydroxy, $(C_1-C_4)$alkyl, $(C_1-C_4)$alkoxy, imidazolyl, amino, $(C_1-C_4)$alkylcarbonylamino, and $(C_1-C_4)$alkylcarbonyl;
- $R^3$ at each occurrence is independently pyrrolidino, piperidino, morpholino, or dimethylamino;
- $R^4$ and $R^5$ at each occurrence are independently hydrogen, $(C_1-C_4)$alkyl, hydroxy$(C_1-C_4)$alkyl, $(C_1-C_4)$alkoxy-$(C_1-C_4)$alkylene, or $(C_3-C_8)$ cycloalkyl, or $R^4$ and $R^5$ taken together with the nitrogen atom to which they are attached form pyrrolidino, piperidino, morpholino, or hexamethyleneimino;
- $R^6$ at each occurrence is independently imidazolyl, thienyl, benzathienyl, or isoxazyl, each optionally substituted with one to three substituents independently selected from $(C_1-C_4)$alkyl;
- $R^7$ at each occurrence is independently hydrogen or $(C_1-C_4)$alkyl;
- $R^8$ and $R^9$ at each occurrence are independently methyl or ethyl, or $R^8$ and $R^9$ taken together with the nitrogen atom to which they are attached form pyrrolidino, piperidino, morpholino, or hexamethyleneimino; and
- p is 0, 1, or 2.

49. A compound of the formula:

(II)

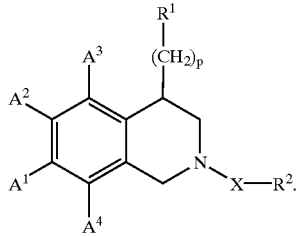

wherein:
- $A^1$ is hydrogen, hydroxy, $(C_1-C_4)$alkoxy, or $(C_1-C_4)$ alkanoyloxy, said $(C_1-C_4)$alkoxy or said $(C_1-C_4)$ alkanoyloxy being optionally substituted by hydroxy, halo, di$(C_1-C_4$alkyl)amino or a partially saturated, fully saturated, or fully unsaturated five to twelve membered ring optionally comprising one to four heteroatoms independently selected from oxygen, sulfur, and nitrogen;
- $A^2$, $A^3$, and $A^4$ are independently selected from hydrogen, hydroxy, $(C_1-C_4)$alkoxy, and halo;
- $R^1$ is $(C_1-C_7)$alkyl; adamantyl; a partially saturated, fully saturated, or fully unsaturated three to twelve membered ring optionally comprising one to four heteroatoms selected independently from oxygen, sulfur, and nitrogen; a bicyclic ring consisting of two fused independently partially saturated, fully saturated, or fully unsaturated five to six membered rings, said bicyclic ring optionally comprising one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, said bicyclic ring system optionally comprising one to four heteroatoms independently selected from oxygen, sulfur, and nitrogen; wherein each of the above $R^1$ groups is optionally substituted with one to seven fluoro, or optionally substituted with one to three substituents independently selected from Group A, wherein Group A consists of hydroxy, chloro, bromo, iodo, $(C_1-C_4)$alkyl, $(C_1-C_4)$ alkoxy, $(C_3-C_8)$cycloalkyl, $R^3$—$(C_1-C_4)$alkoxy, $(C_2-C_4)$alkenyl-COOR$^7$, $(C_0-C_4$alkyl-COOR$^7$, $(C_1-C_4)$alkanoyloxy-$(C_2-C_4)$alkenyl, $(C_2-C_4)$alkenyl-CONR$^4$R$^5$, $(C_0-C_4)$alkyl-CONR$^4$R$^5$, $(C_0-C_4)$alkyl-NR$^4$R$^5$, OCH$_2$CH$_2$NR$^8$R$^9$, propyl-R$^8$R$^9$ and SO$_2$—R$^6$;
- X is a covalent bond, $(CH_2)_n$ where n is 1, 2, or 3, $(C_0-C_1)$alkylene-phenylene-$(C_0-C_1)$alkylene, CO$_2$, ($C_0$–$C_3$)alkylene-CO—($C_0$–$C_3$)alkylene, or ($C_0$–$C_4$) alkylene-SO$_2$—($C_0$–$C_4$)alkylene;

$R^2$ is ($C_1$–$C_9$)alkyl; ($C_2$–$C_4$)alkenyl; benzhydryl; a partially saturated, fully saturated, or fully unsaturated three to eight membered ring optionally comprising one to four heteroatoms selected independently from oxygen, sulfur, and nitrogen; a bicyclic ring consisting of two fused independently partially saturated, fully saturated, or fully unsaturated five to six membered rings, wherein said bicyclic ring optionally comprises one to four heteroatoms independently selected from oxygen, sulfur, and nitrogen; or a bicyclic ring system consisting of two rings joined by a covalent bond, said rings being independently partially saturated, fully saturated, or fully unsaturated three to eight membered rings, wherein said bicyclic ring system optionally comprises one to four heteroatoms independently selected from oxygen, sulfur, and nitrogen; wherein said ($C_1$–$C_9$)alkyl is optionally substituted with one to seven fluoro, or optionally substituted with one to three substituents independently selected from Group B, wherein Group B consists of chloro, ($C_1$–$C_4$)alkoxy, amino, and ($C_1$–$C_4$)alkylcarbonyl; wherein said ($C_2$–$C_4$)alkenyl is optionally substituted with one to three substituents independently selected from Group C, wherein Group C consists of halo, ($C_1$–$C_4$)alkoxy, amino, and ($C_1$–$C_4$)alkylcarbonyl; and wherein said benzhydryl, said three to eight membered ring, said bicyclic ring, and said bicyclic ring system is optionally substituted with one to three substituents independently selected from Group D, wherein Group D consists of halo, hydroxy, ($C_1$–$C_4$)alkyl, ($C_1$–$C_4$)alkoxy, imidazolyl, amino, ($C_1$–$C_4$)alkylcarbonylamino, and ($C_1$–$C_4$)alkylcarbonyl;

$R^3$ at each occurrence is independently pyrrolidino, piperidino, morpholino, or dimethylamino;

$R^4$ and $R^5$ at each occurrence are independently hydrogen, ($C_1$–$C_4$)alkyl, hydroxy($C_1$–$C_4$)alkyl, ($C_1$–$C_4$)alkoxy-($C_1$–$C_4$)alkylene, or ($C_3$–$C_8$) cycloalkyl, or $R^4$ and $R^5$ taken together with the nitrogen atom to which they are attached form pyrrolidino, piperidino, morpholino, or hexamethyleneimino;

$R^6$ at each occurrence is independently imidazolyl, thienyl, benzathienyl, or isoxazyl, each optionally substituted with one to three substituents independently selected from ($C_1$–$C_4$)alkyl;

$R^7$ at each occurrence is independently hydrogen or ($C_1$–$C_4$)alkyl;

$R^8$ and $R^9$ at each occurrence are independently methyl or ethyl, or $R^8$ and $R^9$ taken together with the nitrogen atom to which they are attached form pyrrolidino, piperidino, morpholino, or hexamethyleneimino; and p is 0,1, or 2.

50. A compound of claim 49 wherein:

$A^1$ is hydroxy, ($C_1$–$C_4$)alkoxy, or ($C_1$–$C_4$)alkanoyloxy;

$A^2$, $A^3$, and $A^4$ are hydrogen;

p is 0 or 1;

$R^1$ is ($C_1$–$C_4$)alkyl, ($C_4$–$C_7$)cycloalkyl, adamantyl, phenyl, pyridyl, or thienyl, wherein each of said phenyl, pyridyl, thienyl, or ($C_5$–$C_7$)cycloalkyl groups is optionally substituted with one to three fluoro, or optionally substituted with one substituent selected from iodo, chloro, bromo, hydroxy, methoxy, dimethylamino, OCH$_2$CH$_2$NR$^8$R$^9$, COOR$^7$, or ethenyl-CONR$^4$R$^5$ wherein $R^4$ and $R^5$ are both methyl, or $R^4$ and $R^5$ taken together with the nitrogen atom to which they are attached form pyrrolidino, piperidino, hexamethyleneimino, or morpholino;

X is CH$_2$, CH$_2$-phenylene, CO$_2$, CO—($C_0$–$C_2$)alkylene, or SO$_2$—($C_0$–$C_2$)alkylene; and $R^2$ is ($C_1$–$C_7$)alkyl, phenyl, benzyl, thienyl, ($C_5$–$C_7$) cycloalkyl, isoxazolyl, tetrahydropyranyl, naphthyl, or benzodioxolyl, wherein said ($C_1$–$C_7$)alkyl is optionally substituted with one to three fluoro, or optionally substituted with one to two substituents independently selected from amino and methylcarbonyl, and wherein each of said phenyl, thienyl, cyclohexyl, isoxazolyl, tetrahydropyranyl, naphthyl, and benzodioxolyl is optionally substituted with one to three fluoro, or optionally substituted with one to two substituents independently selected from hydroxy, methoxy, and ($C_1$–$C_3$)alkyl.

51. A pharmaceutical composition comprising a compound of claim 1 and a pharmaceutically acceptable vehicle, carrier, or diluent.

52. A pharmaceutical composition comprising a compound of claim 39 and a pharmaceutically acceptable vehicle, carrier, or diluent.

53. A pharmaceutical composition comprising a compound of claim 40 and a pharmaceutically acceptable vehicle, carrier, or diluent.

54. A pharmaceutical composition comprising:

a compound of claim 1;

an anabolic agent, a prodrug thereof, or a pharmaceutically acceptable salt of said anabolic agent or a said prodrug; and a pharmaceutically acceptable vehicle, carrier, or diluent.

55. A pharmaceutical composition comprising:

a compound of claim 1;

growth hormone, a growth hormone secretagogue, a prodrug thereof, or a pharmaceutically acceptable salt of said growth hormone secretagogue or a said prodrug; and a pharmaceutically acceptable vehicle, carrier, or diluent.

56. A pharmaceutical composition comprising:

a compound of claim 1;

a prostaglandin agonist/antagonist, a prodrug thereof, or a pharmaceutically acceptable salt of said prostaglandin agonist/antagonist or a said prodrug; and a pharmaceutically acceptable vehicle, carrier, or diluent.

57. A pharmaceutical composition comprising:

a compound of claim 1;

parathyroid hormone or sodium fluoride; and a pharmaceutically acceptable vehicle, carrier, or diluent.

* * * * *